United States Patent
Mollard et al.

(10) Patent No.: US 10,202,356 B2
(45) Date of Patent: Feb. 12, 2019

(54) JAK2 AND ALK2 INHIBITORS AND METHODS FOR THEIR USE

(71) Applicant: Tolero Pharmaceuticals, Inc., Lehi, UT (US)

(72) Inventors: Alexis Mollard, Salt Lake City, UT (US); Steven L. Warner, Sandy, UT (US); Gary A. Flynn, Oro Valley, AZ (US); Hariprasad Vankayalapati, Draper, UT (US); David J. Bearss, Alpine, UT (US)

(73) Assignee: Tolero Pharmaceuticals, Inc., Lehi, UT (US)

( * ) Notice: Subject to any disclaimer, the term of this patent is extended or adjusted under 35 U.S.C. 154(b) by 0 days.

(21) Appl. No.: 14/776,392

(22) PCT Filed: Mar. 13, 2014

(86) PCT No.: PCT/US2014/026595
§ 371 (c)(1),
(2) Date: Sep. 14, 2015

(87) PCT Pub. No.: WO2014/151871
PCT Pub. Date: Sep. 25, 2014

(65) Prior Publication Data
US 2016/0214944 A1    Jul. 28, 2016

Related U.S. Application Data

(60) Provisional application No. 61/785,460, filed on Mar. 14, 2013.

(51) Int. Cl.
| | |
|---|---|
| *C07D 239/48* | (2006.01) |
| *C07D 401/14* | (2006.01) |
| *C07D 401/12* | (2006.01) |
| *A61K 31/44* | (2006.01) |
| *A61K 31/496* | (2006.01) |
| *A61K 31/505* | (2006.01) |

(52) U.S. Cl.
CPC ............ *C07D 239/48* (2013.01); *A61K 31/44* (2013.01); *A61K 31/496* (2013.01); *A61K 31/505* (2013.01); *C07D 401/12* (2013.01); *C07D 401/14* (2013.01)

(58) Field of Classification Search
CPC .. C07D 239/48; C07D 401/12; C07D 401/14; A61K 31/44; A61K 31/496; A61K 31/505
See application file for complete search history.

(56) References Cited

U.S. PATENT DOCUMENTS

| | | | |
|---|---|---|---|
| 5,958,935 A | 9/1999 | Davis et al. | |
| 7,528,143 B2 | 5/2009 | Noronha et al. | |
| 7,625,903 B2 | 12/2009 | Johnson et al. | |
| 7,655,649 B2 | 2/2010 | Bilodeau et al. | |
| 7,741,330 B1 | 6/2010 | Chen et al. | |
| 7,834,024 B2 | 11/2010 | Li et al. | |
| 7,943,627 B2 | 5/2011 | Baenteli et al. | |
| 7,964,592 B2 | 6/2011 | Garcia-Echeverria et al. | |
| 8,133,900 B2 | 3/2012 | Hood et al. | |
| 8,138,199 B2 | 3/2012 | Noronha et al. | |
| 8,268,850 B2 | 9/2012 | Li et al. | |
| 8,338,439 B2 | 12/2012 | Singh et al. | |
| 2003/0166620 A1 | 9/2003 | Lee et al. | |
| 2005/0012070 A1 | 1/2005 | Inoue et al. | |
| 2005/0171134 A1 | 8/2005 | Davis et al. | |
| 2006/0270694 A1 | 11/2006 | Wong | |
| 2007/0191405 A1 | 8/2007 | Noronha et al. | |
| 2008/0182852 A1 | 7/2008 | Johnson et al. | |
| 2009/0298830 A1 | 12/2009 | Mann et al. | |
| 2010/0190770 A1 | 7/2010 | Li et al. | |
| 2010/0204221 A1 | 8/2010 | Vankayalapati et al. | |
| 2011/0230476 A1 | 9/2011 | Niu et al. | |
| 2012/0238540 A1 | 9/2012 | Holcomb et al. | |
| 2017/0246167 A1 | 8/2017 | Singh et al. | |

FOREIGN PATENT DOCUMENTS

| | | |
|---|---|---|
| CN | 101657431 A | 2/2010 |
| JP | 2003-512358 A | 4/2003 |
| RU | 2 343 148 C2 | 1/2009 |
| WO | 01/60816 A1 | 8/2001 |
| WO | 03/018021 A1 | 3/2003 |

(Continued)

OTHER PUBLICATIONS

Compound Summary for CID 49702158, PubChem, Dec. 23, 2015, 10 pages.

(Continued)

*Primary Examiner* — Yong S. Chong
(74) *Attorney, Agent, or Firm* — Seed IP Law Group LLP

(57) ABSTRACT

Compounds having activity as inhibitors of ALK2 kinase and/or JAK2 kinase are disclosed. The compounds have the following structure (I):

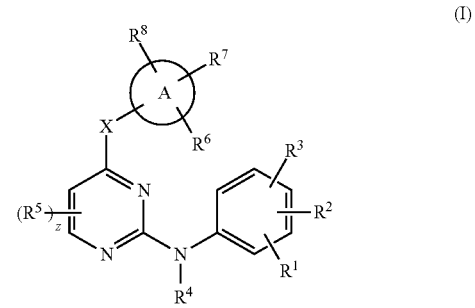

including stereoisomers, tautomers, pharmaceutically acceptable salts and prodrugs thereof, wherein $R^1$, $R^2$, $R^3$, $R^4$, $R^5$, $R^6$, $R^7$, $R^8$, X, z and A are as defined herein. Methods associated with preparation and use of such compounds, as well as pharmaceutical compositions comprising such compounds, are also disclosed.

10 Claims, 5 Drawing Sheets

(56) References Cited

FOREIGN PATENT DOCUMENTS

| WO | 03/063794 A2 | 8/2003 |
|---|---|---|
| WO | 2003/095448 A1 | 11/2003 |
| WO | 2004/074244 A2 | 9/2004 |
| WO | 2005/026130 A1 | 3/2005 |
| WO | 2005/082892 A2 | 9/2005 |
| WO | 2006/124874 A2 | 11/2006 |
| WO | 2007/05452 A1 | 5/2007 |
| WO | 2007/098507 A2 | 8/2007 |
| WO | 2007/146981 A2 | 12/2007 |
| WO | 2008/092049 A1 | 7/2008 |
| WO | 2008/092199 A1 | 8/2008 |
| WO | 2008/106635 A1 | 9/2008 |
| WO | 2008/124085 A2 | 10/2008 |
| WO | 2009/010794 A1 | 1/2009 |
| WO | 2009/080638 A2 | 7/2009 |
| WO | 2009/158571 A1 | 12/2009 |
| WO | 2010/011349 A2 | 1/2010 |
| WO | 2010/017122 A2 | 2/2010 |
| WO | 2010/118986 A1 | 10/2010 |
| WO | 2011/046970 A1 | 4/2011 |
| WO | 2011/093524 A1 | 8/2011 |
| WO | 2012/135641 A2 | 10/2012 |
| WO | 2012/135800 A1 | 10/2012 |
| WO | 2012/135801 A1 | 10/2012 |
| WO | 2013/064068 A1 | 5/2013 |
| WO | 2014/025128 A1 | 2/2014 |
| WO | 2014/025486 A1 | 2/2014 |
| WO | 2014/124230 A2 | 8/2014 |
| WO | 2014/130411 A1 | 8/2014 |
| WO | 2014/143659 A1 | 9/2014 |
| WO | 2014/152588 A1 | 9/2014 |
| WO | 2015/054572 A1 | 4/2015 |

OTHER PUBLICATIONS

Compound Summary for CID 69861127, PubChem, Dec. 23, 2015, 11 pages.
Compound Summary for CID 69898605, PubChem, Dec. 23, 2015, 11 pages.
Malani et al., "Synthesis, characterization and in vitro screening on bacterial, fungal and malarial strain of piprazinyl cyano biphenyl based compounds," *Bioorganic Chemistry* 51:16-23, 2013.
Zenkl et al., "Sugar-Responsive Fluorescent Nanospheres," *Macromol. Biosci.* 8:146-152, 2008.
Alessi et al., "Mechanism of Activation of Protein Kinase B by Insulin and IGF-1," *The EMBO Journal* 15(23):6541-6551, 1996.
Anderton et al., "Induction of Heart Valve Lesions by Small-Molecule ALK5 Inhibitors," *Toxicologic Pathology* 39(6):916-924, 2011.
Angelillo-Scherrer et al., "Role of Gas6 in Erythropoiesis and Anemia in Mice," *J. Chin. Invest.* 118(2):583-596, Feb. 2008.
Baxter et al. "Acquired mutation of the tyrosine kinase JAK2 in human myeloproliferative disorders," *Lancet* 365(9464):1054-1061, Mar. 2005.
Bellido-Martin et al., "Vitamin K-dependent actions of Gas6," *Vitam. Horm.* 78:185-209, 2008.
Bellosta et al., "Signaling Through the ARK Tyrosine Kinase Receptor Protects From Apoptosis in the Absence of Growth Stimulation," *Oncogene* 15:2387-2397, 1997.
Bellosta et al., "The Receptor Tyrosine Kinase ARK mediates Cell Aggregation by Homophilic Binding," *Molecular and Cellular Biology* 15(2):614-625, Feb. 1995.
Benekli et al., "Signal transducer and activator of transcription proteins in leukemias," *Blood* 101(8):2940-2954, Apr. 2003.
Blume-Jensen et al., "Oncogenic Kinase Signaling," *Nature* 411:355-365, 2001.
Braunger et al., "Intracellular Signaling of the Ufo/Axl Receptor Tyrosine Kinase Is Mediated Mainly by a Multi-Substrate Docking Site," *Oncogene* 14(22):2619-2631, 1997.

Fridell et al., "GAS 6 induces AXL-Mediated Chemotaxis of Vascular Smooth Muscle Cells," *The Journal of Biological Chemistry* 273:7123-7126, 1998.
Fruman et al., "*Xid*-like phenotypes: a B Cell Signalosome Takes Shape," *Immunity* 13(1):1-3, 2000.
Fry, "Phosphoinositide 3-kinase signalling in breast cancer: how big a role might it play?" *Breast Cancer Res.* 3:304-312, 2001.
Goldberg et al., "Rapid Generation of a High Quality Lead for Transforming Growth Factor-β (TGF-β) Type I Receptor (ALK5)," *J. Med. Chem.* 52:7901-7905, 2009.
Gould et al., "Gas6 Receptors Axl, Sky and Mer enhance platelet activation and regulate thrombotic responses," *Journal of Thrombosis and Haemostasis* 3(4):733-741, 2005.
Graham et al., "Cloning and mRNA Expression Analysis of a Novel Human Protooncogene, c-*mer*," *Cell Growth and Differentiation* 5:647-657, 1994.
Green et al., "Overexpression of the Axl tyrosine kinase receptor in cutaneous SCC-derived cell lines and tumours," *Journal of Cancer* 94:1446-1451, 2006.
Gura, "Systems for Identifying New Drugs are Often Faulty," *Science* 278(5340):1041-1042, 1997.
Hafizi et al., "Gas6 and protein S: Vitamin K-dependent ligands for the Axl receptor tyrosine kinase subfamily," *FEBS Journal* 273(23):5231-5244, 2006.
Hafizi et al., "Interaction of Axl receptor tyrosine kinase with C1-TEN, a novel C1 domain-containing protein with homology to tensin," *Biochemical and Biophysical Research Communications* 299:793-800, 2002.
Hafizi et al., "Signalling and functional diversity within the Axl subfamily of receptor tyrosinekinases," *Cytokine & Growth Factor Reviews* 17:295-304, 2006.
Hanada et al., "Structure, regulation and function PKB/AKT—a of major therapeutic target," *Biochimica et Biophysica Acta* 1697:3-16, 2004.
Hendriks, "Drug Discovery: New Btk inhibitor holds promise," *Nat. Chem. Biol.* 7(1):4-5, 2011.
Hubbard et al., "Protein Tyrosine Kinase Structure and Function," *Annual Review of Biochemistry* 69:377, 2000.
Hughes et al., "4-Aryl-5-cyano-2-aminopyrimidines as VEGF-R2 inhibitors: Synthesis and biological evaluation," *Bioorganic & Medicinal Chemistry Letters* 17:3266-3270, 2007.
James et al., "A unique clonal JAK2 mutation leading to constitutive signaling causes polycythaemia vera," *Nature* 434:1144-1148, Apr. 2005.
Johnson et al., "Relationships between drug activity in NCI preclinical in vitro and in vivo models and early clinical trials," *British Journal of Cancer* 84(10):1424-1431, 2001.
Keating et al., "Lymphoblastic leukemia/lymphoma in mice overexpressing the Mer (MerTK) receptor tyrosine kinase," *Oncogene* 25:6092-6100, 2006.
Korshunov et al. "Axl, A Receptor Tyrosine Kinase, Mediates Flow-induced Vascular Remodeling," *Circulation Research* 98:1446-1452, 2006.
Korshunov et al., "Axl Mediates Vascular Remodeling Induced by Deoxycorticosterone Acetate-Salt Hypertension," *Hypertension* 50:1057:1062, 2007.
Kurosaki, "Functional dissection of BCR signaling pathways," *Curr. Opin. Immunol.* 12:276-281, 2000.
Lemke et al., "Immunobiology of the TAM receptors," *Nature Reviews Immunology* 8:327-336, 2008.
Levine et al., "Activating mutation in the tyrosine kinase JAK2 in polycythemia vera, essential thrombocythemia, and myeloid metaplasia with myelofibrosis," *Cancer Cell* 7:387-397, Apr. 2005.
Li et al., "Axl as a potential therapeutic target in cancer: role of Axl in tumor growth, metastasis and angiogenesis," *Oncogene* 28:3442-3455, 2009.
Linger et al., "TAM receptor tyrosine kinases: biologic functions, signaling, and potential therapeutic targeting in human cancer," *Advanced Cancer Research* 100:35-83, 2008.
Manfioletti et al., "The protein encoded by a growth arrest-specific gene (gas6) is a new member of the vitamin K-dependent proteins related to protein S, a negative coregulator in the blood coagulation cascade," *Molecular and Cellular Biology* 13(8):4976-4985, 1993.

(56) References Cited

OTHER PUBLICATIONS

Manning et al., "Evolution of protein kinase signaling from yeast to man," *TRENDS in Biochemical Sciences* 27(10):514-520, 2002.

Mark et al., "*rse*, a Novel Receptor-type Tyrosine Kinase with Homology to Axl/Ufo, is Expressed at High Levels in the Brain," *Journal of Biological Chemistry* 269:10720-10728, 1994.

Mollard et al., "Design, Synthesis, and Biological Evaluation of a Series of Novel AXL Kinase Inhibitors," *ACS Medicinal Chemistry Letters* 2:907-912, 2011.

Pearce et al., "Chapter 18: Failure modes in anticancer drug discovery and development," *Cancer Drug Design and Discovery*:424-435, Elsevier, 2008.

Peeters et al., "Fusion of TEL, the ETS-Variant Gene 6 (ETV6), to the Receptor-Associated Kinase JAK2 as a Result of t(9; 12) in a Lymphoid and t(9; 15; 12) in a Myeloid Leukemia," *Blood* 90(7):2535-2540, Oct. 1997.

Reiter et al., "The t(8;9)(p22;p24) Is a Recurrent Abnormality in Chronic and Acute Leukemia that Fuses *PCM1* to *JAK2*," *Cancer Res.* 65(7):2662-2667, Apr. 2005.

Rescigno et al., "A putative receptor tyrosine kinase with unique structural topology," *Oncogene* 6(10):1909-1913, 1991.

Robinson et al., "The protein tyrosine kinase family of the human genome," *Oncogene* 19(49):5548-5557, 2000.

Rothlin et al., "TAM Receptors Are Pleiotropic Inhibitors of the Innate Immune Response," *Cell* 131:1124-1136, 2007.

Sainaghi et al., "Gas6 Induces Proliferation in Prostate Carcinoma Cell Lines Expressing the Axl Receptor," *Journal of Cell Physiology* 204(1):36-44, 2005.

Sawabu et al., "Growth Arrest-Specific Gene 6 and Axl Signaling Enhances Gastric Cancer Cell Survival Via Akt Pathway," *Mol. Carcinog.* 46(2):155-164, 2007.

Schaeffer et al., "Tec family kinases in lymphocyte signaling and function," *Curr. Opin. Immunol.* 12(3):282-288, 2000.

Shankar et al., "Gas6/Axl Signaling Activates the Phosphatidylinositol 3-Kinase/Akt1 Survival Pathway to Protect Oligodendrocytes from Tumor Necrosis Factor α-Induced Apoptosis," *The Journal of Neuroscience* 26(21):5638-5648, 2006.

Shannon et al., "JAKing up hematopoietic proliferation," *Cancer Cell* 7(4):291-293, Apr. 2005.

Sharif et al., "Twist mediates suppression of inflammation by type I IFNs and Axl," *The Journal of Experimental Medicine* 203(8):1891-1901, 2006.

Shieh et al., "Expression of Axl in Lung Adenocarcinoma and Correlation with Tumor Progression," *Neoplasia* 7(12):1058-1064, 2005.

Simone, "Part XI: Oncology: Introduction," *Cecil Textbook of Medicine, 20th Edition* 1:1004-1010, W.B. Saunders Company, Philadelphia,1996.

Sun et al., "Clinical implications of coexpression of growth arrest-specific gene 6 and receptor tyrosine kinases Axl and Sky in human uterine leiomyoma," *Molecular Human Reproduction* 9(11):701-707, 2003.

Takemoto et al., "Proliferation of adult T cell leukemia/lymphoma cells is associated with the constitutive activation of JAK/STAT proteins," *Proc. Natl. Acad. Sci. USA* 94:13897-13902 Dec. 1997.

Traxler, "Protein tyrosine kinase inhibitors in cancer treatment," *Exp. Opin. Ther. Patents* 7(6):571-588, 1997.

Ulrich, "Crystallization—4 Crystal Characteristics," *Kirk-Othmer Encyclopedia of Chemical Technology*:3-26, 2002.

Vajkoczy et al., "Dominant-negative inhibition of the Axl receptor tyrosine kinase suppresses brain tumor cell growth and invasion and prolongs survival," *PNAS* 103(15):5799-5804, Apr. 2006.

Vippagunta et al., "Crystalline solids," *Advanced Drug Delivery Reviews* 48:3-26, 2001.

Walz et al., "Activated Jak2 with the V617F Point Mutation Promotes $G_1$/S Phase Transition," *J. Biol. Chem.* 281(26):18177-18183, Jun. 2006.

Ahn et al., "Synthesis and Antiproliferative Activity of Pyridinylcarbonylpyrimidines Against Melanoma Cell Line," *Bull. Korean Chem. Soc.* 32(4):1209-1214, 2011.

Barlaam et al., "Inhibitors of the tyrosine kinase EphB4. Part 4: Discovery and optimization of a benzylic alcohol series," *Bioorganic & Medicinal Chemistry Letters* 21:2207-2211, 2011.

Buchanan et al., "Discovery of 2,4-bis-arylamino-1,3-pyrimidines as insulin-like growth factor-1 receptor (IFG-1R) inhibitors," *Bioorganic & Medicinal Chemistry Letters* 21:2394-2399, 2011.

Choi et al., "Design and synthesis of 7*H*-pyrrolo[2,3-*d*]pyrimidines as focal adhesion kinase inhibitors. Part 1" *Bioorganic & Medicinal Chemistry Letters* 16:2173-2176, 2006.

CAS Registry No. 1251954-86-5, "Benzamide, 3-[[4-[(2-amino-3-flurophenyl)amino]-5-chloro-2-pyrimidinyl]amino]-N-ethyl-4-fluoro-," Nov. 9, 2010, 11 pages.

CAS Registry No. 1192474-26-2, "Benzeneethanol, 3-bromo-5-[[5-chloro-4-[(3-hydroxyphenyl)amino]-2-pyrimidinyl]amino]-," Feb. 7, 2010, 67 pages.

Breslin et al., "Design, Synthesis, and Anaplastic Lymphoma Kinase (ALK) Inhibitory Activity for a Novel Series of 2,4,8,22-Tetraazatetracyclo[14.3.1.1$^{3,7}$.1$^{9,13}$]-docosa-1(20),3(22),4,6,9(21),10,12,16,18-nonaene Macrocycles," *Journal of Medicinal Chemistry* 55:449-464, 2012.

CAS Registry No. 794466-29-8, "2,4-Pyrimidinediamine, 5-bromo-N4-[2-(4-morpholinyl)phenyl]-N2-(3,4,5-trimethoxyphenyl)-," Dec. 8, 2004, 1 page.

CAS Registry No. 698998-35-5, "2,4-Pyrimidinediamine, 5-bromo-N2-(3,4-dimethoxyphenyl)-N4-[4-(1H-pyrazol-3-yl)phenyl]-," Jun. 25, 2004, 1 page.

JAK2 AND ALK2 INHIBITORS AND METHODS FOR THEIR USE

CROSS-REFERENCE TO RELATED APPLICATION

This application claims benefit under 35 U.S.C. § 119(e) of U.S. Provisional Patent Application No. 61/785,460, filed Mar. 14, 2013, which is incorporated herein by reference in its entirety.

BACKGROUND OF THE INVENTION

Field of the Invention

The present invention is generally directed to novel compounds having activity as inhibitors of ALK2 and/or JAK2 kinases and use of the same for treatment of various cancers.

Description of the Related Art

The Janus kinases (JAKs) are a family of kinases of which there are four in mammals (JAK1, JAK2, JAK3 and TYK2) that are integral in signaling from extracellular cytokines, including the interleukins, interferons, as well as numerous hormones (Aringer, M., et al., Life Sci, 1999. 64(24): p. 2173-86; Briscoe, J., et al., Philos Trans R Soc Lond B Biol Sci, 1996. 351(1336): p. 167-71; Ihle, J. N., Semin Immunol, 1995. 7(4): p. 247-54; Ihle, J. N., Philos Trans R Soc Lond B Biol Sci, 1996. 351(1336): p. 159-66; Firmbach-Kraft, I., et al., Oncogene, 1990. 5(9): p. 1329-36; Harpur, A. G., et al., Oncogene, 1992. 7(7): p. 1347-53; Rane, S. G. and E. P. Reddy, Oncogene, 1994. 9(8): p. 2415-23; Wilks, A. F., Methods Enzymol, 1991. 200: p. 533-46). These non-receptor tyrosine kinases associate with various cytokine receptors and act to transduce the signal from extracellular ligand-receptor binding into the cytoplasm, by phosphorylating STAT (signal transducer and activator of transcription) molecules, which then enter the nucleus and direct transcription of various target genes involved in growth and proliferation (Briscoe, J., et al.; Ihle, J. N. (1995); Ihle, J. N. (1996); Rawlings, J. S., K. M. Rosier and D. A. Harrison, J Cell Sci, 2004. 117(Pt 8): p. 1281-3.). The four JAK isoforms transduce different signals by being associated specifically with certain cytokine receptors, and activating a subset of downstream genes. For example, JAK2 associates with cytokine receptors specific for interleukin-3 (Silvennoinen, O., et al., Proc Natl Acad Sci USA, 1993. 90(18): p. 8429-33), erythropoietin (Witthuhn, B. A., et al., Cell, 1993. 74(2): p. 227-36), granulocyte colony stimulating factor (Nicholson, S. E., et al., Proc Natl Acad Sci USA, 1994. 91(8): p. 2985-8), and growth hormone (Argetsinger, L. S., et al., Cell, 1993. 74(2): p. 237-44).

The JAK family of enzymes has become a set of targets for various hematological and immunological disorders. JAK2 is currently under study as a viable target for neoplastic disease, especially leukemias and lymphomas (Benekli, M., et al., Blood, 2003. 101(8): p. 2940-54; Peeters, P., et al., Blood, 1997. 90(7): p. 2535-40; Reiter, A., et al., Cancer Res, 2005. 65(7): p. 2662-7; Takemoto, S., et al., Proc Natl Acad Sci USA, 1997. 94(25): p. 13897-902) as well as solid tumors (Walz, C., et al., J Biol Chem, 2006. 281(26): p. 18177-83), and other myeloproliferative disorders such as polycythemia vera (Baxter, E. J., et al., Lancet, 2005. 365(9464): p. 1054-61; James, C., et al., Nature, 2005. 434(7037): p. 1144-8; Levine, R. L., et al., Cancer Cell, 2005. 7(4): p. 387-97; Shannon, K. and R. A. Van Etten, Cancer Cell, 2005. 7(4): p. 291-3), due to its activation of downstream effector genes involved in proliferation. Because of its association with, and deregulation in, neoplastic and myeloproliferative disorders, small molecule JAK2 inhibitors for the treatment of human malignancies are of significant interest.

Bone morphogenetic proteins (BMPs) are pleiotropic growth factors playing essential roles in coordinating tissue architecture throughout various organs in the body. BMP ligands interact with bone morphogenetic protein receptors (BMPRs), which belong to the transforming growth factor beta (TGF-b) superfamily of serine/threonine kinase receptors (Ikushima, H. and K. Miyazono, Biology of Transforming Growth Factor-beta Signalin. Curr Pharm Biotechnol, 2011). The ligands bind to type-II receptors, which then recruit type-I receptors forming a heteromeric complex. As a complex, the type-II receptor phosphorylates the type-I receptor, which allows the type-I receptor to become active and phosphorylate downstream signaling molecules. The downstream effects of activating these receptors are primarily carried out by the SMAD family of proteins. SMADs become phosporylated and transduce the signal from the cell membrane to the nucleus where they function as transcription factors to regulated gene expression (Massague, J., J. Seoane, and D. Wotton, Smad transcription factors. Genes Dev, 2005. 19(23): p. 2783-810).

In individuals with chronic diseases, such as cancer and inflammation, BMP signaling is constitutively activated leading to anemia. This condition is commonly referred to as anemia of chronic disease (ACD) and is a debilitating symptom associated with cancer patients (Cullis, J. O., Diagnosis and management of anaemia of chronic disease: current status. Br J Haematol, 2011. 154(3): p. 289-300). Chronic anemia in cancer patients leads to extreme weakness and fatigue, which leads to a poor quality of life for these individuals. In these patients, BMP signaling through two BMP type-I receptors, ALK2 (also known as ACVR1) and ALK3 induces the hepatic expression of the peptide hormone, called hepcidin (Steinbicker, A. U., et al., Perturbation of hepcidin expression by BMP type I receptor deletion induces iron overload in mice. Blood, 2011. 118 (15): p. 4224-30). Hepcidin reduces serum iron levels by promoting the degradation of the iron exporter, ferroportin, resulting in the increase of iron stored away in macrophages and other cell types and making the iron unavailable for hemoglobin and red blood cell (RBC) function. Supplementing a patient's intake of iron does not reverse ACD because the ingested iron simply is stored away due to the activated BMP pathway and high serum hepcidin levels. Currently, ACD in cancer is managed by limiting the physical activity of patients and blood transfusions are used in the most severe cases Inhibition of BMP signaling in these patients has the potential to provide a real difference in their quality of life and ultimately, may positively impact how they respond to therapy, radiation, or surgery (Steinbicker, A. U., et al., Inhibition of bone morphogenetic protein signaling attenuates anemia associated with inflammation. Blood, 2011. 117(18): p. 4915-23; Coyne, D. W., Hepcidin: clinical utility as a diagnostic tool and therapeutic target. Kidney Int, 2011. 80(3): p. 240-4; Theurl, I., et al., Pharmacologic inhibition of hepcidin expression reverses anemia of chronic disease in rats. Blood, 2011).

In addition to its function in ACD, BMP signaling plays pivotal roles in the growth and metastasis of cancer cells, particularly in breast, prostate, and other cancers that frequently metastasize to the bone (Ye, L., M. D. Mason, and W. G. Jiang, Bone morphogenetic protein and bone metastasis, implication and therapeutic potential. Front Biosci, 2011. 16: p. 865-97). BMPs and BMPRs are more highly expressed in metastatic breast cancer cells compared to less metastatic ones and also in prostate cancer cells that generate osteosclerotic bone metastases (Bobinac, D., et al., Expression of bone morphogenetic proteins in human meta-

*static prostate and breast cancer*. Croat Med J, 2005. 46(3): p. 389-96). In addition to effecting the invasiveness and metastasis of cancer cells, the BMP pathway has also been shown to influence the bone microenvironment. The cross-communication between cancer cells and the bone microenvironment via the BMP signaling pathway promotes the metastasis of the cancer cells to the bone. Studies have shown that the inhibition of BMP signaling significantly reduces bone tumor burden and osteolytic disease in a preclinical model of prostate cancer bone metastasis. These results suggest that a BMP inhibitor may have application in preventing bone metastases in addition to its activity against anemia induced by chronic disease.

Furthermore, a BMP inhibitor has the potential to treat multiple disease indications outside of cancer. ACD is a devastating condition that affects individuals suffering from other diseases, including rheumatoid arthritis, systemic lupus, chronic kidney disease, and many other inflammatory diseases. Additionally, a rare childhood genetic disease, called fibrodysplasia ossificans progressive (FOP) has been shown to be caused by activating mutations in the alk2 gene (Kaplan, F. S., et al., *Investigations of activated ACVR1/ALK2, a bone morphogenetic protein type I receptor, that causes fibrodysplasia ossificans progressiva*. Methods Enzymol, 2010. 484: p. 357-73). The mutation in ALK2 in this disease causes fibrous tissue (muscle, tendon, ligament, etc.) to be ossified when damaged. In other words, when patients with this condition experience injury to muscle or joint tissues, the repaired tissue is converted to bone causing joints to be permanently frozen in place. By the teenage years, these children have lost most of the function of their joints. Studies performed in animal models of FOP suggest that inhibiting ALK2 decreases the "flare-ups" associated with FOP and prevents the ossification of repaired tissue in the model. The medical and commercial benefits of a BMP inhibitor (i.e. ALK2) are quite broad and extend to multiple indications outside of cancer.

While progress has been made in this field, there is a need for the design of specific and selective inhibitors for the treatment of cancer and other conditions that are mediated and/or associated with ALK2 and/or JAK2 (including JAK2 V617F) protein kinases. The present invention fulfills these needs and offers other related advantages.

BRIEF SUMMARY OF THE INVENTION

In brief, the present invention is directed to compounds having activity as ALK2 and/or JAK2 kinase inhibitors, including stereoisomers, tautomers pharmaceutically acceptable salts and prodrugs thereof, and the use of such compounds for treatment of various cancers.

In one embodiment, compounds having the following structure (I) are provided:

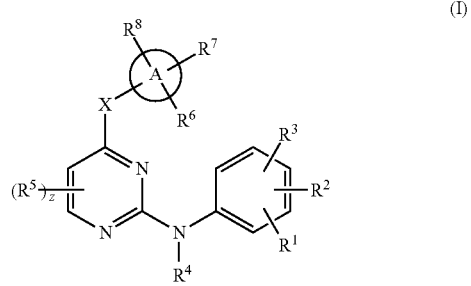

or a stereoisomer, pharmaceutically acceptable salt, tautomer or prodrug thereof, wherein X, A, z, $R^1$, $R^2$, $R^3$, $R^4$, $R^5$, $R^6$, $R^7$ and $R^8$ are as defined herein.

In another embodiment, a pharmaceutical composition is provided comprising a compound having structure (I), or a stereoisomer, pharmaceutically acceptable salt, tautomer or prodrug thereof, and a pharmaceutically acceptable carrier, diluent or excipient. In some embodiments, the invention is directed to use of the pharmaceutical composition for inhibiting ALK2 and/or JAK2 kinases in a mammal.

In another embodiment, a method for inhibiting ALK2 and/or JAK2 kinase in a mammal in need thereof is provided, the method comprising administering to the mammal an effective amount of a compound having structure (I), or a stereoisomer, pharmaceutically acceptable salt, tautomer or prodrug thereof. In some embodiments the method is for treatment of cancer. In other embodiments, the method is for treatment of anemia and/or anemia related conditions.

Use of a compound of structure (I) for treatment of ALK2 and/or JAK2 kinase-related conditions, such as cancer, is also provided. In other embodiments, the use is for treatment of anemia and/or anemia related conditions.

These and other aspects of the invention will be apparent upon reference to the following detailed description.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION OF THE INVENTION

Figure 1:
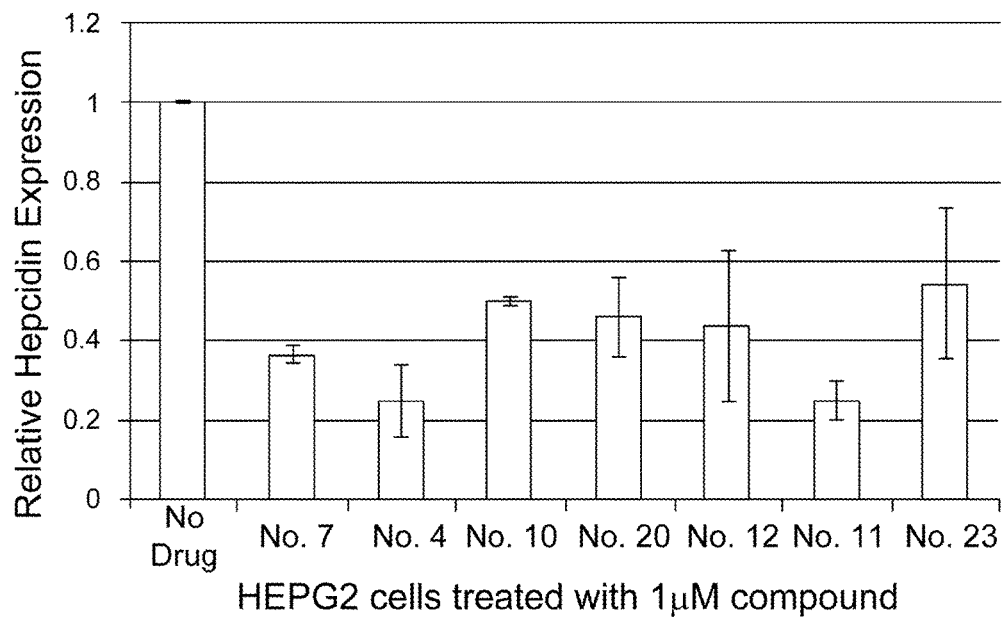
FIG. 1 presents hepcidin expression data.

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising"

are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

I. Definitions

"Amino" refers to the —$NH_2$ radical.
"Cyano" or "nitrile" refers to the —CN radical.
"Hydroxy" or "hydroxyl" refers to the —OH radical.
"Imino" refers to the =NH substituent.
"Nitro" refers to the —$NO_2$ radical.
"Oxo" refers to the =O substituent.
"Thioxo" refers to the =S substituent.
"Alkyl" refers to a straight or branched hydrocarbon chain radical consisting solely of carbon and hydrogen atoms, which is saturated or unsaturated (i.e., contains one or more double (alkenyl) and/or triple (alkynyl) bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. An alkyl comprising one or more carbob-carbon double bonds is an alkenyl. An alkyl comprising one or more carbon-carbon triple bonds is an alkynyl. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group may be optionally substituted.

"Alkoxyalkyl" refers to a radical of the formula —$R_bOR_a$ where $R_a$ is an alkyl radical as defined above containing one to twelve carbon atoms and $R_b$ is an alkylene radical as defined above. Unless stated otherwise specifically in the specification, an alkoxyalkyl group may be optionally substituted.

"Alkylamino" refers to a radical of the formula —$NHR_a$ or —$NR_aR_a$ where each $R_a$ is, independently, an alkyl radical as defined above containing one to twelve carbon atoms. Unless stated otherwise specifically in the specification, an alkylamino group may be optionally substituted.

"Alkylaminoalkyl" refers to a radical of the formula —$R_bNHR_a$ or —$NR_aR_a$ where each $R_a$ is, independently, an alkyl radical as defined above containing one to twelve carbon atoms and $R_b$ is an alkylene radical as defined above. Unless stated otherwise specifically in the specification, an alkylaminoalkyl group may be optionally substituted.

"Alkylsulfone" refers to a radical of the formula —$S(O)2R_a$ where $R_a$ is an alkyl radical as defined above containing one to twelve carbon atoms and $R_b$ is an alkylene radical as defined above. Unless stated otherwise specifically in the specification, an alkylsulfone group may be optionally substituted.

"Hydroxylalkyl" refers an alkyl radical as defined above containing one to twelve carbon atoms which has been substituted by one or more hydroxyl groups. Unless stated otherwise specifically in the specification, hydroxylalkyl group may be optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_e$ where $R_b$ is an alkylene chain as defined above and $R_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —$R_bR_d$ where $R_b$ is an alkylene chain as defined above and $R_d$ is a cycloalkyl radical as defined above. Unless stated otherwise specifically in the specification, a cycloalkylalkyl group may be optionally substituted.

"Cycloalkoxy" refers to a radical of the formula —$OR_a$ where $R_a$ is a cycloalkyl radical as defined above. Unless stated otherwise specifically in the specification, a cycloalkoxy group may be optionally substituted.

"Cycloalkoxyalkyl" refers to a radical of the formula —$R_bOR_a$ where $R_a$ is a cycloalkyl radical as defined above and $R_b$ is an alkyl radical as defined above containing one to twelve carbon atoms. Unless stated otherwise specifically in the specification, an cycloalkoxyalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —$R_bR_e$ where $R_b$ is an alkylene chain as defined above and $R_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group may be optionally substituted.

"Nitrilylalkyl" is an alkyl as defined above which comprises one or more —CN substitutions. Unless stated otherwise specifically in the specification, a nitrilylalkyl group may be optionally substituted.

"Nitrilylcycloalkyl" is a cycloalkyl as defined above which comprises one or more —CN substitutions. Unless stated otherwise specifically in the specification, a nitrilylcycloalkyl group may be optionally substituted.

"Nitrilylcycloalkylalkyl" refers to a radical of the formula —$R_bR_d$ where $R_b$ is an alkylene chain as defined above and $R_d$ is a nitrilylcycloalkyl radical as defined above. Unless stated otherwise specifically in the specification, a nitrilylcycloalkylalkyl group may be optionally substituted.

"Amino acid ester" refers to an amino acid having an ester group in place of the acid group. Unless stated otherwise specifically in the specification, an amino acid esterl group may be optionally substituted.

The term "substituted" used herein means any of the above groups (i.e., alkyl, alkylene, alkoxy, alkoxyalkyl, alkylamino, alkylaminoalkyl, alkylsulfone, hydroxylalkyl, thioalkyl, aryl, aralkyl, cycloalkyl, cycloalkylalkyl, cycloalkoxy, cycloalkoxyalkyl, haloalkyl, heterocyclyl, N-heterocyclyl, heterocyclylalkyl, heteroaryl, N-heteroaryl, heteroarylalkyl, nitrilylalkyl, nitrilylcycloalkyl, nitrilylcycloalkylalkyl and/or amino acid ester) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, alkylamino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively.

Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labelled compounds of structure (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a compound of the invention which, when administered to a mammal, preferably a human, is sufficient to effect treatment, as defined below, of cancer in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts or tautomers may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule, for example, the conversion of a ketone to an enol via a proton shift. The present invention includes tautomers of any said compounds.

A "chemotherapeutic agent" is a chemical which eradicates, stops or slows the growth of cancer cells.

II. Compounds

As noted above, in one embodiment of the present invention compounds having activity as ALK2 and/or JAK2 kinase inhibitors are provided, the compounds having the following structure (I):

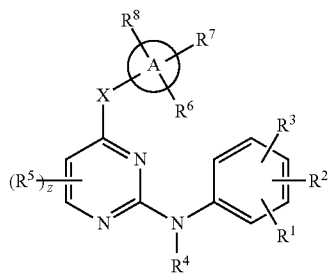

or a stereoisomer, pharmaceutically acceptable salt, tautomer or prodrug thereof,
wherein:
A represents a 6-membered aromatic ring or a 5 or 6-membered heteroaryl ring;
X is —NH—, —O—, —S(O)$_m$—, —CH$_2$—, —CHOH— or —C(=O)—;
$R^1$ is H, halo, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —S(O)$_m$ $C_1$-$C_6$ alkyl, $C_1$-$C_6$ hydroxylalkyl, —OCH$_2$CH$_2$R$^9$, —(CH$_2$)$_n$NR$^a$R$^b$, or —CONR$^a$R$^b$;
$R^2$ is halo, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —S(O)$_m$ $C_1$-$C_6$ alkyl, $C_1$-$C_6$ hydroxylalkyl, —OCH$_2$CH$_2$R$^9$, —(CH$_2$)$_n$NR$^a$R$^b$, or —CONR$^a$R$^b$;
$R^3$ is halo, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, —S(O)$_m$ $C_1$-$C_6$ alkyl, $C_1$-$C_6$ hydroxylalkyl, —OCH$_2$CH$_2$R$^9$, —(CH$_2$)$_n$NR$^a$R$^b$, —CONR$^a$R$^b$ or —NHCHR$^a$R$^b$;
$R^4$ is H or $C_1$-$C_6$ alkyl;
$R^5$ is, at each occurrence, independently H, halo, $C_1$-$C_6$ alkyl, $C_1$-$C_6$ alkoxy, $C_3$-$C_6$ cycloalkoxy, —CN, $C_1$-$C_6$ nitrilylalkyl or $C_3$-$C_6$ nitrilylcycloalkyl;
$R^6$ and $R^7$ are each independently H, halo, hydroxyl, $C_1$-$C_6$ alkyl, $C_1$-$C_6$ alkoxy, $C_3$-$C_6$ cycloalkoxy, $C_1$-$C_6$ nitrilylalkyl, $C_3$-$C_6$ nitrilylcycloalkyl, $C_3$-$C_6$ nitrilylcycloalkylalkyl or —(CH$_2$)$_n$NR$^a$R$^b$;
$R^8$ is H, halo, hydroxyl, $C_1$-$C_6$ alkyl, $C_1$-$C_6$ alkoxy, $C_3$-$C_6$ cycloalkoxy, $C_1$-$C_6$ nitrilylalkyl, $C_3$-$C_6$ nitrilylcycloalkyl, $C_3$-$C_6$ nitrilylcycloalkylalkyl, —(CH$_2$)$_n$NR$^a$R$^b$, aryl or heteroaryl;
$R^9$ is —H, —F, —Cl, $C_1$-$C_4$ alkyl, $C_2$-$C_3$ alkenyl, $C_2$-$C_3$ alkynyl, $C_3$-$C_4$ cycloalkyl, —CH$_2$OH, —OCH$_3$, —OCH$_2$CH$_3$, —S(O)$_m$CH$_3$, —CH$_2$CN, —CH$_2$OCH$_3$, —CH$_2$S(O)$_m$CH$_3$, —CN, —CHCH$_3$CN, —C(CH$_3$)$_2$CN or

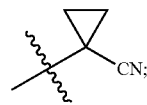 [SMILES: *C1(C#N)CC1]

$R^a$ and $R^b$ are each independently —H, $C_1$-$C_6$ alkyl, $C_1$-$C_6$ hydroxylakly, or $R^a$ and $R^b$ together with the nitrogen or carbon atom to which they are attached form an optionally substituted 5 or 6 membered saturated carbocyclic or heterocyclic ring;
m is 0, 1 or 2; and
n is 0, 1, 2 or 3.

In certain embodiments of compound (I), $R^5$ is not H or neither of $R^6$ or $R^7$ is —CH$_2$CN when X is NH and one of $R^1$, $R^2$ or $R^3$ is 4-methylpiperazin-1-yl and another of $R^1$, $R^2$ or $R^3$ is F.

In other embodiments of compound (I):
either $R^5$ is not H or none of $R^6$, $R^7$ or $R^8$ are —CH$_2$CN when X is NH, A is a 6-membered aromatic ring and one of $R^1$, $R^2$ or $R^3$ is 4-methylpiperazin-1-yl and another of $R^1$, $R^2$ or $R^3$ is F or CF$_3$; and
$C_1$-$C_6$alkoxy is not substituted with heterocyclyl.

In still more embodiments, z is 1 and $R^5$ is H, halo, $C_1$-$C_6$ alkyl, $C_1$-$C_6$ alkoxy, $C_3$-$C_6$ cycloalkoxy or —CN.

In this regard, it is understood that embodiments which include one or more of the foregoing provisos do not include the specific compounds disclosed in PCT Pub. No. WO 2008/106635.

In other embodiments of compound (I), $R^8$ is a heteroaryl selected from pyridyl, pyrrolyl and thiazolyl.

In certain other embodiments of the foregoing, the compound has the following structure (II):

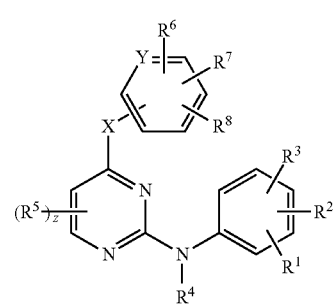

wherein:
X is —NH—;
Y is N or CH;
$R^1$ is H or $C_1$-$C_6$ alkoxy;
$R^2$ is halo or $C_1$-$C_6$ alkoxy;
$R^3$ is $C_1$-$C_6$ alkoxy or —NHCHR$^a$R$^b$;

$R^4$ is H;

$R^5$ is, at each occurrence, independently H, halo, $C_1$-$C_6$ alkyl, $C_1$-$C_6$ alkoxy, —CN or $C_1$-$C_6$ nitrilylalkyl;

$R^6$ and $R^7$ are each independently H, halo, $C_1$-$C_6$ alkyl, $C_1$-$C_6$ nitrilylalkyl, $C_3$-$C_6$ nitrilylcycloalky;

$R^8$ is H or heteroaryl; and z is 0, 1 or 2.

In some embodiments of the compound of structure (II) $R^6$ is H, $C_1$-$C_6$ alkyl, $C_1$-$C_6$ nitrilylalkyl, $C_3$-$C_6$ nitrilylcycloalkyl and $R^7$ is H, halo, $C_1$-$C_6$ alkyl, $C_1$-$C_6$ nitrilylalkyl or $C_3$-$C_6$ nitrilylcycloalky.

In some other embodiments of the compound of structure (II), $R^5$ is H, halo, $C_1$-$C_6$ alkyl, $C_1$-$C_6$ alkoxy or —CN. In some of these embodiments, z is 0.

In certain embodiments $R^8$ is a heteroaryl selected from pyridinyl, pyrrolyl and thiazolyl.

In other embodiments of the foregoing, X is —NH—. In more embodiments, Y is CH. In some more embodiments Y is N.

In yet other embodiments of the foregoing compounds of structure (I) or (II), $R^1$ is H. In some different embodiments $R^1$ is $C_1$-$C_6$ alkoxy. In other embodiments, $R^1$ is methoxy.

In some other embodiments, $R^1$ and $R^2$ are each $C_1$-$C_6$alkoxy. For example, in some embodiments $R^1$ and $R^2$ are each methoxy.

In some other embodiments, $R^1$, $R^2$ and $R^3$ are each $C_1$-$C_6$alkoxy. For example, in some embodiments $R^1$, $R^2$ and $R^3$ are each methoxy.

In still other embodiments of any of the foregoing compounds of structure (I) or (II), $R^2$ is halo. For example, in some embodiments $R^2$ is F or Cl. In other embodiments, $R^2$ is $C_1$-$C_6$ alkoxy. For example, in some embodiments $R^2$ is methoxy.

In more embodiments of the foregoing compounds of structure (I) or (II), $R^3$ is —NHCHR$^a$R$^b$ and R$^a$ and R$^b$ join to form a heterocyclic ring. In some embodiments, the heterocyclic ring is a substituted or unsubstituted piperazinyl ring. For example, in some embodiments the substituted piperizinyl ring is an N-substituted piperizinyl ring, and the substituted is selected from $C_1$-$C_6$ alkly, $C_1$-$C_6$ carboxyalkylcarbonyl and $C_1$-$C_6$ hydroxylalkyl. In certain embodiments compounds wherein $R^3$ is unsubstituted piperazin-1-yl are excluded.

In more embodiments $R^3$ is —NHCHR$^a$R$^b$ and R$^a$ and R$^b$ join to form a heterocyclic ring and one or more of $R^1$ and $R^2$ are $C_1$-$C_6$alkoxy. For example, in some embodiments, $R^3$ is piperazinyl and $R^1$ is $C_1$-$C_6$alkoxy, for example methoxy. In certain embodiments the piperazinyl is N-methylpiperazinyl. In further embodiments of the foregoing, $R^2$ is H.

In still other embodiments of any of the foregoing compounds of structure (I) or (II), $R^3$ is $C_1$-$C_6$ alkoxy. For example, in some embodiments $R^3$ is methoxy.

In other embodiments of any of the foregoing compounds, the compound has one of the following structures:

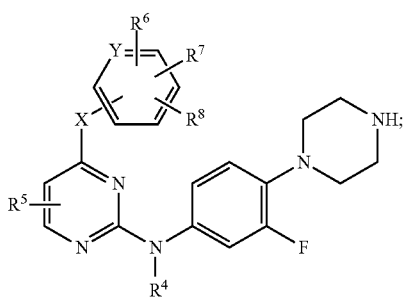

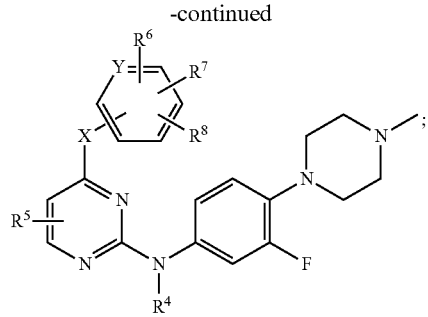

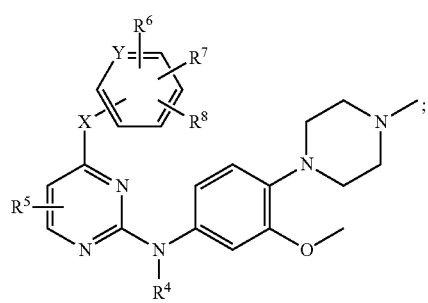

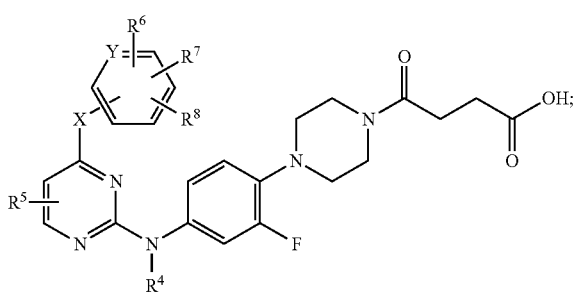

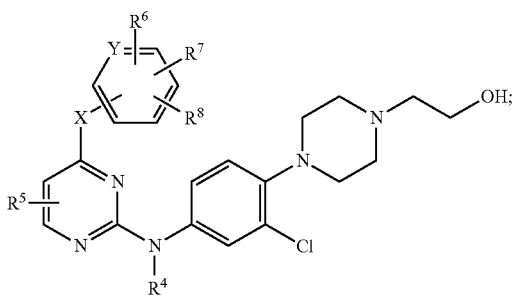

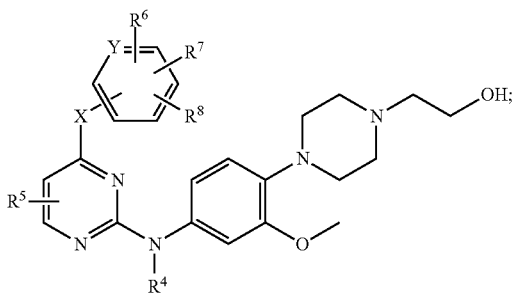

-continued

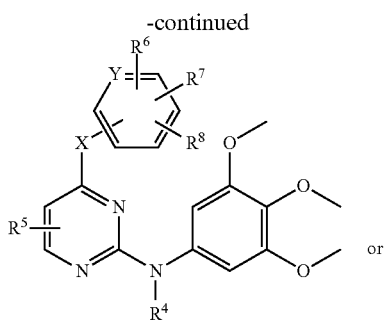

or

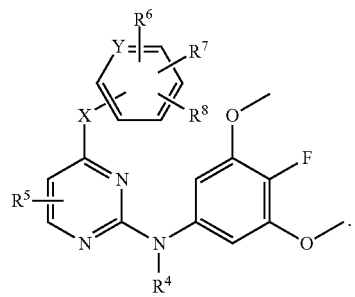

In certain of the above embodiments, $R^5$ is H. In other embodiments $R^5$ is methyl. In more embodiments, $R^5$ is chloro or fluoroIn yet more embodiments, $R^5$ is nitrilyl. In other aspects, $R^5$ is methoxy.

In yet other embodiments of the foregoing compounds of structure (I) or (II), at least one of $R^6$ and $R^7$ is H.

In more embodiments of any of the foregoing compounds of structure (I) or (II), at least one of $R^6$ or $R^7$ is fluoro or chloro.

In other embodiments of any of the foregoing compounds of structure (I) or (II), at least one of $R^6$ or $R^7$ is $C_1$-$C_6$ alkyl. For example, in some embodiments the $C_1$-$C_6$ alkyl is methyl.

In still more other embodiments of the foregoing compounds of structure (I) or (II), one of $R^6$ or $R^7$ is $C_1$-$C_6$ nitrilylalkyl. For example, in some embodiments the $C_1$-$C_6$ nitrilylalkyl is —$CH_2CN$. In some of these embodiments, $R^3$ is piperazinyl. In further embodiments, $R^2$ is halo, such as chloro or fluoro, and $R^1$ is H. It still other of these embodiments, $R^3$ is piperazinyl, $R^2$ is $C_1$-$C_6$alkoxy, such as methoxy, and $R^1$ is H.

In yet other embodiments of the foregoing compounds of structure (I) or (II), $R^6$ or $R^7$ is $C_3$-$C_6$ nitrilylcycloalky. For example, in certain embodiments the $C_3$-$C_6$ nitrilylcycloalky is

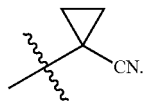

In some other embodiments, A is phenyl, $R^6$ is $C_3$-$C_6$ nitrilylcycloalky and $R^2$ is $C_1$-$C_6$alkoxy. In further embodiments of the foregoing, $R^3$ is piperazinyl and $R^1$ is H.

In some other embodiments, A is phenyl, $R^6$ is $C_3$-$C_6$ nitrilylcycloalky and $R^2$ is halo, such as fluoro or chloro. In further embodiments of the foregoing, $R^3$ is piperazinyl and $R^1$ is H.

In some other embodiments, A is phenyl, $R^6$ is $C_3$-$C_6$ nitrilylcycloalky and $R^2$ is $C_1$-$C_6$alkoxy, such as methoxy. In further embodiments of the foregoing, $R^3$ and $R^1$ are each $C^1$-$C^6$alkoxy, such as methoxy.

In some embodiments, $R^8$ is H. In other embodiments, $R^8$ is heteroaryl.

For example in some embodiments the heteroaryl is substituted or unsubstituted pyridinyl. In some of these embodiments A is heteroaryl, such as pyridinyl. In even other embodiments, A is pyridinyl, $R^8$ is pyridinyl and one or more, for example each, of $R^1$, $R^2$ or $R^3$ is $C_1$-$C_6$alkoxy, such as methoxy.

In various embodiments of the foregoing, the compound has one of the following structures:

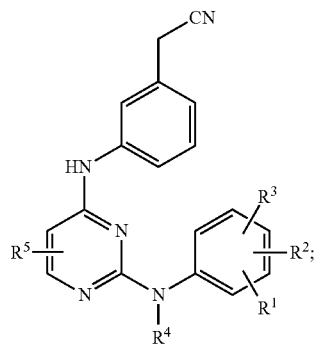

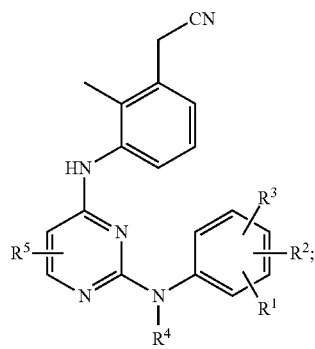

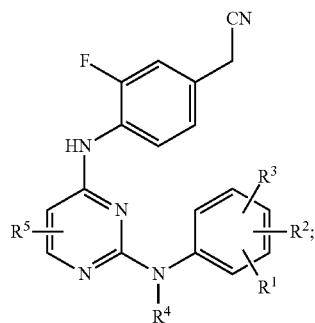

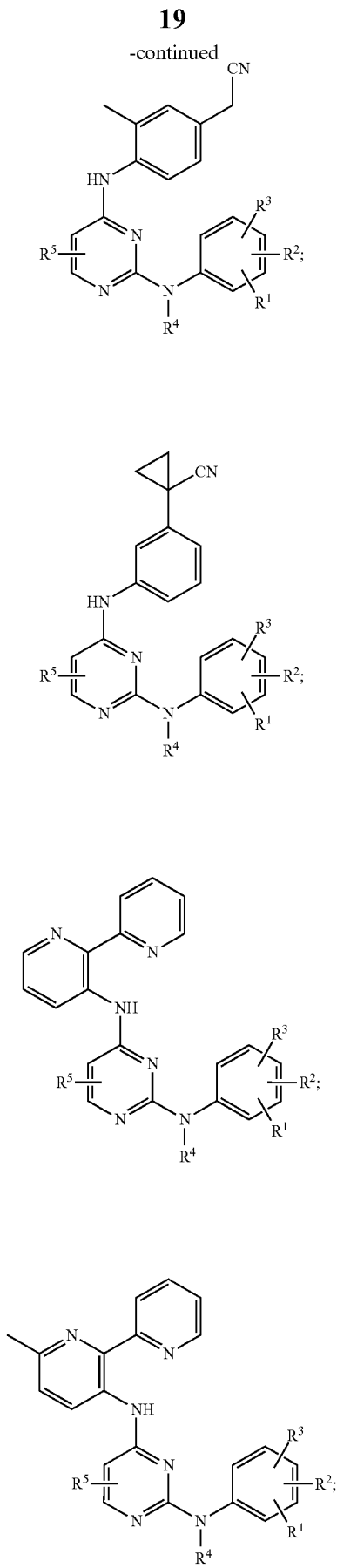
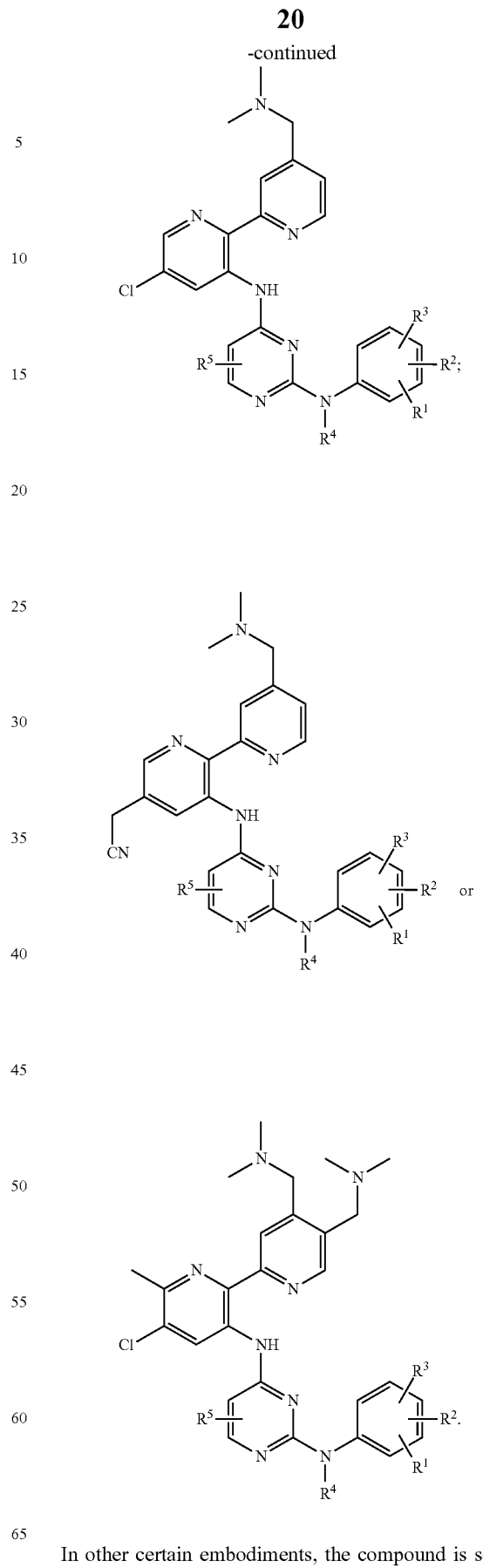
In other certain embodiments, the compound is selected from a compound in Table 1.

TABLE 1

| | Exemplary Compounds | Activity* | |
|---|---|---|---|
| No. | Structure | JAK2 | ALK2 |
| 1 | (structure) | + | + |
| 2 | (structure) | + | + |
| 3 | (structure) | + | + |
| 4 | (structure) | +++ | ++ |

TABLE 1-continued

Exemplary Compounds

| No. | Structure | Activity* JAK2 | ALK2 |
|---|---|---|---|
| 5 | 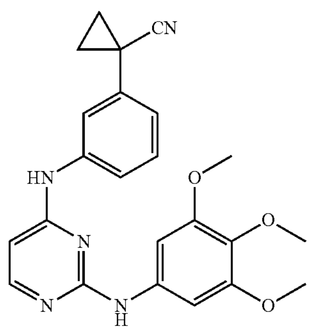 [SMILES: COc1cc(Nc2nccc(Nc3cccc(C4(C#N)CC4)c3)n2)cc(OC)c1OC] | +++ | + |
| 6 | 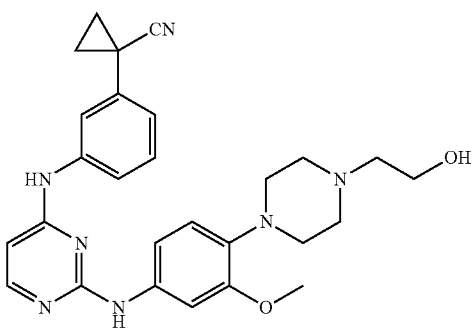 [SMILES: COc1cc(Nc2nccc(Nc3cccc(C4(C#N)CC4)c3)n2)ccc1N1CCN(CCO)CC1] | N/D | N/D |
| 7 | 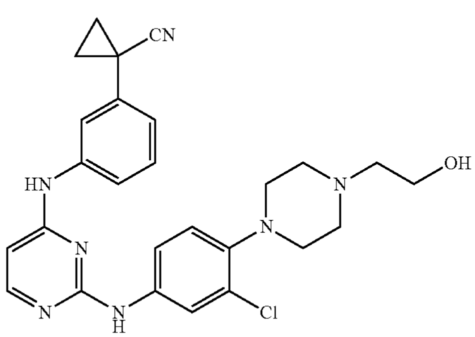 [SMILES: N#CC1(c2cccc(Nc3ccnc(Nc4ccc(N5CCN(CCO)CC5)c(Cl)c4)n3)c2)CC1] | +++ | ++ |
| 8 | 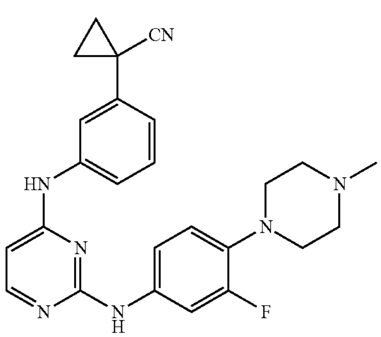 [SMILES: CN1CCN(c2ccc(Nc3nccc(Nc4cccc(C5(C#N)CC5)c4)n3)cc2F)CC1] | +++ | ++ |

TABLE 1-continued
Exemplary Compounds
| No. | Structure | Activity* JAK2 | ALK2 |
|---|---|---|---|
| 9 | 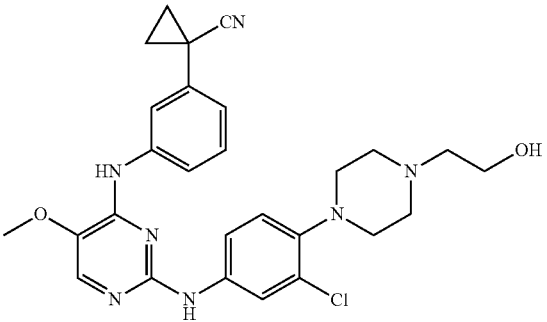 [SMILES: COc1cnc(Nc2ccc(N3CCN(CCO)CC3)c(Cl)c2)nc1Nc1cccc(C2(C#N)CC2)c1] | ++ | + |
| 10 | 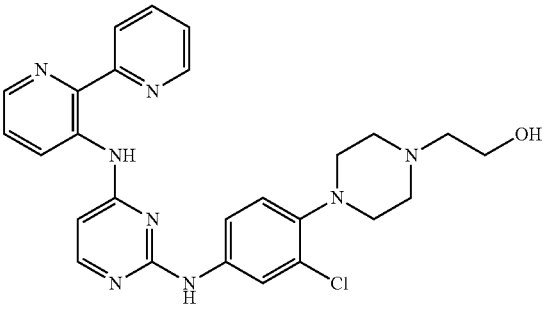 [SMILES: OCCN1CCN(c2ccc(Nc3nccc(Nc4cccnc4-c4ccccn4)n3)cc2Cl)CC1] | ++ | ++ |
| 11 | 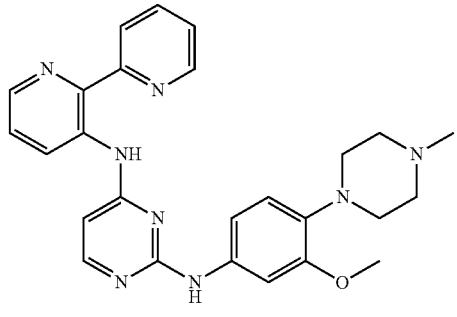 [SMILES: COc1cc(Nc2nccc(Nc3cccnc3-c3ccccn3)n2)ccc1N1CCN(C)CC1] | + | +++ |
| 12 | 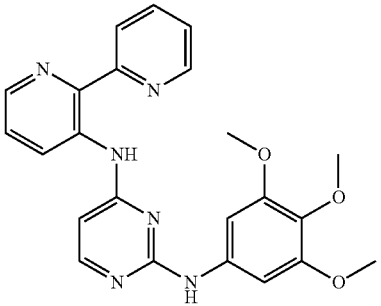 [SMILES: COc1cc(Nc2nccc(Nc3cccnc3-c3ccccn3)n2)cc(OC)c1OC] | + | +++ |

TABLE 1-continued

Exemplary Compounds

| No. | Structure | Activity* JAK2 | ALK2 |
|---|---|---|---|
| 13 | | + | + |
| 14 | | ++ | + |
| 15 | | + | ++ |
| 16 | | + | ++ |

TABLE 1-continued

Exemplary Compounds

| No. | Structure | Activity* JAK2 | ALK2 |
|---|---|---|---|
| 17 | 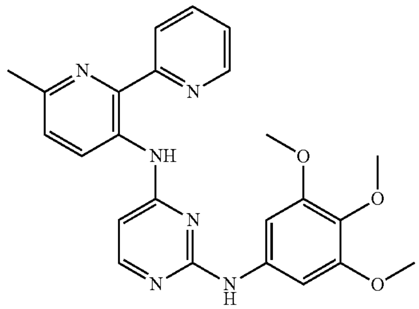 | + | ++ |
| 18 | 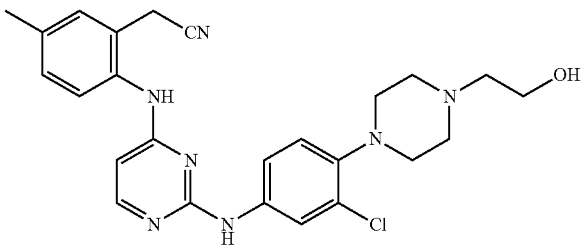 [SMILES: Cc1ccc(Nc2ccnc(Nc3ccc(N4CCN(CCO)CC4)c(Cl)c3)n2)c(CC#N)c1] | ++ | ++ |
| 19 | 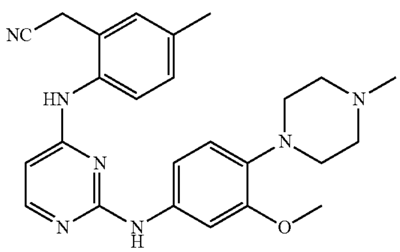 [SMILES: COc1cc(Nc2nccc(Nc3ccc(C)cc3CC#N)n2)ccc1N1CCN(C)CC1] | ++ | ++ |
| 20 | 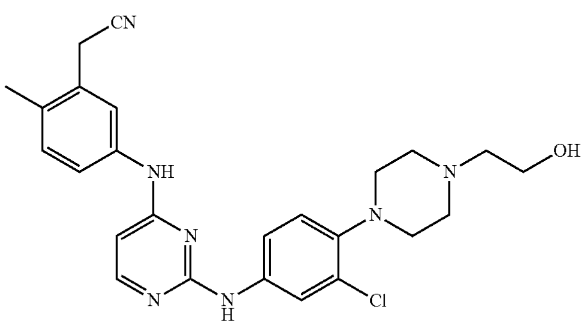 [SMILES: Cc1ccc(Nc2ccnc(Nc3ccc(N4CCN(CCO)CC4)c(Cl)c3)n2)cc1CC#N] | +++ | ++ |
| 21 | 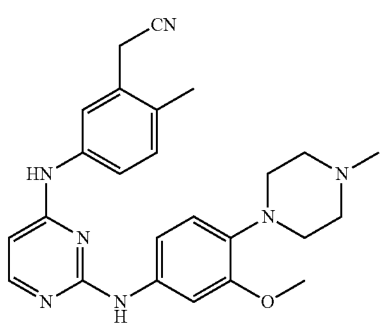 [SMILES: COc1cc(Nc2nccc(Nc3ccc(C)c(CC#N)c3)n2)ccc1N1CCN(C)CC1] | +++ | ++ |

TABLE 1-continued

Exemplary Compounds

| No. | Structure | Activity* JAK2 | ALK2 |
|---|---|---|---|
| 22 | | ++ | ++ |
| 23 | | N/D | N/D |
| 24 | | N/D | N/D |
| 25 | | N/D | N/D |

TABLE 1-continued

Exemplary Compounds

| No. | Structure | Activity* JAK2 | ALK2 |
|---|---|---|---|
| 26 | (structure) | N/D | N/D |
| 27 | (structure) | N/D | N/D |
| 28 | (structure) | N/D | N/D |

*IC$_{50}$ in nM, wherein: + is greater than 1,000 nM; ++ is 1,000 nM to 10 nM; and +++ is less than 10 nM It is understood that any embodiment of the compounds of structure (I), as set forth above, and any of the specific substituents set forth herein (e.g., $R^1$-$R^9$) in the compounds of structures (I) and (II), as set forth above, may be independently combined with other embodiments and/or substituents of compounds of structures (I) and (II) to form embodiments of the inventions not specifically set forth above. In addition, in the event that a list of substituents is listed for any particular R group in a particular embodiment and/or claim, it is understood that each individual substituent may be deleted from the particular embodiment and/or claim and that the remaining list of substituents will be considered to be within the scope of the invention. It is understood that in the present description, combinations of substituents and/or variables of the depicted formulae are permissible only if such contributions result in stable compounds.

The compounds of the present invention can be prepared according to any number of methods known in the art, including those methods specifically described in the Examples below. The following General Reaction Scheme I illustrates a method of making compounds of this invention, i.e., compounds of structure (I), wherein $R^1$-$R^8$, A and X are as defined above and LG and LG' are independently leaving groups.

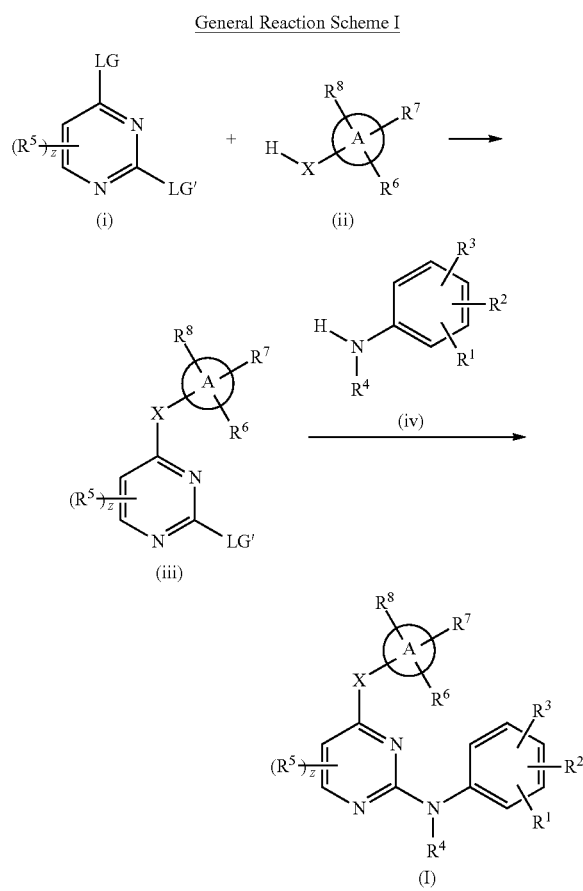

General Reaction Scheme I

Referring to General Reaction Scheme I, compounds of structures (i), (ii) and (iv) can be prepared according to methods known in the art (e.g., as exemplified in the Examples) or purchased from commercial sources. Reaction of (i) with (ii) under appropriate conditions (e.g., in the presence of a base) results in compounds of structure (iii). Further reaction of (iii) with (iv) under appropriate conditions (e.g., in the presence of a base) produces compounds of structure (I).

It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

It will be appreciated by those skilled in the art that the order of steps illustrated in General Reaction Scheme I (as well as other modifications) can be made to arrive at compounds of structure (I). It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

III. Compositions and Administration

In other embodiments, the present invention is directed to a pharmaceutical composition comprising a compound of structure (I) or (II), or a stereoisomer, pharmaceutically acceptable salt, tautomer or prodrug thereof, and a pharmaceutically acceptable carrier, diluent or excipient.

For the purposes of administration, the compounds of the present invention may be administered as a raw chemical or may be formulated as pharmaceutical compositions. Pharmaceutical compositions of the present invention comprise a compound of structure (I) and a pharmaceutically acceptable carrier, diluent or excipient. The compound of structure (I) is present in the composition in an amount which is effective to treat a particular disease or condition of interest—that is, in an amount sufficient to treat various cancers, and preferably with acceptable toxicity to the patient. JAK2 and/or ALK2 kinase activity of compounds of structure (I) can be determined by one skilled in the art, for example, as described in the Examples below. Appropriate concentrations and dosages can be readily determined by one skilled in the art.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compounds of the invention, or pharmaceutically acceptable derivatives thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

For any compound used in the methods of the invention, the therapeutically effective amount or dose can be estimated initially from cell culture assays. Then, the dosage can be formulated for use in animal models so as to achieve a circulating concentration range that includes the IC50 as determined in cell culture (i.e., the concentration of the test compound which achieves a half-maximal inhibition of the protein kinase activity). Such information can then be used to more accurately determine useful doses in humans.

Toxicity and therapeutic efficacy of the compounds described herein can be determined by standard pharmaceutical procedures in cell cultures or experimental animals, e.g., by determining the IC50 and the LD50 (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See, e.g., GOODMAN & GILMAN'S THE PHARMACOLOGICAL BASIS OF THERAPEUTICS, Ch. 3, 9th ed., Ed. by Hardman, J., and Limbard, L., McGraw-Hill, New York City, 1996, p. 46.)

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50-90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10-90% of the time, preferably between 30-90% and most preferably between 50-90%.

At present, the therapeutically effective amounts of compounds of the present invention may range from approximately 2.5 mg/m2 to 1500 mg/m2 per day. Additional illustrative amounts range from 0.2-1000 mg/qid, 2-500 mg/qid, and 20-250 mg/qid.

In cases of local administration or selective uptake, the effective local concentration of the drug may not be related to plasma concentration, and other procedures known in the art may be employed to determine the correct dosage amount and interval.

The amount of a composition administered will, of course, be dependent on the subject being treated, the severity of the affliction, the manner of administration, the judgment of the prescribing physician, etc.

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

IV. Treatment Methods

In various other embodiments, the invention is directed to a method of inhibiting ALK2 kinase or JAK2 kinase, or combinations thereof, in a mammal in need thereof, the method comprising administering to the mammal an effective amount of any of the foregoing compounds (i.e., compounds of structure (I) or (II)) or a pharmaceutical composition of claim comprising the compound.

In certain embodiments, the method is for inhibiting ALK2 Kinase. In other embodiments, the method is for inhibiting JAK2 kinase.

In still more embodiments, the inhibition is for treatment of cancer. In more embodiments, the inhibition is for treatment of anemia of chronic disease, anemia of chronic inflammation, anemia of cancer or fibrodysplasia ossificans progressive.

In another embodiment, the present disclosure is directed to a method for treating cancer in a mammal in need thereof, the method comprising administering to the mammal an effective amount of any of the foregoing compounds (i.e., compounds of structure (I) or (II)) or a pharmaceutical composition of claim comprising the compound.

In certain embodiments of the foregoing method, the cancer is a myeloproliferative disorder, a lymphoma or a solid tumor. For example, in some embodiments the myeloproliferative disorder is myelofibrosis, polycythemia vera or essential thrombocytosis.

In other embodiments, the solid tumor is a breast, prostate or pancreatic tumor.

In still more embodiments, the cancer is prostate, ovarian or head and neck cancers.

The invention also provides for treatment of various other cancers by administration of the compounds of structure (I) or (II) as described below Advantageously, the present compounds find utility in methods for treating and alleviating symptoms of cancer. Accordingly, in some embodiments a method for providing supportive care to a cancer patient (i.e, a subject, such as a human subject, diagnosed as having cancer) in need thereof, the method comprising administering to the patient an effective amount of any of the foregoing compounds (i.e., compounds of structure (I) or (II)) or a pharmaceutical composition of claim comprising the compound. For example, in some embodiments the method is for treating anemia and fatigue associated with cancer.

As mentioned above, the compounds and compositions of the invention will find utility in a broad range of diseases and conditions mediated by ALK2 and/or JAK2 protein kinases. Such diseases may include by way of example and not limitation, cancers such as as hematological cancers (e.g., acute myelogenous leukemia (AML) and chronic myelogenous leukemia (CML)) lung cancer, NSCLC (non small cell lung cancer), oat-cell cancer, bone cancer, pancreatic cancer, skin cancer, dermatofibrosarcoma protuberans, cancer of the head and neck, cutaneous or intraocular melanoma, uterine cancer, ovarian cancer, colo-rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, hepatocellular cancer, cancer of the esophagus, cancer of the small intestine, cancer of the endocrine system (e.g., cancer of the thyroid, pancreas, parathyroid or adrenal glands), sarcomas of soft tissues, cancer of the urethra, cancer of the penis, testicular cancer, prostate cancer (particularly hormone-refractory), chronic or acute leukemia, solid tumors of childhood, hypereosinophilia, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, medulloblastoma, brain stem gliomas or pituitary adenomas), Barrett's esophagus (pre-malignant syndrome), neoplastic cutaneous disease, psoriasis, mycoses fungoides, and benign prostatic hypertrophy, diabetes related diseases such as diabetic retinopathy, retinal ischemia, and retinal neovascularization, hepatic cirrhosis, angiogenesis, cardiovascular disease such as atherosclerosis, immunological disease such as autoimmune disease and renal disease.

In some embodiments, the compounds and compositions of the invention can be used in methods for treating cancers such as hematological malignancies. For example, in some embodiments the compounds and compositions of the invention can be used in methods for treating acute myeloid leukemia (AML). Other methods include treatment of bladder cancer, or treatment of prostate cancer.

The inventive compounds (i.e., compounds of structure (I)) can be used in combination with one or more other chemotherapeutic agents. The dosage of the inventive compounds may be adjusted for any drug-drug reaction. In one embodiment, the chemotherapeutic agent is selected from the group consisting of mitotic inhibitors, alkylating agents, anti-metabolites, cell cycle inhibitors, enzymes, topoisomerase inhibitors such as CAMPTOSAR (irinotecan), biological response modifiers, anti-hormones, antiangiogenic agents such as MMP-2, MMP-9 and COX-2 inhibitors, anti-androgens, platinum coordination complexes (cisplatin, etc.), substituted ureas such as hydroxyurea; methylhydrazine derivatives, e.g., procarbazine; adrenocortical suppressants, e.g., mitotane, aminoglutethimide, hormone and hormone antagonists such as the adrenocorticosteriods (e.g., prednisone), progestins (e.g., hydroxyprogesterone caproate), estrogens (e.g., diethylstilbesterol), antiestrogens such as tamoxifen, androgens, e.g., testosterone propionate, and aromatase inhibitors, such as anastrozole, and AROMASIN (exemestane).

Examples of alkylating agents that the above method can be carried out in combination with include, without limitation, fluorouracil (5-FU) alone or in further combination with leukovorin; other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Examples of antimetabolite chemotherapeutic agents that the above method can be carried out in combination with include, without limitation, folic acid analogs, e.g., methotrexate (used in the treatment of acute lymphocytic leukemia, choriocarcinoma, mycosis fungiodes, breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

Examples of natural product-based chemotherapeutic agents that the above method can be carried out in combination with include, without limitation, the vinca alkaloids, e.g., vinblastine (used in the treatment of breast and testicular cancer), vincristine and vindesine; the epipodophyllotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

Examples of useful COX-II inhibitors include Vioxx, CELEBREX (celecoxib), valdecoxib, paracoxib, rofecoxib, and Cox 189.

Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred are those that selectively inhibit MMP-2 and/or MMP-9 relative to the other matrix-metalloproteinases (i.e., MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and compounds selected from: 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methylbenzyloxy)-benzenesulfonyl]-3-hydroxy-3-methyl-piperidine-2-carboxylic acid hydroxyamide; 3-[[(4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide; 3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of these compounds.

Other anti-angiogenesis agents, other COX-II inhibitors and other MMP inhibitors, can also be used in the present invention.

An inventive compound can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, such as HERCEPTIN (Genentech, Inc., South San Francisco, Calif.). EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein.

EGFR-inhibiting agents include, but are not limited to, the monoclonal antibodies C225 and anti-EGFR 22Mab (ImClone Systems, Inc., New York, N.Y.), the compounds ZD-1839 (AstraZeneca), BIBX-1382 (Boehringer Ingelheim), MDX-447 (Medarex Inc., Annandale, N.J.), and OLX-103 (Merck & Co., Whitehouse Station, N.J.), and EGF fusion toxin (Seragen Inc., Hopkinton, Mass.).

These and other EGFR-inhibiting agents can be used in the present invention. VEGF inhibitors, for example SU-5416 and SU-6668 (Sugen Inc., South San Francisco, Calif.), can also be combined with an inventive compound. VEGF inhibitors are described in, for example, WO 01/60814 A3 (published Aug. 23, 2001), WO 99/24440 (published May 20, 1999), PCT International Application PCT/IB99/00797 (filed May 3, 1999), WO 95/21613 (published Aug. 17, 1995), WO 99/61422 (published Dec. 2, 1999), U.S. Pat. No. 5,834,504 (issued Nov. 10, 1998), WO 01/60814, WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc., Kirkland, Wash.); anti-VEGF monoclonal antibody of Genentech, Inc.; and angiozyme, a synthetic ribozyme from Ribozyme (Boulder, Colo.) and Chiron (Emeryville, Calif.). These and other VEGF inhibitors can be used in the present invention as described herein. pErbB2 receptor inhibitors, such as GW-282974 (Glaxo Wellcome plc), and the monoclonal antibodies AR-209 (Aronex Pharmaceuticals Inc., The Woodlands, Tex.) and 2B-1 (Chiron), can furthermore be combined with an inventive compound, for example, those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Pat. No. 6,284,764 (issued Sep. 4, 2001), incorporated in its entirety herein by reference. The erbB2 receptor inhibitor compounds and substance described in the aforementioned PCT applications, U.S. patents, and U.S. provisional applications, as well as other compounds and substances that inhibit the erbB2 receptor, can be used with an inventive compound, in accordance with the present invention.

An inventive compound can also be used with other agents useful in treating cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, of U.S. Pat. No. 6,258,824 B1.

The above method can also be carried out in combination with radiation therapy, wherein the amount of an inventive compound in combination with the radiation therapy is effective in treating the above diseases.

Techniques for administering radiation therapy are known in the art, and these techniques can be used in the combination therapy described herein. The administration of the compound of the invention in this combination therapy can be determined as described herein.

The following examples are provided for purposes of illustration, not limitation.

Example 1

Synthesis of Compounds

Preparation of 2-(4-(4-amino-2-methoxyphenyl)piperazin-1-yl)ethanol (aniline A)

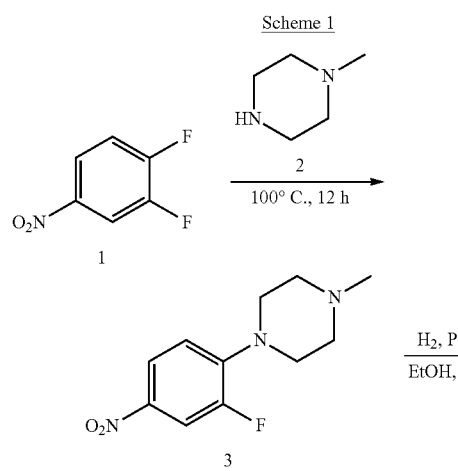

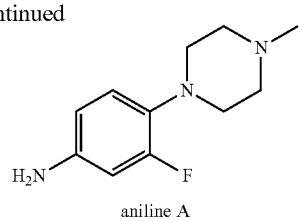

aniline A

A mixture of scheme 1 compound 1 (5.0 g, 31.4 mmol) and scheme 1 compound 2 (70 mL, 628.0 mmol) was heated to 100° C. for 12 h in a sealed tube. After TLC showed the starting material was consumed completely, the reaction mixture was diluted with water (20 mL) and extracted with EtOAc (5×100 mL). The organic layer was dried over $Na_2SO_4$, filtered and concentrated to give scheme 1 compound 3 (3.0 g, 62% yield) as a yellow solid which was used without further purification. $^1$H NMR (400 MHz, $CDCl_3$): δ 8.09-7.71 (m, 2H), 6.90 (t, J=8.8 Hz, 1H), 3.31 (dd, J=5.9, 3.9 Hz, 4H), 2.73-2.52 (m, 4H), 2.35 (s, 3H). MS [ESI, $MH^+$]=240.15.

Pd/C (10%, 200 mg) was added to scheme 1 compound 3 (1.0 g, 4.18 mmol) in ethanol (10 mL) and the resulting mixture was stirred under $H_2$ atmosphere (balloon pressure) for 12 h. After TLC showed the starting material was consumed completely, the reaction mixture was passed through a pad of celite and the solids were washed with EtOAc (30 mL). The filtrate was dried over $Na_2SO_4$, filtered and concentrated to give aniline A (600 mg, 69% yield) as a brown semi solid. $^1$H NMR (400 MHz, DMSO-$d_6$): δ 6.75 (dd, J=10.0, 8.3 Hz, 1H), 6.50-6.21 (m, 2H), 4.97 (s, 2H), 2.81 (t, J=4.9 Hz, 4H), 2.41 (s, 4H), 2.19 (s, 3H). MS [ESI, $MH^+$]=210.13.

Preparation of 3-methoxy-4-(4-methylpiperazin-1-yl)aniline (aniline B)

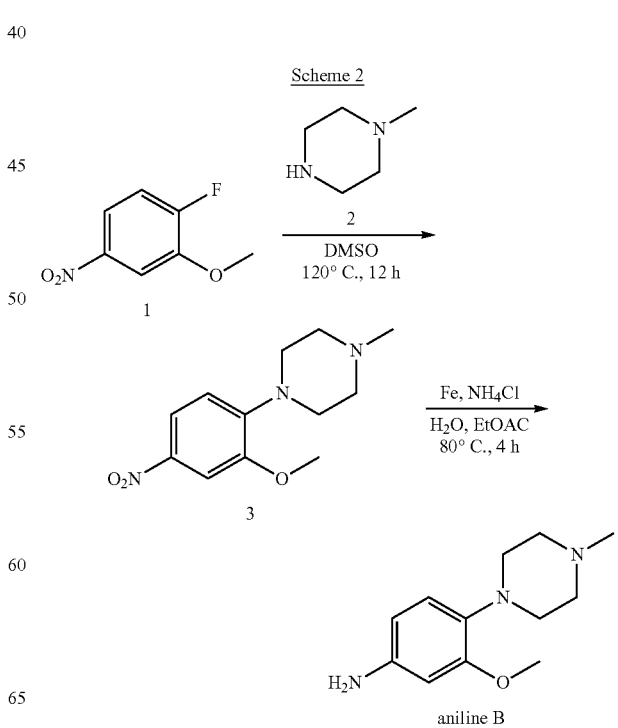

A mixture of scheme 2 compound 1 (2.00 g, 11.68 mmol) and scheme 2 compound 2 (1.17 g, 11.68 mmol) in dry DMSO (5 mL) was heated to 120° C. for 12 h. After TLC showed the starting material was consumed completely, the reaction mixture was diluted with water (20 mL) and extracted with EtOAc (5×50 mL). The organic layer was dried over $Na_2SO_4$, filtered and concentrated to give scheme 2 compound 3 (2.00 g, 69% yield) as a brown solid which was used without further purification. $^1$H NMR (400 MHz, $CDCl_3$): δ 7.87 (dd, J=8.8, 2.6 Hz, 1H), 7.71 (d, J=2.5 Hz, 1H), 6.90 (d, J=8.8 Hz, 1H), 3.95 (s, 3H), 3.26 (d, J=4.9 Hz, 4H), 2.61 (t, J=4.9 Hz, 4H), 2.37 (s, 3H). MS [ESI, MH$^+$]=252.13.

A mixture of crude scheme 2 compound 3 (1.00 g, 3.98 mmol), Fe (0.89 g, 15.93 mmol) and $NH_4Cl$ (2.70 g, 39.80 mmol) in $EtOAc/H_2O$ (20 mL, 1/1) was heated to 80° C. for 4 h. After TLC showed the starting material was consumed completely, the reaction mixture was passed through a pad of celite and the solids were washed with EtOAc (50 mL). The filtrate was evaporated under reduced pressure to give a residue which was purified by flash chromatography on neutral alumina (eluting with $CH_2Cl_2$/MeOH 99/1 gradually increasing to 80/20) to give aniline B (0.70 g, 79% yield) as a brown solid. $^1$H NMR (400 MHz, DMSO-$d_6$): δ 6.60 (dd, J=8.4, 2.0 Hz, 1H), 6.21 (d, J=2.3 Hz, 1H), 6.06 (m, 1H), 4.71 (s, 2H), 3.67 (d, J=2.0 Hz, 3H), 2.78 (s, 4H), 2.46-2.33 (m, 4H), 2.19 (d, J=2.1 Hz, 3H). MS [ESI, MH$^+$]=222.16.

Preparation of 2-(4-(4-amino-2-methoxyphenyl)piperazin-1-yl)ethanol (aniline C)

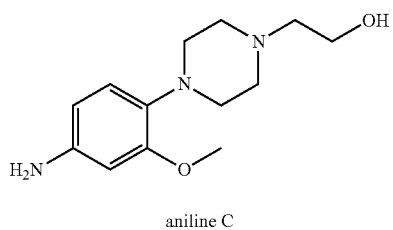 [SMILES: COc1cc(N)ccc1N1CCN(CCO)CC1]

aniline C

The title compound was synthesized in a similar manner as aniline B using 2-(piperazin-1-yl)ethanol in the first step. Aniline C was obtained as a brown solid (5.0 g, 34% yield over 2 steps). $^1$H NMR (400 MHz, DMSO-$d_6$): δ 6.60 (d, J=8.3 Hz, 1H), 6.22 (d, J=2.4 Hz, 1H), 6.07 (dd, J=8.3, 2.4 Hz, 1H), 4.73 (s, 3H), 3.68 (s, 3H), 3.53 (d, J=27.0 Hz, 2H), 2.84 (s, 4H), 2.54 (s, 6H). MS [ESI, MH$^+$]=252.17.

Preparation of 2-(4-(4-amino-2-methoxyphenyl)piperazin-1-yl)ethanol (aniline D)

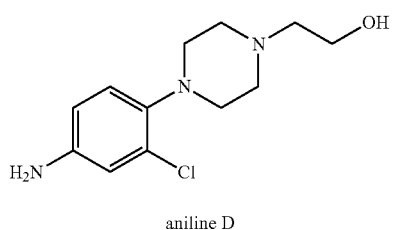 [SMILES: Nc1ccc(N2CCN(CCO)CC2)c(Cl)c1]

aniline D

The title compound was synthesized in a similar manner as aniline B using 2-chloro-1-fluoro-4-nitrobenzene and 2-(piperazin-1-yl)ethanol in the first step. Aniline D was obtained as a brown solid (1.5 g, 51% yield over 2 steps). $^1$H NMR (400 MHz, DMSO-$d_6$): δ 6.91 (d, J=8.6 Hz, 1H), 6.65 (d, J=2.5 Hz, 1H), 6.51 (dd, J=8.6, 2.5 Hz, 1H), 5.34 (s, 1H), 5.18 (s, 2H), 3.78 (d, J=5.0 Hz, 2H), 3.52 (s, 2H), 3.15 (d, J=46.2 Hz, 10H). MS [ESI, MH$^+$]=256.12.

Preparation of 2-(3-((5-chloro-2((3-fluoro-4-(4-methylpiperazin-1-yl)phenyl)amino)pyrimidin-4-yl)amino)phenyl)acetonitrile (Compound 1)

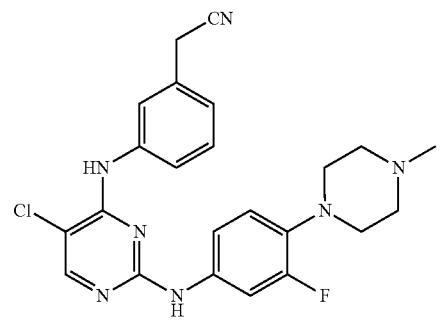 [SMILES: CN1CCN(c2ccc(Nc3ncc(Cl)c(Nc4cccc(CC#N)c4)n3)cc2F)CC1]

The title compound was synthesized following the procedure depicted in scheme 3.

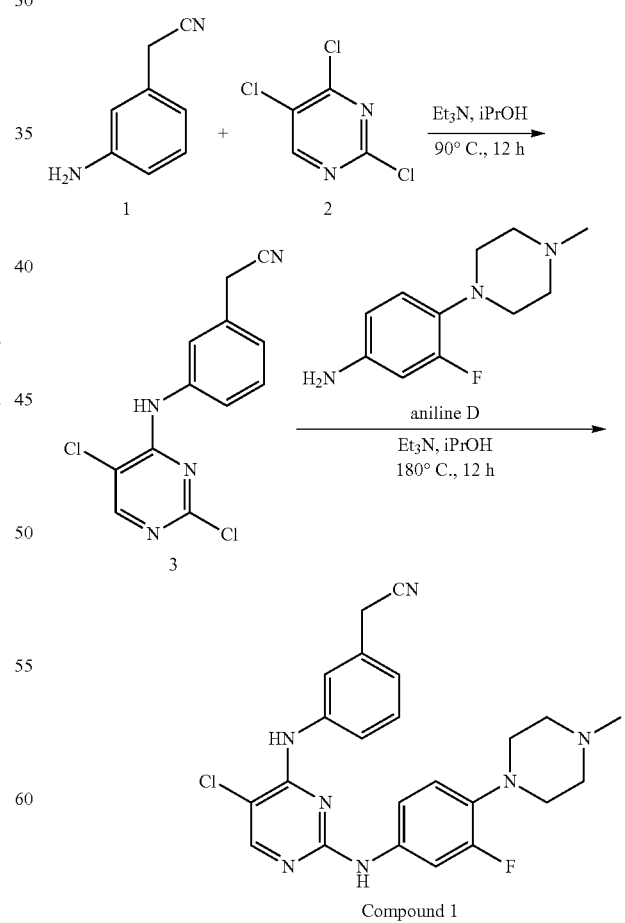

Scheme 3

Et$_3$N (0.16 mL) was added to a mixture of scheme 3 compound 1 (100 mg, 0.55 mmol) and scheme 3 compound 2 (76 mg, 0.57 mmol) in iPrOH (4 mL) and the resulting mixture was heated to 90° C. for 12 h. After TLC showed the starting material was consumed completely, the solvent was evaporated and the residue was purified by flash chromatography on silica get to give scheme 3 compound 3 (91 mg, 59% yield).

Et₃N (0.5 mL) was added to a mixture of scheme 3 compound 3 (50 mg, 0.179 mmol) and aniline A (49 mg, 0.234 mmol) in iPrOH (5 mL) and the resulting mixture was heated to 90° C. for 12 h in a sealed tube. After TLC showed the starting material was consumed completely, the solvent was evaporated and the residue was purified by flash chromatography on silica get to give Compound 1 (63 mg, 77% yield). MS [ESI, (M–CH₃+H)⁺]=438.16.

Preparation of 2-(3-((2-((3-fluoro-4-(4-methylpiperazin-1-yl)phenyl)amino)-5-methylpyrimidin-4-yl)amino)phenyl)acetonitrile (Compound 2)

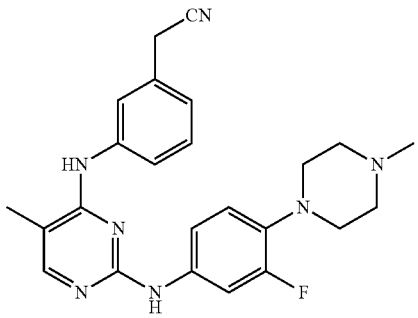

The title compound was synthesized in a similar manner as Compound 1 using 2,4-dichloro-5-methylpyrimidine in the first coupling step. Compound 2 was obtained as a white solid (18 mg, 5% yield over 2 steps). MS [ESI, (M–CH₃+H)⁺]=418.29.

Preparation of 4-((3-(cyanomethyl)phenyl)amino)-2((3-fluoro-4-(4-methylpiperazin-1-yl)phenyl)amino)pyrimidine-5-carbonitrile (Compound 3)

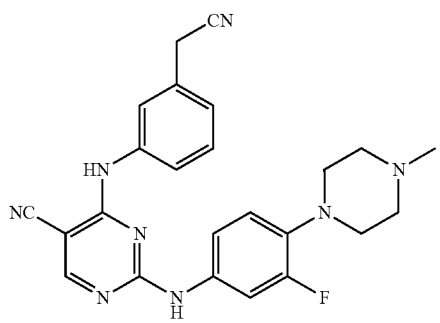 [SMILES: CN1CCN(c2ccc(Nc3ncc(C#N)c(Nc4cccc(CC#N)c4)n3)cc2F)CC1]

The title compound was synthesized in a similar manner as Compound 1 using 2,4-dichloropyrimidine-5-carbonitrile in the first coupling step and reducing the temperature for this step to RT. Compound 3 was obtained as a white solid (47 mg, 39% yield over 2 steps). MS [ESI, (M–CH₃+H)⁺]=429.21.

Preparation of 1-(3-(2-(3-methoxy-4-(4-methylpiperazin-1-yl)phenylamino)pyrimidin-4-ylamino)phenyl)cyclopropanecarbonitrile (Compound 4)

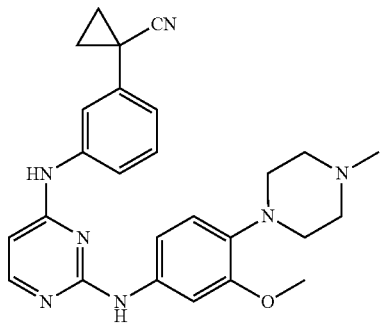 [SMILES: COc1cc(Nc2nccc(Nc3cccc(C4(C#N)CC4)c3)n2)ccc1N1CCN(C)CC1]

The title compound was synthesized following the procedure depicted in scheme 4. The preparation of 1-(3-aminophenyl)cyclopropanecarbonitrile (scheme 4 compound 1) is described below in scheme 5.

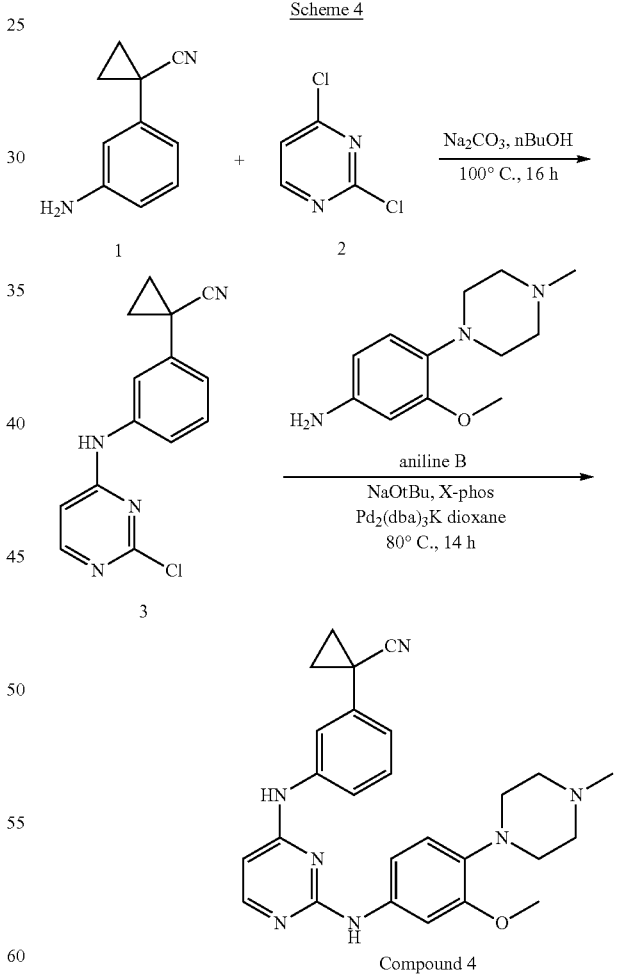

Compound 4

A mixture of scheme 4 compound 1 (400 mg, 2.53 mmol), scheme 4 compound 2 (450 mg, 3.03 mmol) and Na₂CO₃ (536 mg, 5.06 mmol) in nBuOH (5 mL) was heated to 100° C. for 16 h in a sealed tube. After TLC showed the starting material was consumed completely, the reaction mixture was diluted with water (20 mL) and extracted with EtOAc (2×20 mL). The organic layer was dried over Na$_2$SO$_4$, filtered and concentrated to give a residue which was triturated with a combination of Et$_2$O and n-pentane (20 mL, ¼) to give scheme 4 compound 3 (300 mg, 44% yield) as an off-white solid. $^1$H NMR (400 MHz, DMSO-d$_6$): δ10.15 (s, 1H), 8.19 (m, 1H), 7.78-7.47 (m, 2H), 7.49-7.23 (m, 1H), 7.14-6.92 (m, 1H), 6.77 (m, 1H), 1.79 (d, J=5.0 Hz, 2H), 1.51 (t, J=3.9 Hz, 2H). MS [ESI, MH$^+$]=271.05.

Scheme 4 compound 3 (150 mg, 0.55 mmol) and aniline B (200 mg, 0.83 mmol) were dissolved in anhydrous dioxane (10 mL). To this mixture was added t-BuONa (160 mg, 1.66 mmol), X-PHOS (64 mg, 0.11 mmol) and Pd$_2$(dba)$_3$ (50 mg, 0.05 mmol, 5 mol %) under nitrogen atmosphere. The reaction mixture was stirred at 80° C. for 14 h. After TLC showed the starting material was consumed completely, the mixture was quenched with water (10 mL) and extracted with ethyl acetate (30 mL). The organic layer was washed with brine (10 mL) and dried over anhydrous Na$_2$SO$_4$ then filtered, concentrated to give a residue which was purified by prep-HPLC to give Compound 4 (70 mg, 28% yield) as an off-white solid. $^1$H NMR (400 MHz, CDCl$_3$): δ 8.07 (d, J=5.7 Hz, 1H), 7.43 (s, 1H), 7.40-7.27 (m, 2H), 7.16 (d, J=2.4 Hz, 1H), 7.06 (m, 1H), 6.98 (m, 1H), 6.94-6.86 (m, 2H), 6.58 (s, 1H), 6.13 (d, J=5.8 Hz, 1H), 3.80 (s, 3H), 3.07 (s, 4H), 2.63 (s, 4H), 2.36 (s, 3H), 1.72 (d, J=5.0 Hz, 2H), 1.38 (d, J=5.1 Hz, 2H). MS [ESI, MH$^+$]=456.20.

1-(3-Aminophenyl)cyclopropanecarbonitrile (scheme 4 compound 1) was synthesized as shown in scheme 5.

Scheme 5

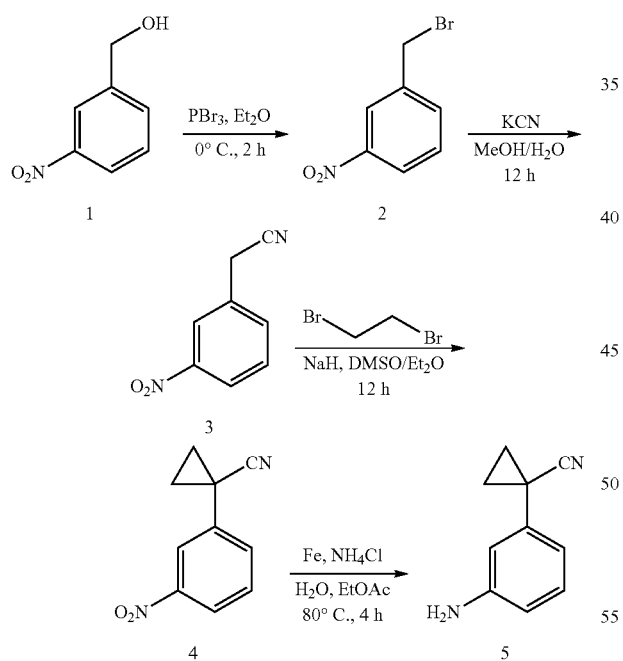

PBr$_3$ (38.9 g, 270.7 mmol) was added dropwise to a cold (0° C.) solution of scheme 5 compound 1 (55.0 g, 359.4 mmol) in Et$_2$O (500 mL) and the reaction mixture was stirred for 2 h at 0° C. After TLC showed the starting material was consumed completely, the mixture was diluted with water (50 mL) and extracted with Et$_2$O (2×200 mL). The organic layer was dried over Na$_2$SO$_4$, filtered and concentrated to give scheme 5 compound 2 (55.0 g, 71% yield) as an off-white solid which was used without further purification. $^1$H NMR (400 MHz, CDCl$_3$): δ 8.27 (t, J=2.0 Hz, 1H), 8.17 (dd, J=8.6, 2.0 Hz, 1H), 7.74 (m, 1H), 7.55 (t, J=8.0 Hz, 1H), 4.54 (s, 2H). MS [ESI, MH$^+$]=215.96.

To a solution of scheme 5 compound 2 (55.0 g, 254.6 mmol) in MeOH/water (250 mL, 4/1) was added KCN (21.5 g, 331.0 mmol) and the reaction mixture was stirred at RT for 12 h. After TLC showed the starting material was consumed completely, the reaction mixture was diluted with water (50 mL) and extracted with EtOAc (200 mL). The organic layer was dried over Na$_2$SO$_4$, filtered and concentrated to give a residue which was purified by flash chromatography on silica gel (eluting with petroleum ether/EtOAc 100/0 gradually increasing to 40/60) to give scheme 5 compound 3 (38.0 g, 91% yield) as an light yellow solid. $^1$H NMR (400 MHz, CDCl$_3$): δ 8.31-8.12 (m, 2H), 7.78-7.69 (m, 1H), 7.68-7.51 (m, 1H), 3.91 (s, 2H). MS [ESI, MH$^+$]=163.05.

A mixture of scheme 5 compound 3 (20.00 g, 123.0 mmol) and 1,2-dibromoethane (23.08 g, 123.0 mmol) in DMSO/Et$_2$O (60 mL, ½) was added dropwise to a solution of NaH (5.41 g, 271.4 mmol) in DMSO (20 mL) and the resulting mixture was stirred at RT for 1 h. After TLC showed the starting material was consumed completely, the reaction mixture was quenched with iPrOH (20 mL) followed by water (20 mL) and extracted with EtOAc (30 mL). The organic layer was dried over Na$_2$SO$_4$, filtered and concentrated to give a residue which was purified by flash chromatography on silica gel (eluting with petroleum ether/EtOAc 100/0 gradually increasing to 80/20) to give scheme 5 compound 4 (13.0 g, 56% yield) as an off-white solid. $^1$H NMR (400 MHz, CDCl$_3$): δ 8.22-8.13 (m, 1H), 8.05 (t, J=2.2 Hz, 1H), 7.75 (d, J=7.9 Hz, 1H), 7.57 (t, J=8.0 Hz, 1H), 1.88 (d, J=2.7 Hz, 2H), 1.54-1.50 (m, 2H). MS [ESI, MH$^+$]=189.04.

A mixture of scheme 5 compound 4 (10.0 g, 52.6 mmol), Zn dust (13.7 g, 210.5 mmol) and NH$_4$Cl (28.1 g, 526.3 mmol) in EtOAc/H$_2$O (60 mL, 1/1) was heated to 80° C. for 4 h. After TLC showed the starting material was consumed completely, the reaction mixture was passed through a pad of celite and the solids were washed with EtOAc (200 mL). The filtrate was evaporated to give a residue which was purified by flash chromatography on neutral alumina (eluting with petroleum ether/EtOAc 100/0 gradually increasing to 70/30) to give scheme 5 compound 5 (6.0 g, 71% yield) as a brown liquid. $^1$H NMR (400 MHz, DMSO-d$_6$): δ 6.99 (t, J=7.8 Hz, 1H), 6.57 (t, J=2.1 Hz, 1H), 6.47 (dd, J=8.0, 2.1 Hz, 1H), 6.39-6.34 (m, 1H), 5.21 (s, 2H), 1.66 (m, 2H), 1.36 (q, J=4.7 Hz, 2H). MS [ESI, MH$^+$]=159.09

Preparation of 1-(3-(2-(3,4,5-trimethoxyphenylamino)pyrimidin-4-ylamino)phenyl)cyclopropanecarbonitrile (Compound 5)

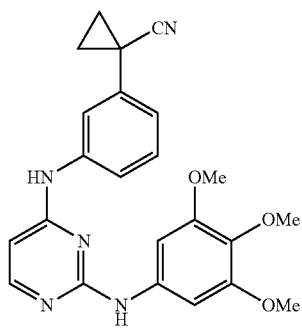 [SMILES: COc1cc(Nc2nccc(Nc3cccc(C4(C#N)CC4)c3)n2)cc(OC)c1OC]

The title compound was synthesized in a similar manner as Compound 4 using 3,4,5-trimethoxyaniline in the final coupling step.

Scheme 4 compound 3 (120 mg, 0.440 mmol) and 3,4,5-trimethoxyaniline (122 mg, 0.660 mmol) were dissolved in anhydrous dioxane (10 mL). To this mixture were added t-BuONa (126 mg, 1.320 mmol), X-PHOS (50 mg, 0.088 mmol) and Pd$_2$(dba)$_3$ (40 mg, 0.044 mmol, 10 mol %) under nitrogen atmosphere. The reaction mixture was stirred at 80° C. for 14 h. After TLC showed the starting material was consumed completely, the mixture was quenched with water (10 mL) and extracted with ethyl acetate (30 mL). The organic layer was washed with brine (10 mL) and dried over anhydrous Na$_2$SO$_4$ then filtered and concentrated to give a residue which was purified by prep-HPLC to give Compound 5 (120 mg, 66% yield) as an off-white solid. $^1$H NMR (400 MHz, CDCl$_3$): δ 8.09 (d, J=5.7 Hz, 1H), 7.50 (s, 1H), 7.44-7.28 (m, 2H), 7.03-6.88 (m, 2H), 6.85 (s, 2H), 6.56 (s, 1H), 6.15 (d, J=5.7 Hz, 1H), 3.82 (d, J=7.9 Hz, 9H), 1.74 (d, J=5.1 Hz, 2H), 1.39 (d, J=5.0 Hz, 2H). MS [ESI, MH$^+$]=418.15.

Preparation of 1-(3-(2-(4-(4-(2-hydroxyethyl)piperazin-1-yl)-3-methoxyphenylamino) pyrimidin-4-ylamino)phenyl)cyclopropanecarbonitrile (Compound 6)

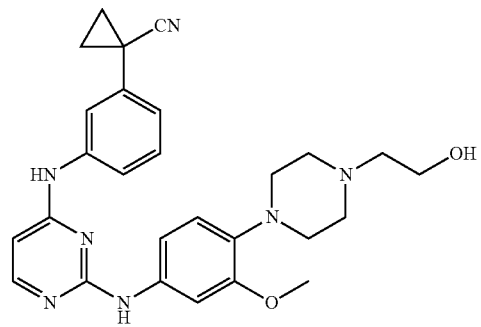 [SMILES: COc1cc(Nc2nccc(Nc3cccc(C4(C#N)CC4)c3)n2)ccc1N1CCN(CCO)CC1]

The title compound was synthesized following the procedure depicted in scheme 6.

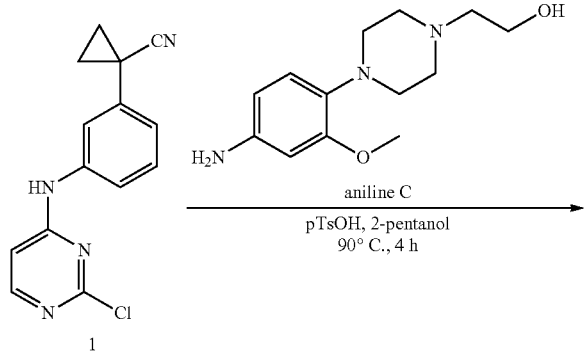

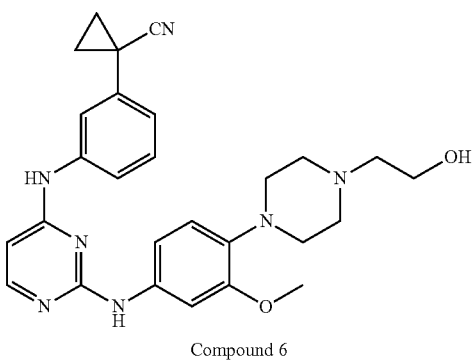

Compound 6

A mixture of scheme 6 compound 1 (2.0 g, 7.38 mmol), aniline C (2.2 g, 8.56 mmol) and pTsOH (1.2 g, 7.38 mmol) in 2-pentanol (40 mL) was heated to 90° C. for 4 h. After TLC showed the starting material was consumed completely, the reaction mixture was diluted with water (20 mL), neutralized with aqueous NaHCO$_3$ (pH 8) and extracted with EtOAc (2×50 mL). The organic layer was dried over Na$_2$SO$_4$, filtered and concentrated to give a residue which was purified by flash chromatography on neutral alumina (eluting with CH$_2$Cl$_2$/MeOH 100/0 gradually increasing to 90/10) to give Compound 6 (1.3 g, 36% yield) as an off-white solid. $^1$H NMR (400 MHz, DMSO-d$_6$): δ 8.94 (s, 1H), 8.00 (d, J=5.6 Hz, 1H), 7.90 (d, J=8.1 Hz, 1H), 7.40 (t, J=2.1 Hz, 1H), 7.32-7.19 (m, 3H), 6.91 (d, J=7.7 Hz, 1H), 6.78 (d, J=8.4 Hz, 1H), 6.18 (d, J=5.7 Hz, 1H), 4.40 (s, 1H), 3.65 (s, 3H), 3.53 (s, 2H), 2.91 (s, 4H), 2.46 (s, 4H), 1.70 (d, J=4.8 Hz, 2H), 1.42 (d, J=4.7 Hz, 2H). MS [ESI, MH$^+$]=486.25.

Preparation of 1-(3-((2-((3-chloro-4-(4-(2-hydroxyethyl)piperazin-1-yl) phenyl) amino)pyrimidin-4-yl)amino)phenyl)cyclopropanecarbonitrile (Compound 7)

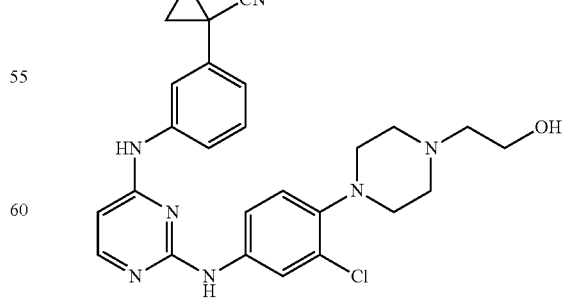

The title compound was synthesized following the procedure depicted in scheme 7.

Scheme 7

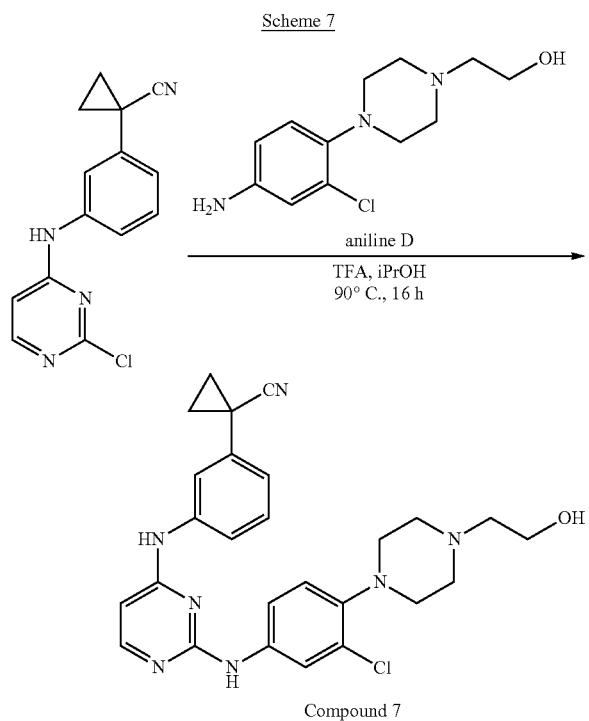

Compound 7

A mixture of scheme 7 compound 1 (50.0 mg, 0.185 mmol), aniline D (47.3 mg, 0.185 mmol) and TFA (0.5 mL) in iPrOH (10 mL) was heated to 90° C. for 16 h. After TLC showed the starting material was consumed completely, the solvent was removed under reduced pressure and the residue was purified by prep HPLC to give Compound 7 (7.6 mg, 22% yield). $^1$H NMR (400 MHz, CD$_3$OD): δ 8.31 (s, 2H), 7.95 (d, J=6.0 Hz, 1H), 7.81 (d, J=2.4 Hz, 1H), 7.66 (d, J=8.4 Hz, 1H), 7.49 (s, 1H), 7.46 (dd, J=8.8, 2.4 Hz, 1H), 7.35 (t, 1H), 7.12 (d, J=8.8 Hz, 1H), 7.05 (d, J=7.6 Hz, 1H), 6.24 (d, J=6.0 Hz, 1H), 3.92 (t, 2H), 3.45 (s, 4H), 3.28 (m, 6H), 1.67-1.64 (m, 2H), 1.42-1.38 (m, 2H). MS [ESI, MH$^+$]=490.2.

Preparation of 1-(3-((2-((3-fluoro-4-(4-methylpiperazin-1-yl)phenyl)amino)pyrimidin-4-yl)amino)phenyl)cyclopropanecarbonitrile (Compound 8)

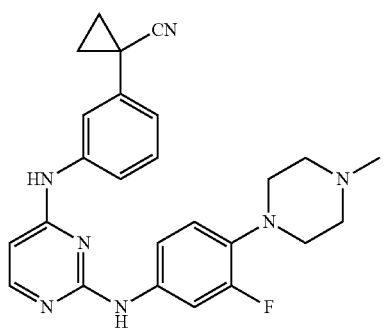 [SMILES: CN1CCN(c2ccc(Nc3nccc(Nc4cccc(C5(C#N)CC5)c4)n3)cc2F)CC1]

The title compound was synthesized following the procedure depicted in scheme 8.

Scheme 8

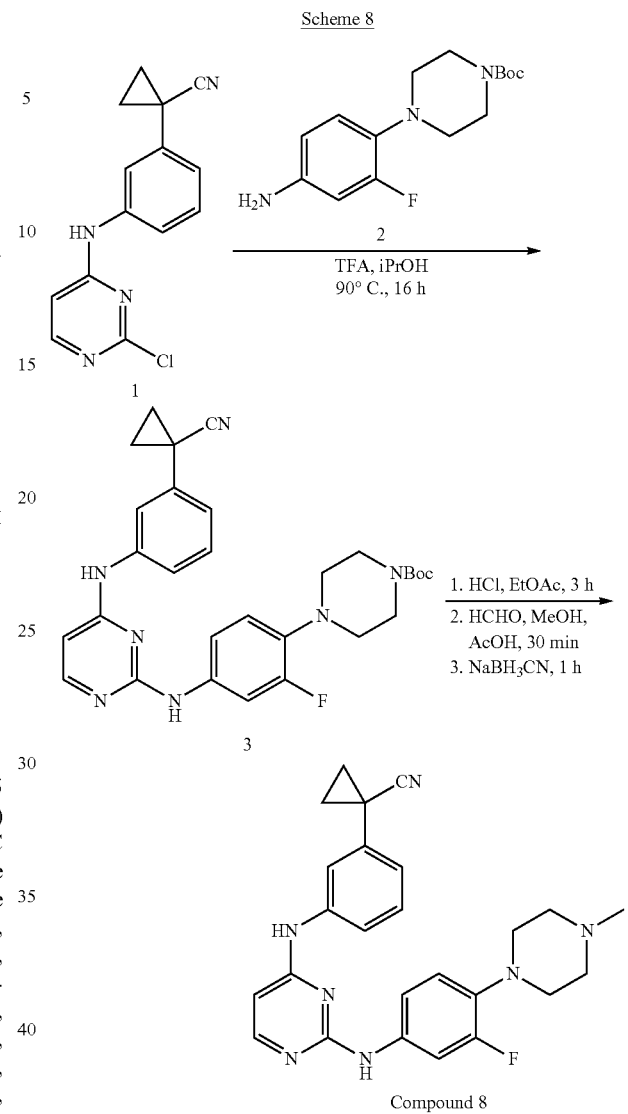

Compound 8

A mixture of scheme 8 compound 1 (50.0 mg, 0.185 mmol), scheme 8 compound 2 (54.6 mg, 0.185 mmol) and TFA (0.5 mL) in iPrOH (10 mL) was heated to 90° C. for 16 h. After LCMS showed the reaction was completed, the solvent was removed under reduced pressure to give crude scheme 8 compound 3 (100 mg) which was used without further purification. MS [ESI, MH$^+$]=530.0.

To a solution of scheme 8 compound 3 (100.0 mg, 0.19 mmol) in EtOAc (5 mL) was added HCl in EtOAc (10%, 5 mL) and the mixture was stirred at RT for 3 h. After LCMS showed the reaction was completed, the solvent was evaporated, the residue was dissolved in MeOH (5 mL) and HCHO (5.7 mg, 0.19 mmol) and AcOH (0.05 mL) were added. The mixture was stirred at RT for 30 min after which time NaBH$_3$CN (15.7 mg, 0.25 mmol) was added and the stirring was continued at RT for 1 h. After LCMS showed the reaction was completed, the solvent was evaporated to give a residue which was purified by prep-HPLC to give Compound 8 (7.9 mg, 18% yield). $^1$H NMR (400 MHz, CD$_3$OD): δ ppm: 8.30 (s, 2H), 7.95 (d, J=6.0 Hz, 1H), 7.63-7.57 (m, 2H), 7.52 (s, 1H), 7.34 (t, 1H), 7.24 (d, J=8.0 Hz, 1H), 7.05-6.98 (m, 2H), 6.23 (d, J=6.0 Hz, 1H), 3.30 (m, 8H), 2.87 (s, 3H), 1.68-1.64 (m, 2H), 1.43-1.39 (m, 2H). MS [ESI, MH⁺]=444.2

Preparation of 1-(3-(2-(3-chloro-4-(4-(2-hydroxyethyl)piperazin-1-yl)phenylamino)-5-methoxypyrimidin-4-ylamino)phenyl)cyclopropanecarbonitrile (Compound 9)

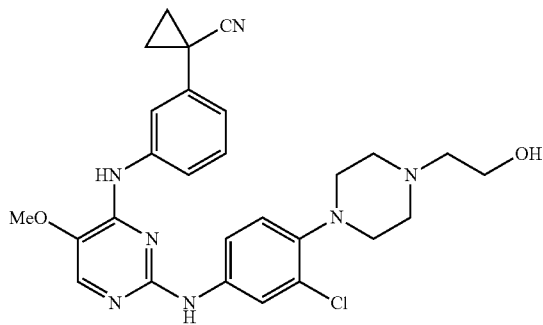 [SMILES: COc1cnc(Nc2ccc(N3CCN(CCO)CC3)c(Cl)c2)nc1Nc1cccc(C2(C#N)CC2)c1]

The title compound was synthesized following the procedure depicted in scheme 9.

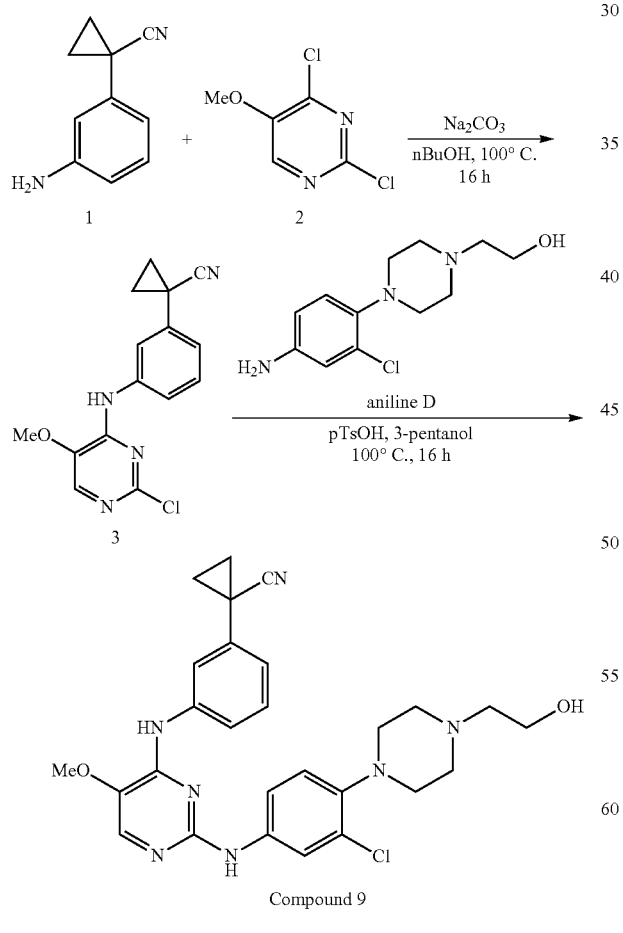

A mixture of scheme 9 compound 1 (400 mg, 2.53 mmol), scheme 9 compound 2 (678 mg, 3.79 mmol) and Na₂CO₃ (804 mg, 7.59 mmol) in nBuOH (10 mL) was heated to 100° C. for 16 h in a sealed tube. After TLC showed the starting material was consumed completely, the reaction mixture was diluted with water (20 mL) and extracted with EtOAc (2×20 mL). The organic layer was dried over Na₂SO₄, filtered and concentrated to give a residue which was purified by flash chromatography on neutral alumina (eluting with petroleum ether/EtOAc 100/0 gradually increasing to 60/40) to give scheme 9 compound 3 (180 mg, 27% yield) as an off-white solid. ¹H NMR (400 MHz, CD₃OD): δ 8.96 (d, J=8.6 Hz, 1H), 8.72-8.63 (m, 1H), 8.51 (d, J=8.2 Hz, 1H), 7.96 (m, 2H), 7.42 (m, 1H), 7.28 (d, J=2.3 Hz, 1H), 7.18 (d, J=8.5 Hz, 1H), 7.08 (m, 1H), 6.95 (d, J=8.6 Hz, 1H), 6.28 (d, J=5.9 Hz, 1H), 3.79 (s, 3H), 3.15 (s, 4H), 2.93 (s, 4H), 2.56 (d, J=8.0 Hz, 6H). MS [ESI, MH⁺]=301.05.

A mixture of scheme 9 compound 3 (180 mg, 0.59 mmol), aniline D (183 mg, 0.72 mmol) and pTsOH (100 mg, 0.59 mmol) in 3-pentanol (10 mL) was heated to 100° C. for 16 h. After TLC showed the starting material was consumed completely, the reaction mixture was diluted with water (20 mL), neutralized with aqueous NaHCO₃ (pH 8) and extracted with EtOAc (2×20 mL). The organic layer was dried over Na₂SO₄, filtered and concentrated to give a residue which was purified by flash chromatography on neutral alumina (eluting with CH₂Cl₂/MeOH 100/0 gradually increasing to 90/10) to give Compound 9 (100 mg, 32% yield) as an off-white solid. ¹H NMR (400 MHz, DMSO-d₆): δ 8.96 (s, 1H), 8.85 (s, 1H), 8.02 (d, J=8.0 Hz, 1H), 7.88 (d, J=2.4 Hz, 2H), 7.54 (t, J=2.0 Hz, 1H), 7.48 (m, 1H), 7.34 (t, J=7.9 Hz, 1H), 7.05-6.97 (m, 2H), 4.41 (t, J=5.3 Hz, 1H), 3.86 (s, 3H), 3.52 (d, J=6.0 Hz, 2H), 2.89 (t, J=4.6 Hz, 4H), 2.56 (s, 4H), 2.44 (t, J=6.2 Hz, 2H), 1.72 (d, J=4.9 Hz, 2H), 1.58-1.30 (m, 2H). MS [ESI, MH⁺]=520.12.

Preparation of 2-(4-(4-(4-(2,2'-bipyridin-3-ylamino)pyrimidin-2-ylamino)-2-chlorophenyl)piperazin-1-yl)ethanol (Compound 10)

The title compound was synthesized following the procedure depicted in scheme 10. The preparation of 2,2'-bipyridin-3-amine (scheme 10 compound 1) is described below in scheme 11.

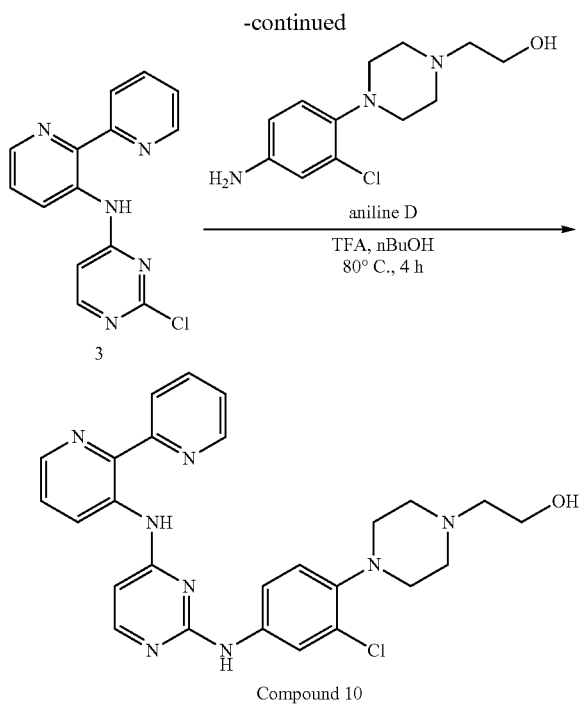

Compound 10

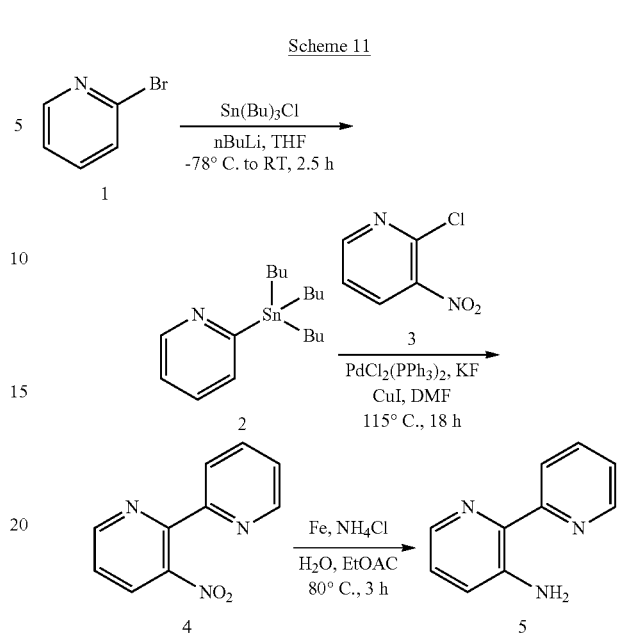

Scheme 11

A mixture of scheme 10 compound 1 (400 mg, 2.33 mmol), scheme 10 compound 2 (410 mg, 2.80 mmol) and $Na_2CO_3$ (500 mg, 4.68 mmol) in nBuOH (5 mL) was heated to 80° C. for 24 h in a sealed tube. After TLC showed the starting material was consumed completely, the reaction mixture was diluted with water (20 mL) and extracted with EtOAc (2×20 mL). The organic layer was dried over $Na_2SO_4$, filtered and concentrated to give a residue which was purified by flash chromatography on neutral alumina (eluting with $CH_2Cl_2$/MeOH 100/0 gradually increasing to 80/20) to give scheme 10 compound 3 (320 mg, 48% yield) as an off-white solid. $^1$H NMR (400 MHz, DMSO-$d_6$): δ 13.16 (s, 1H), 8.86 (dd, J=8.4, 1.6 Hz, 1H), 8.82-8.76 (m, 1H), 8.53 (d, J=8.2 Hz, 1H), 8.48-8.40 (m, 1H), 8.29 (d, J=5.8 Hz, 1H), 8.07 (m, 1H), 7.65-7.49 (m, 2H), 7.13 (d, J=5.9 Hz, 1H). MS [ESI, MH$^+$]=284.07.

A mixture of scheme 10 compound 3 (150 mg, 0.53 mmol), aniline D (148 mg, 0.58 mmol) and TFA (2 mL) in nBuOH (5 mL) was heated to 80° C. for 4 h. After TLC showed the starting material was consumed completely, the reaction mixture was diluted with water (20 mL), neutralized with aqueous $NaHCO_3$ (pH 8) and extracted with EtOAc (2×20 mL). The organic layer was dried over $Na_2SO_4$, filtered and concentrated to give a residue which was purified by flash chromatography on neutral alumina (eluting with $CH_2Cl_2$/MeOH=100/0 gradually increasing to 90/10) to give Compound 10 (50 mg, 19% yield) as an off-white solid. $^1$H NMR (400 MHz, DMSO-$d_6$): δ 12.88 (s, 1H), 9.39 (s, 1H), 9.14 (s, 1H), 8.88-8.73 (m, 1H), 8.58 (d, J=8.2 Hz, 1H), 8.37 (dd, J=4.4, 1.5 Hz, 1H), 8.15 (d, J=5.6 Hz, 1H), 8.09-8.00 (m, 1H), 7.95 (d, J=2.3 Hz, 1H), 7.61-7.38 (m, 3H), 7.11 (d, J=8.7 Hz, 1H), 6.50 (d, J=5.7 Hz, 1H), 5.76 (s, 1H), 4.43 (t, J=5.3 Hz, 1H), 3.53 (d, J=6.1 Hz, 2H), 2.93 (s, 4H), 2.58 (s, 4H), 2.47 (d, J=9.4 Hz, 2H). MS [ESI, MH$^+$]=503.10.

2,2'-Bipyridin-3-amine (scheme 10 compound 1) was synthesized as shown in scheme 11.

nBuLi (1.6 M in hexane, 7.9 mL, 12.7 mmol) was added to a cold (−78° C.) solution of scheme 11 compound 1 (2.00 g, 12.7 mmol) in dry THF (20 mL). Following 30 min of stirring, tributyltin chloride (4.14 g, 12.7 mmol) was added dropwise and the resulting solution was stirred for 1 h at −78° C. after which time it was allowed to warm to RT and stirred for an additional 1 h. After TLC showed the starting material was consumed completely, the reaction mixture was quenched with aqueous $NH_4Cl$ (20 mL) and extracted with $Et_2O$ (50 mL) then dried over $Na_2SO_4$ and concentrated to give a residue which was purified by flash chromatography on neutral alumina (eluting with petroleum ether/EtOAc 100/0 gradually increasing to 80/20) to give scheme 11 compound 2 (3.20 g, 68% yield) as a brown liquid. $^1$H NMR (400 MHz, CDCl$_3$): δ 8.73 (d, J=4.7 Hz, 1H), 7.49 (m, 1H), 7.40 (d, J=7.6 Hz, 1H), 7.16-7.04 (m, 1H), 1.56 (t, J=7.7 Hz, 6H), 1.33 (d, J=7.3 Hz, 6H), 1.18-1.08 (m, 6H), 0.88 (t, J=7.3 Hz, 9H). MS [ESI, MH$^+$]=370.12.

PdCl$_2$(PPh$_3$)$_3$ (27 mg, 0.04 mmol) was added to a stirred degassed solution of scheme 11 compound 2 (1.56 g, 4.23 mmol), scheme 11 compound 3 (600 mg, 3.84 mmol) and CuI (7.3 mg, 0.038 mmol) in dry DMF (20 mL) and the resulting mixture was heated to 115° C. for 18 h in a sealed tube. After TLC showed the starting material was consumed completely, the reaction mixture was cooled to RT, quenched with 1 N aqueous KF (6 mL) and stirred for 30 min. The solids were removed by filtration over a pad of Celite and washed with $Et_2O$ (20 mL). The filtrate was concentrated to give a residue which was purified by flash chromatography on neutral alumina (eluting with petroleum ether/EtOAc 100/0 gradually increasing to 50/50) to give scheme 11 compound 4 (400 mg, 52% yield) as a brown solid. $^1$H NMR (400 MHz, CDCl$_3$): δ 8.84 (m, 1H), 8.70-8.52 (m, 1H), 8.08 (m, 2H), 7.89 (m, 1H), 7.49 (m, 1H), 7.37 (m, 1H). MS [ESI, MH$^+$]=202.06.

Scheme 11 compound 4 (400 mg, 1.99 mmol), Fe (445 mg, 7.96 mmol) and $NH_4Cl$ (1.06 g, 19.90 mmol) were dissolved in EtOAc/water (20 mL, 1/1) and stirred at 80° C. for 3 h. After TLC showed the starting material was consumed completely, the reaction mixture was cooled to RT and filtered through a pad of celite. The solids were washed with EtOAc (20 mL) and the filtrate was concentrated to give a residue which was purified by flash chromatography on neutral alumina (eluting with petroleum ether/EtOAc 100/0 gradually increasing to 0/100) to give scheme 11 compound 5 (260 mg, 77% yield) as an off-white solid. $^1$H NMR (400 MHz, DMSO-d$_6$): δ 8.65-8.58 (m, 1H), 8.44 (d, J=8.2 Hz, 1H), 7.91 (d, J=3.9 Hz, 2H), 7.40-7.28 (m, 1H), 7.23 (s, 2H), 7.15 (m, 2H). MS [ESI, MH$^+$]=172.08.

Preparation of N$^4$-(2,2'-bipyridin-3-yl)-N$^2$-(3-methoxy-4-(4-methylpiperazin-1-yl)phenyl)pyrimidine-2,4-diamine (Compound 11)

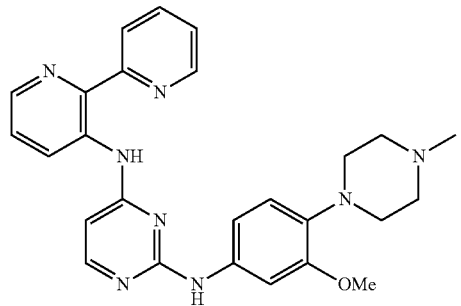 [SMILES: COc1cc(Nc2nccc(Nc3cccnc3-c3ccccn3)n2)ccc1N1CCN(C)CC1]

The title compound was synthesized in a similar manner as Compound 10 using 3-methoxy-4-(4-methylpiperazin-1-yl)aniline in the final coupling step.

A mixture of scheme 10 compound 3 (150 mg, 0.543 mmol), aniline B (160 mg, 0.630 mmol) and TFA (1.5 mL) in nBuOH (5 mL) was heated to 80° C. for 12 h. After TLC showed the starting material was consumed completely, the reaction mixture was diluted with water (20 mL), neutralized with aqueous NaHCO$_3$ (pH 8) and extracted with EtOAc (2×20 mL). The organic layer was dried over Na$_2$SO$_4$, filtered and concentrated to give a residue which was purified by flash chromatography on neutral alumina (eluting with CH$_2$Cl$_2$/MeOH 100/0 gradually increasing to 90/10) to give Compound 11 (60 mg, 24% yield) as an off-white solid. $^1$H NMR (400 MHz, DMSO-d$_6$): δ 12.87 (s, 1H), 9.24 (d, J=7.5 Hz, 1H), 9.18 (s, 1H), 8.79 (d, J=4.4 Hz, 1H), 8.58 (d, J=8.3 Hz, 1H), 8.36 (dd, J=4.4, 1.6 Hz, 1H), 8.12 (d, J=5.7 Hz, 1H), 8.04-8.08 (m, 1H), 7.55 (m, 1H), 7.40-7.30 (m, 1H), 7.27 (d, J=8.8 Hz, 1H), 6.84 (d, J=8.3 Hz, 1H), 6.45 (d, J=5.7 Hz, 1H), 3.72 (s, 3H), 2.98 (m, 4H), 2.67-2.55 (m, 4H), 2.36 (s, 3H). MS [ESI, MH$^+$]=470.25.

Preparation of N$^4$-(2,2'-bipyridin-3-yl)-N$^2$-(3,4,5-trimethoxyphenyl)pyrimidine-2,4-diamine (Compound 12)

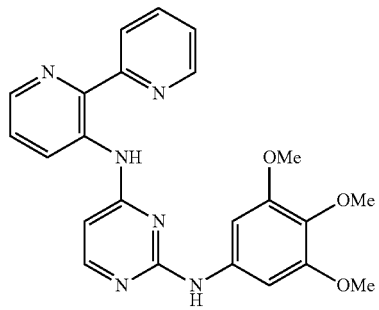 [SMILES: COc1cc(Nc2nccc(Nc3cccnc3-c3ccccn3)n2)cc(OC)c1OC]

The title compound was synthesized in a similar manner as Compound 10 using 3,4,5-trimethoxyaniline in the final coupling step.

A mixture of scheme 10 compound 3 (150 mg, 0.53 mmol), 3,4,5-trimethoxyaniline (116 mg, 0.630 mmol) and TFA (1 mL) in nBuOH (5 mL) was heated to 80° C. for 4 h. After TLC showed the starting material was consumed completely, the reaction mixture was diluted with water (20 mL), neutralized with aqueous NaHCO$_3$ (pH 8) and extracted with EtOAc (2×20 mL). The organic layer was dried over Na$_2$SO$_4$, filtered and concentrated to give a residue which was purified by flash chromatography on neutral alumina (eluting with CH$_2$Cl$_2$/MeOH 100/0 gradually increasing to 90/10) to give Compound 12 (50 mg, 22% yield) as an off-white solid. $^1$H NMR (400 MHz, DMSO-d$_6$): δ 12.91 (s, 1H), 9.25 (d, J=12.3 Hz, 2H), 8.79 (dd, J=4.9, 1.8 Hz, 1H), 8.58 (d, J=8.1 Hz, 1H), 8.36 (dd, J=4.4, 1.6 Hz, 1H), 8.15 (d, J=5.7 Hz, 1H), 8.06 (m, 1H), 7.55 (m, 1H), 7.40 (dd, J=8.6, 4.4 Hz, 1H), 7.13 (s, 2H), 6.49 (d, J=5.7 Hz, 1H), 3.72 (s, 6H), 3.63 (s, 3H). MS [ESI, MH$^+$]=430.18.

Preparation of 2-(4-(4-(4-(2,2'-bipyridin-3-ylamino)-5-methoxypyrimidin-2-ylamino)-2-chlorophenyl)piperazin-1-yl)ethanol (Compound 13)

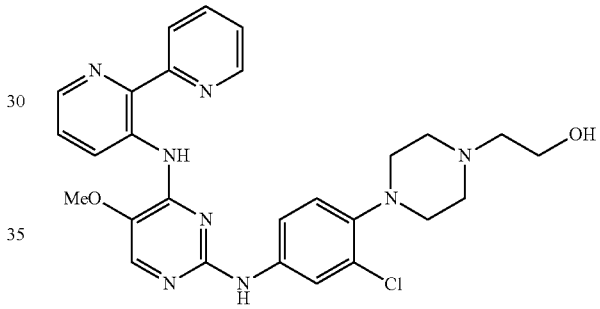

The title compound was synthesized following the procedure depicted in scheme 12.

Scheme 12

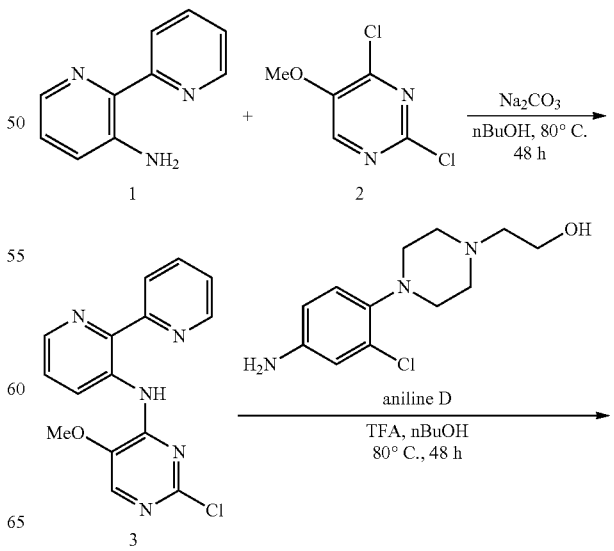

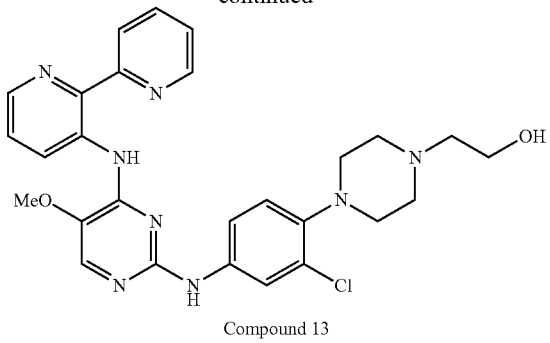

Compound 13

A mixture of scheme 12 compound 1 (400 mg, 2.33 mmol), scheme 12 compound 2 (502 mg, 2.80 mmol) and Na₂CO₃ (493 mg, 4.66 mmol) in nBuOH (5 mL) was heated to 80° C. for 48 h in a sealed tube. After TLC showed the starting material was consumed completely, the reaction mixture was diluted with water (20 mL) and extracted with EtOAc (2×20 mL). The organic layer was dried over Na₂SO₄, filtered and concentrated to give a residue which was purified by flash chromatography on neutral alumina (eluting with CH₂Cl₂/MeOH 100/0 gradually increasing to 80/20) to give scheme 12 compound 3 (200 mg, 27% yield) as a brown solid. $^1$H NMR (400 MHz, DMSO-$d_6$): δ 13.95 (s, 1H), 9.20 (d, J=8.4 Hz, 1H), 8.79 (d, J=4.7 Hz, 1H), 8.60 (d, J=8.1 Hz, 1H), 8.43 (d, J=4.4 Hz, 1H), 8.08 (d, J=6.8 Hz, 2H), 7.57 (dd, J=8.0, 4.6 Hz, 2H), 4.10 (s, 3H). MS [ESI, MH⁺]=314.08.

A mixture of scheme 12 compound 3 (200 mg, 0.63 mmol), aniline D (178 mg, 0.70 mmol) and TFA (2 mL) in nBuOH (5 mL) was heated to 80° C. for 48 h. After TLC showed the starting material was consumed completely, the reaction mixture was diluted with water (20 mL), neutralized with aqueous NaHCO₃ (pH 8) and extracted with EtOAc (2×20 mL). The organic layer was dried over Na₂SO₄, filtered and concentrated to give a residue which was purified by flash chromatography on neutral alumina (eluting with CH₂Cl₂/MeOH 100/0 gradually increasing to 90/10) to give Compound 13 (100 mg, 30% yield) as an off-white solid. $^1$H NMR (400 MHz, DMSO-$d_6$): δ 13.48 (s, 1H), 9.48 (m, 1H), 9.17 (s, 1H), 8.95-8.65 (m, 1H), 8.70-8.48 (m, 1H), 8.38 (m, 1H), 8.08 (m, 1H), 7.99 (d, J=2.5 Hz, 1H), 7.97 (s, 1H), 7.55 (m, 1H), 7.48 (m, 2H), 7.10 (d, J=8.8 Hz, 1H), 4.43 (t, J=5.3 Hz, 1H), 4.00 (s, 3H), 3.53 (d, J=6.0 Hz, 2H), 2.92 (t, J=4.5 Hz, 4H), 2.56 (d, J=15.6 Hz, 4H), 2.45 (t, J=6.3 Hz, 2H). MS [ESI, MH⁺]=533.21.

Preparation of N⁴-([2,2'-bipyridin]-3-yl)-5-methoxy-N²-(3-methoxy-4-(4-methylpiperazin-1-yl)phenyl)pyrimidine-2,4-diamine (Compound 14)

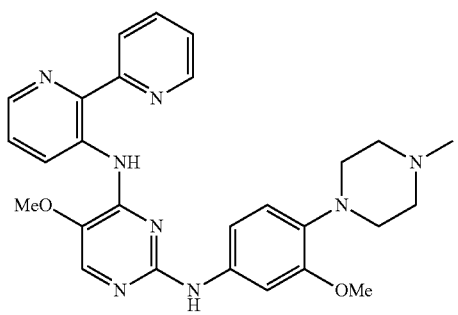 [SMILES: COc1cc(Nc2ncc(OC)c(Nc3cccnc3-c3ccccn3)n2)ccc1N1CCN(C)CC1]

The title compound was synthesized in a similar manner as Compound 13 using aniline B in the final coupling step.

A mixture of scheme 12 compound 3 (130 mg, 0.41 mmol), aniline B (125 mg, 0.49 mmol) and TFA (1.5 mL) in nBuOH (5 mL) was heated to 80° C. for 12 h. After TLC showed the starting material was consumed completely, the reaction mixture was diluted with water (20 mL), neutralized with aqueous NaHCO₃ (pH 8) and extracted with EtOAc (2×20 mL). The organic layer was dried over Na₂SO₄, filtered and concentrated to give a residue which was purified by flash chromatography on neutral alumina (eluting with CH₂Cl₂/MeOH=100/0 gradually increasing to 90/10) to give Compound 14 (40 mg, 20% yield) as an off-white solid. $^1$H NMR (400 MHz, DMSO-$d_6$): δ 13.45 (s, 1H), 9.61-9.47 (m, 1H), 8.92 (s, 1H), 8.82-8.71 (m, 1H), 8.60 (d, J=8.2 Hz, 1H), 8.37 (m, 1H), 8.07 (m, 1H), 7.93 (s, 1H), 7.55 (m, 1H), 7.43 (m, 1H), 7.34 (d, J=2.4 Hz, 1H), 7.26 (m, 1H), 6.81 (d, J=8.5 Hz, 1H), 3.99 (s, 3H), 3.74 (s, 3H), 2.92 (s, 4H), 2.46 (s, 4H), 2.22 (s, 3H). MS [ESI, MH⁺]=499.13.

Preparation of 2-(4-(2-chloro-4-(4-(6-methyl-2,2'-bipyridin-3-ylamino)pyrimidin-2-ylamino)phenyl)piperazin-1-yl)ethanol (Compound 15)

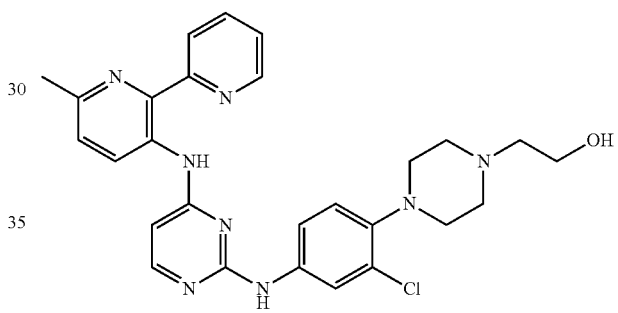

The title compound was synthesized following the procedure depicted in scheme 13. The preparation of 6-methyl-2,2'-bipyridin-3-amine (scheme 13 compound 1) is described below.

Scheme 13

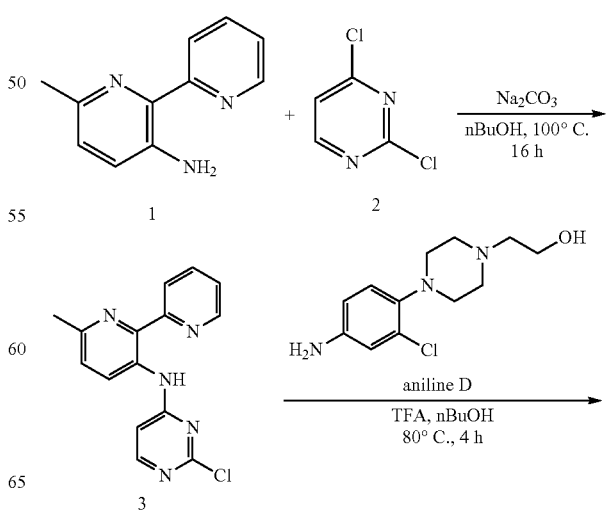

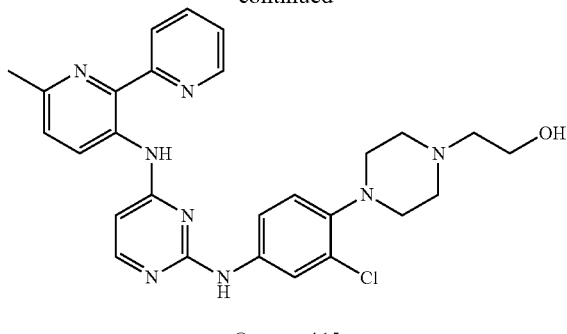

Compound 15

A mixture of scheme 13 compound 1 (400 mg, 2.18 mmol), scheme 13 compound 2 (488 mg, 3.27 mmol) and Na$_2$CO$_3$ (462 mg, 4.36 mmol) in nBuOH (10 mL) was heated to 100° C. for 16 h in a sealed tube. After TLC showed the starting material was consumed completely, the reaction mixture was diluted with water (20 mL) and extracted with EtOAc (2×20 mL). The organic layer was dried over Na$_2$SO$_4$, filtered and concentrated to give a residue which was purified by flash chromatography on neutral alumina (eluting with petroleum ether/EtOAc 100/0 gradually increasing to 60/40) to give scheme 13 compound 3 (230 mg, 35% yield) as an off-white solid. $^1$H NMR (400 MHz, DMSO-d$_6$): δ12.88 (s, 1H), 8.75 (m, 1H), 8.69 (d, J=8.5 Hz, 1H), 8.49 (m, 1H), 8.24 (d, J=5.8 Hz, 1H), 8.05 (m, 1H), 7.52 (m, 1H), 7.40 (d, J=8.6 Hz, 1H), 7.07 (d, J=5.9 Hz, 1H), 2.54 (s, 3H). MS [ESI, MH$^+$]=298.08.

A mixture of scheme 13 compound 3 (200 mg, 0.67 mmol), aniline D (188 mg, 0.74 mmol) and TFA (2 mL) in nBuOH (5 mL) was heated to 80° C. for 4 h. After TLC showed the starting material was consumed completely, the reaction mixture was diluted with water (20 mL), neutralized with aqueous NaHCO$_3$ (pH 8) and extracted with EtOAc (2×20 mL). The organic layer was dried over Na$_2$SO$_4$, filtered and concentrated to give a residue which was purified by flash chromatography on neutral alumina (eluting with CH$_2$Cl$_2$/MeOH 100/0 gradually increasing to 90/10) to give Compound 15 (50 mg, 15% yield) as an off-white solid. $^1$H NMR (400 MHz, DMSO-d$_6$): δ 12.62 (s, 1H), 9.35 (s, 1H), 8.97 (d, J=8.4 Hz, 1H), 8.77 (d, J=4.7 Hz, 1H), 8.55 (d, J=8.2 Hz, 1H), 8.11 (d, J=5.7 Hz, 1H), 8.04 (t, J=7.7 Hz, 1H), 7.96 (d, J=2.6 Hz, 1H), 7.51 (m, 2H), 7.32 (d, J=8.6 Hz, 1H), 7.10 (d, J=8.7 Hz, 1H), 6.45 (d, J=5.8 Hz, 1H), 4.44 (t, J=5.4 Hz, 1H), 3.54 (d, J=6.0 Hz, 2H), 2.93 (s, 4H), 2.56 (d, J=16.1 Hz, 7H), 2.46 (t, J=9.0 Hz, 2H). MS [ESI, MH$^+$]=517.08.

6-Methyl-2,2'-bipyridin-3-amine (scheme 13 compound 1) was synthesized in a manner similar to scheme 11 compound 5 using 2-chloro-6-methyl-3-nitropyridine in the second step and was isolated as a brown solid (700 mg, 32% yield over 2 steps from scheme 11 compound 2). $^1$H NMR (400 MHz, DMSO-d$_6$): δ 8.76-8.66 (m, 1H), 8.65-8.55 (m, 1H), 8.44 (d, J=8.2 Hz, 1H), 8.40 (d, J=8.1 Hz, 1H), 7.99-7.92 (m, 1H), 7.92-7.86 (m, 1H), 7.47 (m, 1H), 7.35-7.27 (m, 1H), 7.11 (d, J=8.3 Hz, 1H), 7.05 (s, 2H), 7.01 (d, J=8.4 Hz, 1H), 2.38 (s, 3H). MS [ESI, MH$^+$]=186.09.

Preparation of N$^2$-(3-methoxy-4-(4-methylpiperazin-1-yl)phenyl)-N$^4$-(6-methyl-2,2'-bipyridin-3-yl)pyrimidine-2,4-diamine (Compound 16)

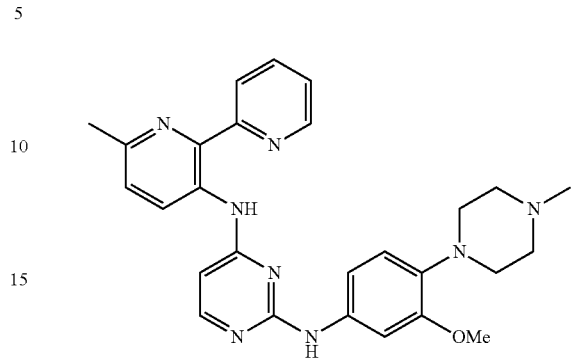

The title compound was synthesized in a similar manner as Compound 15 using aniline B in the final coupling step.

A mixture of scheme 13 compound 3 (90 mg, 0.30 mmol), aniline B (114 mg, 0.45 mmol) and TFA (1 mL) in nBuOH (5 mL) was heated to 80° C. for 12 h. After TLC showed the starting material was consumed completely, the reaction mixture was diluted with water (20 mL), neutralized with aqueous NaHCO$_3$ (pH 8) and extracted with EtOAc (2×20 mL). The organic layer was dried over Na$_2$SO$_4$, filtered and concentrated to give a residue which was purified by flash chromatography on neutral alumina (eluting with CH$_2$Cl$_2$/MeOH 100/0 gradually increasing to 90/10) to give Compound 16 (35 mg, 24% yield) as an off-white solid. $^1$H NMR (400 MHz, CD$_3$OD): δ 8.96 (d, J=8.6 Hz, 1H), 8.72-8.63 (m, 1H), 8.51 (d, J=8.2 Hz, 1H), 7.96 (m, 2H), 7.42 (m, 1H), 7.28 (d, J=2.3 Hz, 1H), 7.18 (d, J=8.5 Hz, 1H), 7.08 (m, 1H), 6.95 (d, J=8.6 Hz, 1H), 6.28 (d, J=5.9 Hz, 1H), 3.79 (s, 3H), 3.15 (s, 4H), 2.93 (s, 4H), 2.56 (d, J=8.0 Hz, 6H). MS [ESI, MH$^+$]=482.01.

Preparation of N$^4$-(6-methyl-2,2'-bipyridin-3-yl)-N$^2$-(3,4,5-trimethoxyphenyl)pyrimidine-2,4-diamine (Compound 17)

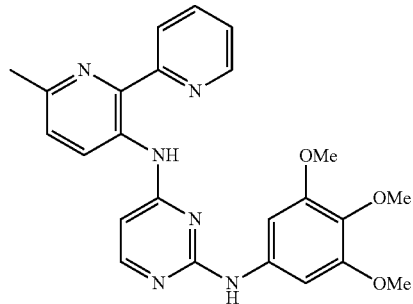 [SMILES: COc1cc(Nc2nccc(Nc3ccc(C)nc3-c3ccccn3)n2)cc(OC)c1OC]

The title compound was synthesized in a similar manner as Compound 15 using 3,4,5-trimethoxyaniline in the final coupling step A mixture of scheme 13 compound 3 (90 mg, 0.30 mmol), 3,4,5-trimethoxyaniline (55 mg, 0.30 mmol) and TFA (1 mL) in nBuOH (5 mL) was heated to 80° C. for 6 h. After TLC showed the starting material was consumed completely, the reaction mixture was diluted with water (20 mL), neutralized with aqueous NaHCO$_3$ (pH 8) and extracted with EtOAc (2×20 mL). The organic layer was dried over Na$_2$SO$_4$, filtered and concentrated to give a residue which was purified by flash chromatography on neutral alumina (eluting with CH$_2$Cl$_2$/MeOH 100/0 gradually increasing to 90/10) to give Compound 17 (24 mg, 19% yield) as an off-white solid. $^1$H NMR (400 MHz, DMSO-d$_6$): δ 12.67 (s, 1H), 9.19 (s, 1H), 9.07 (d, J=8.4 Hz, 1H), 8.81-8.68 (m, 1H), 8.56 (d, J=8.1 Hz, 1H), 8.12 (d, J=5.7 Hz, 1H), 8.07-7.98 (m, 1H), 7.58-7.44 (m, 1H), 7.26 (d, J=8.6 Hz, 1H), 7.12 (s, 2H), 6.44 (d, J=5.6 Hz, 1H), 3.71 (s, 6H), 3.63 (s, 3H), 2.54 (s, 3H). MS [ESI, MH$^+$]=445.12.

Preparation of 2-(2-(2-(3-chloro-4-(4-(2-hydroxyethyl)piperazin-1-yl)phenylamino)pyrimidin-4-ylamino)-5-methylphenyl)acetonitrile (Compound 18)

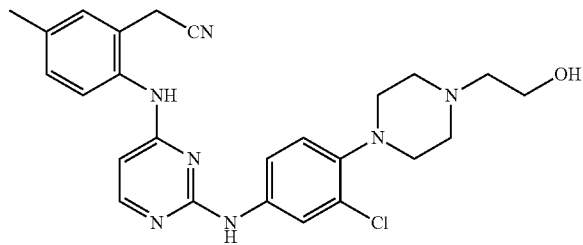 [SMILES: Cc1ccc(Nc2ccnc(Nc3ccc(N4CCN(CCO)CC4)c(Cl)c3)n2)c(CC#N)c1]

The title compound was synthesized following the procedure depicted in scheme 14. The preparation of 2-(2-amino-5-methylphenyl)acetonitrile (scheme 14 compound 1) is described in scheme 15 below.

A mixture of scheme 14 compound 1 (420 mg, 2.87 mmol), scheme 14 compound 2 (640 mg, 4.31 mmol) and Na$_2$CO$_3$ (608 mg, 5.74 mmol) in nBuOH (10 mL) was heated to 100° C. for 48 h in a sealed tube. After TLC showed the starting material was consumed completely, the reaction mixture was diluted with water (20 mL) and extracted with EtOAc (2×20 mL). The organic layer was dried over Na$_2$SO$_4$, filtered and concentrated to give a residue which was purified by flash chromatography on neutral alumina (eluting with petroleum ether/EtOAc 100/0 gradually increasing to 60/40) to give scheme 14 compound 3 (200 mg, 27% yield) as a brown solid. $^1$H NMR (400 MHz, DMSO-d$_6$): δ 9.62 (s, 1H), 8.10 (d, J=5.9 Hz, 1H), 7.47-7.00 (m, 3H), 6.53 (s, 1H), 3.90 (s, 2H), 2.34 (s, 3H). MS [ESI, MH$^+$]=259.07

A mixture of scheme 14 compound 3 (180 mg, 0.69 mmol), aniline D (195 mg, 0.76 mmol) and TFA (2 mL) in nBuOH (8 mL) was heated to 80° C. for 6 h. After TLC showed the starting material was consumed completely, the reaction mixture was diluted with water (20 mL), neutralized with aqueous NaHCO$_3$ (pH 8) and extracted with EtOAc (2×20 mL). The organic layer was dried over Na$_2$SO$_4$, filtered and concentrated to give a residue which was purified by prep-HPLC to give Compound 18 (50 mg, 15% yield) as an off-white solid. $^1$H NMR (400 MHz, DMSO-d$_6$): δ 9.07 (s, 1H), 8.89 (s, 1H), 7.97 (d, J=5.5 Hz, 1H), 7.79 (d, J=2.7 Hz, 1H), 7.50-7.36 (m, 1H), 7.30 (d, J=8.4 Hz, 2H), 7.20 (m, 1H), 6.94 (d, J=8.7 Hz, 1H), 6.10 (d, J=5.8 Hz, 1H), 4.44 (s, 1H), 3.90 (s, 2H), 3.52 (d, J=5.8 Hz, 2H), 2.87 (s, 3H), 2.50 (d, J=1.7 Hz, 6H), 2.35 (s, 3H). MS [ESI, MH$^+$]=478.10.

2-(2-Amino-5-methylphenyl)acetonitrile (Scheme 14 Compound 1) was Synthesized as Shown in Scheme 15.

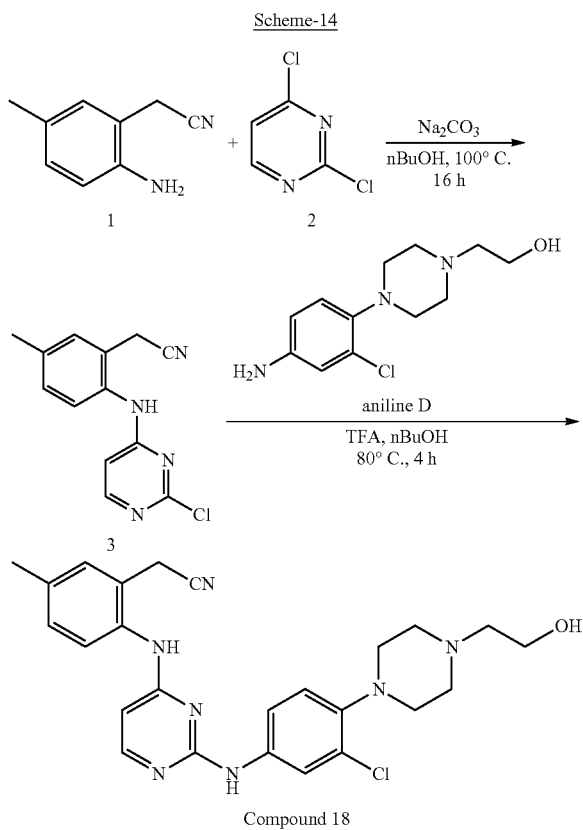

Compound 18

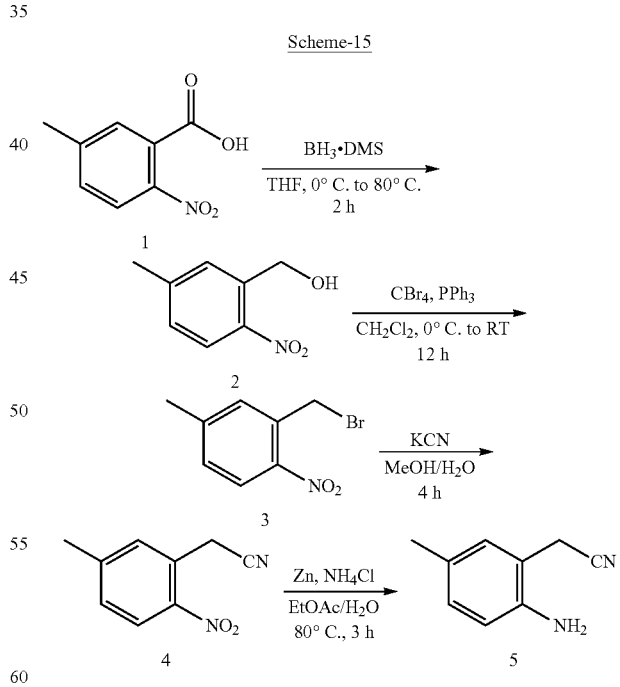

To a cold (0° C.) stirred solution of scheme 15 compound 1 (5.0 g, 27.6 mmol) in dry THF (20 mL) was added BH$_3$.DMS (1M in THF, 110 mL, 110.0 mmol) dropwise and the reaction mixture was stirred at 80° C. for 2 h. After TLC showed the starting material was consumed completely, the reaction mixture was diluted with ice water (30 mL) and extracted with EtOAc (2×50 mL). The organic layer was washed with brine (20 mL), dried over Na$_2$SO$_4$ and concentrated to give a residue which was purified by flash chromatography on silica gel (eluting with petroleum ether/EtOAc 100/0 gradually increasing to 30/70) to give scheme 15 compound 2 (3.5 g, 76% yield) as an off-white solid. $^1$H NMR (400 MHz, DMSO-d$_6$): δ 7.97 (d, J=8.3 Hz, 1H), 7.65 (d, J=2.3 Hz, 1H), 7.37-7.14 (m, 1H), 5.53 (s, 1H), 4.81 (s, 2H), 2.43 (s, 3H). MS [ESI, MH$^+$]=168.06.

To a cold (0° C.) stirred solution of scheme 15 compound 2 (1.0 g, 5.98 mmol) in dry CH$_2$Cl$_2$ (10 mL) was added PPh$_3$ (2.5 g, 9.76 mmol) and CBr$_4$ (3.2 g, 9.76 mmol) and the reaction mixture was stirred at RT for 12 h. After TLC showed the starting material was consumed completely, the reaction mixture was concentrated under reduced pressure to give a residue which was purified by flash chromatography on silica gel (eluting with petroleum ether/EtOAc 100/0 gradually increasing to 60/40) to give scheme 16 compound 3 (900 mg, 69% yield) as a brown liquid. $^1$H NMR (400 MHz, CDCl$_3$): δ 7.99 (d, J=8.3 Hz, 1H), 7.35 (d, J=1.9 Hz, 1H), 7.28 (d, J=1.9 Hz, 1H), 4.83 (s, 2H), 2.45 (s, 3H). MS [ESI, MH$^+$]=229.98.

To a solution of scheme 15 compound 3 (900 mg, 3.9 mmol) in MeOH/water (8 mL, 3/1) was added KCN (330 mg, 5.1 mmol) and the reaction mixture was stirred at RT for 4 h. After TLC showed the starting material was consumed completely, the reaction mixture was diluted with water (20 mL) and extracted with EtOAc (30 mL). The organic layer was dried over Na$_2$SO$_4$, filtered and concentrated to give a residue which was purified by flash chromatography on silica gel (eluting with petroleum ether/EtOAc 100/0 gradually increasing to 40/60) to give scheme 15 compound 4 (350 mg, 51% yield) as an off-white solid. $^1$H NMR (400 MHz, CDCl$_3$): δ 8.13 (d, J=8.4 Hz, 1H), 7.62-7.46 (m, 1H), 7.41-7.30 (m, 1H), 4.21 (s, 2H), 2.50 (s, 3H). MS [ESI, MH$^+$]=177.06.

A mixture of scheme 15 compound 4 (350 mg, 1.98 mmol), Zn dust (297 mg, 4.54 mmol) and NH$_4$Cl (607 g, 11.36 mmol) in EtOAc/H$_2$O (10 mL, 1/1) was heated to 80° C. for 3 h. After TLC showed the starting material was consumed completely, the reaction mixture was passed through a pad of celite and the solids were washed with EtOAc. The filtrate was evaporated under reduced pressure to give a residue which was purified by flash chromatography on silica gel (eluting with petroleum ether/EtOAc 100/0 gradually increasing to 60/40) to give scheme 15 compound 5 (220 mg, 76% yield) as a brown solid. $^1$H NMR (400 MHz, DMSO-d$_6$): δ 6.91 (d, J=2.2 Hz, 1H), 6.84 (dd, J=8.1, 2.1 Hz, 1H), 6.59 (d, J=8.0 Hz, 1H), 4.93 (s, 2H), 3.73 (s, 2H), 2.15 (s, 3H). MS [ESI, MH$^+$]=147.09.

Preparation of 2-(2-(2-(3-methoxy-4-(4-methylpiperazin-1-yl)phenylamino)pyrimidin-4-ylamino)-5-methylphenyl)acetonitrile (Compound 19)

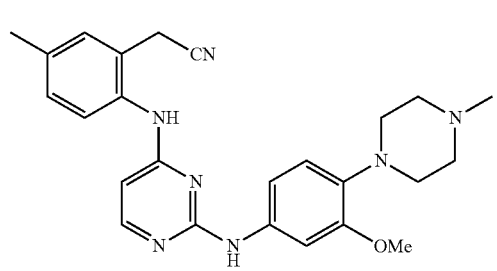

The title compound was synthesized in a similar manner as Compound 18 using aniline B in the final coupling step.

A mixture of scheme 14 compound 3 (170 mg, 0.65 mmol), aniline B (125 mg, 0.78 mmol) and TFA (1 mL) in nBuOH (5 mL) was heated to 80° C. for 3 h. After TLC showed the starting material was consumed completely, the reaction mixture was diluted with water (20 mL), neutralized with aqueous NaHCO$_3$ (pH 8) and extracted with EtOAc (2×20 mL). The organic layer was dried over Na$_2$SO$_4$, filtered and concentrated to give a residue which was purified by flash chromatography on neutral alumina (eluting with CH$_2$Cl$_2$/MeOH 100/0 gradually increasing to 90/10) to give Compound 19 (25 mg, 9% yield) as an off-white solid. $^1$H NMR (400 MHz, CDCl$_3$): δ 8.00 (d, J=5.8 Hz, 1H), 7.34 (s, 1H), 7.19 (dd, J=8.2, 1.8 Hz, 3H), 6.98 (dd, J=8.4, 2.4 Hz, 1H), 6.92-6.79 (m, 2H), 6.28 (s, 1H), 5.80 (d, J=5.7 Hz, 1H), 3.78 (s, 3H), 3.68 (s, 2H), 3.11 (s, 4H), 2.72 (s, 4H), 2.43 (s, 3H), 2.41 (s, 3H). MS [ESI, MH$^+$]=444.12.

Preparation of 2-(2-(2-(3-chloro-4-(4-(2-hydroxyethyl)piperazin-1-yl)phenylamino)pyrimidin-4-ylamino)-5-methylphenyl)acetonitrile (Compound 20)

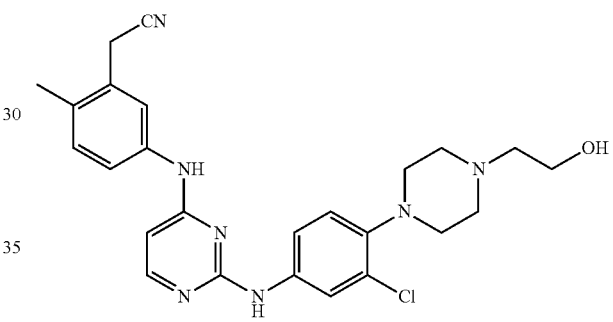

The title compound was synthesized following the procedure depicted in scheme 16. The preparation of 2-(5-amino-2-methylphenyl)acetonitrile (scheme 16 compound 1) is described below.

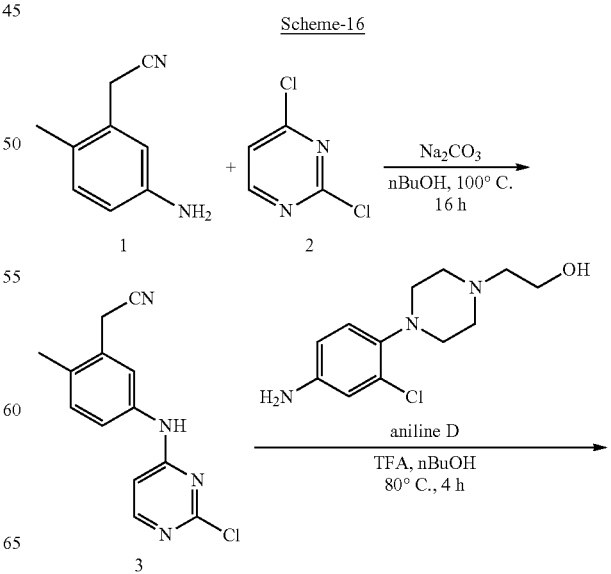

71
-continued

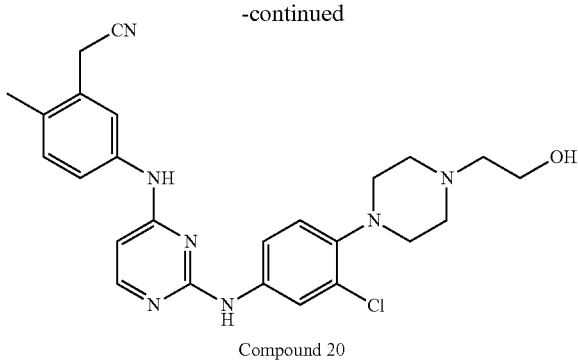

Compound 20

A mixture of scheme 16 compound 1 (700 mg, 4.79 mmol), scheme 16 compound 2 (851 mg, 5.75 mmol) and Na$_2$CO$_3$ (952 mg, 8.98 mmol) in nBuOH (5 mL) was heated to 80° C. for 48 h in a sealed tube. After TLC showed the starting material was consumed completely, the reaction mixture was diluted with water (20 mL) and extracted with EtOAc (2×20 mL). The organic layer was dried over Na$_2$SO$_4$, filtered and concentrated to give a residue which was purified by flash chromatography on neutral alumina (eluting with petroleum ether/EtOAc 100/0 gradually increasing to 70/30) to give scheme 16 compound 3 (350 mg, 47% yield) as an off-white solid. $^1$H NMR (400 MHz, DMSO-d$_6$): δ 10.06 (s, 1H), 8.15 (d, J=5.9 Hz, 1H), 7.60 (s, 1H), 7.52 (d, J=8.4 Hz, 1H), 7.24 (d, J=8.2 Hz, 1H), 6.74 (d, J=5.9 Hz, 1H), 4.01 (s, 2H), 2.25 (s, 3H). MS [ESI, MH$^+$]=259.07.

A mixture of scheme 16 compound 3 (200 mg, 0.77 mmol), aniline D (237 mg, 0.93 mmol) and TFA (2 mL) in nBuOH (10 mL) was heated to 80° C. for 4 h. After TLC showed the starting material was consumed completely, the reaction mixture was diluted with water (20 mL), neutralized with aqueous NaHCO$_3$ (pH 8) and extracted with EtOAc (2×20 mL). The organic layer was dried over Na$_2$SO$_4$, filtered and concentrated to give a residue which was purified by flash chromatography on neutral alumina (eluting with CH$_2$Cl$_2$/MeOH 100/0 gradually increasing to 90/10) to give Compound 20 (66 mg, 18% yield) as an off-white solid. $^1$H NMR (400 MHz, DMSO-d$_6$): δ 9.42 (s, 1H), 9.16 (s, 1H), 8.01 (d, J=5.7 Hz, 1H), 7.90 (d, J=2.6 Hz, 1H), 7.72 (d, J=7.5 Hz, 1H), 7.59-7.51 (m, 2H), 7.18 (d, J=8.3 Hz, 1H), 7.07 (d, J=8.7 Hz, 1H), 6.21 (d, J=5.7 Hz, 1H), 4.43 (t, J=5.3 Hz, 1H), 3.97 (s, 2H), 3.53 (d, J=6.0 Hz, 2H), 2.95-2.87 (m, 4H), 2.57 (s, 4H), 2.45 (t, J=6.3 Hz, 2H), 2.26 (s, 3H). MS [ESI, MH$^+$]=478.12.

2-(5-Amino-2-methylphenyl)acetonitrile (scheme 16 compound 1) was synthesized in a manner similar to scheme 15 compound 5 using 2-methyl-5-nitrobenzoic acid in the first step and was isolated as a brown solid (700 mg, 25% yield over four steps). $^1$H NMR (400 MHz, DMSO-d$_6$): δ 6.91 (d, J=2.2 Hz, 1H), 6.80 (s, 1H), 6.59 (d, J=8.0 Hz, 1H), 4.93 (s, 2H), 3.80 (s, 2H), 2.25 (s, 3H). MS [ESI, MH$^+$]=147.05.

72

Preparation of 2-(5-(2-(3-methoxy-4-(4-methylpiperazin-1-yl)phenylamino)pyrimidin-4-ylamino)-2-methylphenyl)acetonitrile (Compound 21)

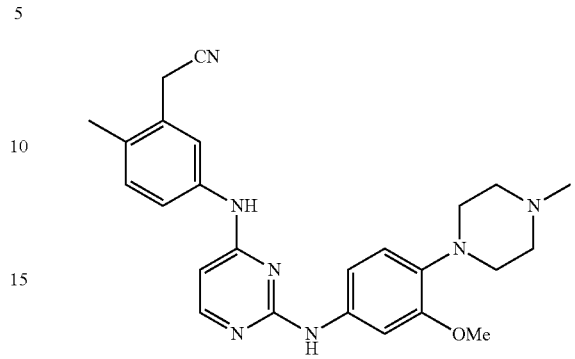

The title compound was synthesized in a similar manner as Compound 20 using aniline B in the final coupling step.

A mixture of scheme 15 compound 3 (150 mg, 0.58 mmol), aniline B (160 mg, 0.63 mmol) and TFA (1 mL) in nBuOH (5 mL) was heated to 80° C. for 4 h. After TLC showed the starting material was consumed completely, the reaction mixture was diluted with water (20 mL), neutralized with aqueous NaHCO$_3$ (pH 8) and extracted with EtOAc (2×20 mL). The organic layer was dried over Na$_2$SO$_4$, filtered and concentrated to give a residue which was purified by flash chromatography on neutral alumina (eluting with CH$_2$Cl$_2$/MeOH 100/0 gradually increasing to 90/10) to give Compound 21 (20 mg, 8% yield) as an off-white solid. $^1$H NMR (400 MHz, CDCl$_3$): δ 8.05 (d, J=5.7 Hz, 1H), 7.53 (d, J=8.8 Hz, 1H), 7.21-7.15 (m, 2H), 7.08 (dd, J=8.5, 2.4 Hz, 1H), 6.92 (d, J=8.5 Hz, 1H), 6.84 (s, 1H), 6.49 (s, 1H), 6.10 (d, J=5.8 Hz, 1H), 3.83 (s, 3H), 3.65 (s, 2H), 3.09 (s, 4H), 2.66 (s, 4H), 2.38 (s, 3H), 2.32 (s, 3H). MS [ESI, MH$^+$]=444.12.

Preparation of 2-(2-(2-(3-chloro-4-(4-(2-hydroxyethyl)piperazin-1-yl)phenylamino)pyrimidin-4-ylamino)-5-fluorophenyl) acetonitrile (Compound 22)

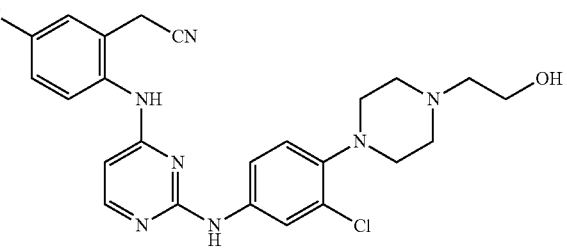

The title compound was synthesized following the procedure depicted in scheme 17

Scheme-17

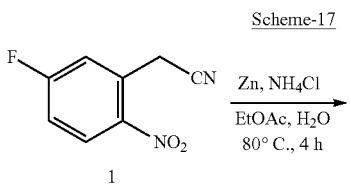

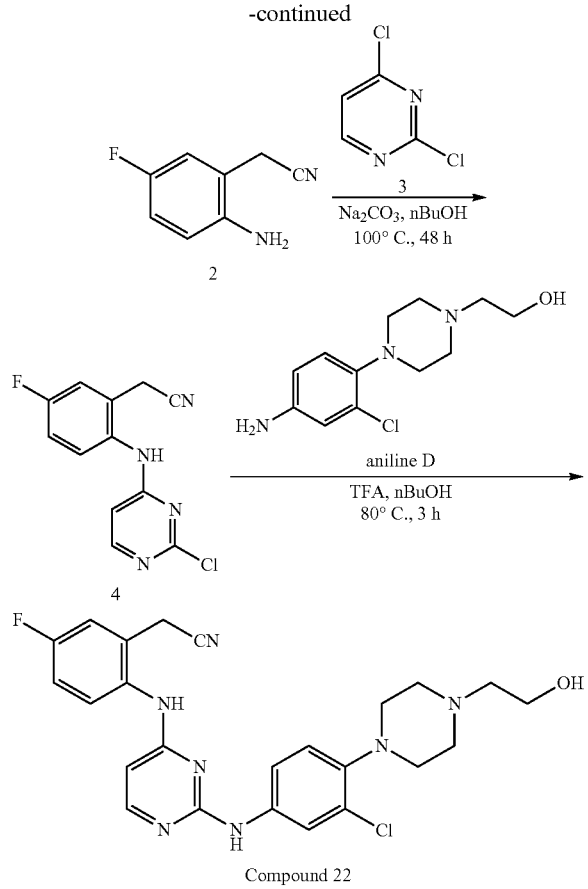

Compound 22

A mixture of scheme 17 compound 1 (0.80 g, 4.45 mmol), Zn dust (1.12 g, 17.77 mmol) and NH₄Cl (2.40 g, 44.5 mmol) in EtOAc/H₂O (20 mL, 1/1) was heated to 80° C. for 4 h. After TLC showed the starting material was consumed completely, the reaction mixture was passed through a pad of celite and the solids were washed with EtOAc. The filtrate was concentrated under reduced pressure to give a residue which was purified by silica gel chromatography (eluting with petroleum ether/EtOAc 100/0 gradually increasing to 60/40) to give scheme 17 compound 2 (0.50 g, 72% yield) as a brown solid. ¹H NMR (400 MHz, DMSO-d₆): δ 7.00-6.86 (m, 2H), 6.68 (m Hz, 1H), 5.05 (s, 2H), 3.79 (s, 2H). MS [ESI, MH⁺]=151.02.

A mixture of scheme 17 compound 2 (500 mg, 3.34 mmol), scheme 17 compound 3 (740 mg, 5.00 mmol) and Na₂CO₃ (708 mg, 6.68 mmol) in nBuOH (5 mL) was heated to 100° C. for 48 h in a sealed tube. After TLC showed the starting material was consumed completely, the reaction mixture was diluted with water (20 mL) and extracted with EtOAc (2×20 mL). The organic layer was dried over Na₂SO₄, filtered and concentrated to give a residue which was purified by silica gel chromatography (eluting with petroleum ether/EtOAc 100/0 gradually increasing to 50/50) to give scheme 17 compound 4 (280 mg, 32% yield) as an off-white solid. ¹H NMR (400 MHz, CDCl₃): δ 8.16 (d, J=5.8 Hz, 1H), 7.33 (m, 2H), 7.20-7.12 (m, 1H), 6.81-6.72 (m, 1H), 6.20 (d, J=5.9 Hz, 1H), 3.71 (s, 2H). MS [ESI, MH⁺]=263.04.

A mixture of scheme 17 compound 4 (200 mg, 0.76 mmol), aniline D (213 mg, 0.85 mmol) and TFA (2 mL) in nBuOH (5 mL) was heated to 80° C. for 3 h. After TLC showed the starting material was consumed completely, the reaction mixture was diluted with water (20 mL), neutralized with aqueous NaHCO₃ (pH 8) and extracted with EtOAc (2×20 mL). The organic layer was dried over Na₂SO₄, filtered and concentrated to give a residue which was purified by flash chromatography on neutral alumina (eluting with CH₂Cl₂/MeOH 100/0 gradually increasing to 90/10) to give Compound 22 (45 mg, 12% yield) as a light yellow solid. ¹H NMR (400 MHz, DMSO-d₆): δ 9.11 (s, 1H), 8.96 (s, 1H), 8.00 (d, J=5.7 Hz, 1H), 7.76 (s, 1H), 7.46 (m, 1H), 7.43-7.29 (m, 2H), 7.25 (m, 1H), 6.95 (d, J=8.8 Hz, 1H), 6.13 (d, J=5.7 Hz, 1H), 4.41 (d, J=6.2 Hz, 1H), 3.96 (s, 2H), 3.52 (d, J=6.0 Hz, 2H), 2.86 (s, 4H), 2.56 (s, 4H), 2.44 (d, J=5.9 Hz, 2H). MS [ESI, MH⁺]=482.03.

Preparation of 2-(5-fluoro-2-(2-(3-methoxy-4-(4-methylpiperazin-1-yl)phenylamino)pyrimidin-4-ylamino)phenyl)acetonitrile (Compound 23)

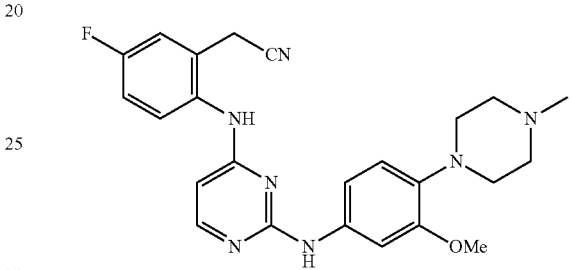

The title compound was synthesized in a similar manner as Compound 22 using aniline B in the final coupling step.

A mixture of scheme 17 compound 4 (200 mg, 0.76 mmol), aniline B (229 mg, 0.91 mmol) and TFA (2 mL) in nBuOH (5 mL) was heated to 80° C. for 3 h. After TLC showed the starting material was consumed completely, the reaction mixture was diluted with water (20 mL), neutralized with aqueous NaHCO₃ (pH 8) and extracted with EtOAc (2×20 mL). The organic layer was dried over Na₂SO₄, filtered and concentrated to give a residue which was purified by flash chromatography on neutral alumina (eluting with CH₂Cl₂/MeOH 100/0 gradually increasing to 90/10) to give Compound 23 (60 mg, 17% yield) as a light yellow solid. ¹H NMR (400 MHz, CDCl₃): δ 8.03 (d, J=5.7 Hz, 1H), 7.34-7.28 (m, 2H), 7.12 (d, J=2.9 Hz, 2H), 6.98 (dd, J=8.5, 2.4 Hz, 1H), 6.90-6.81 (m, 2H), 6.21 (s, 1H), 5.81 (d, J=5.7 Hz, 1H), 3.79 (s, 3H), 3.71 (s, 2H), 3.09 (s, 4H), 2.69 (s, 4H), 2.40 (s, 3H). MS [ESI, MH⁺]=448.02.

Preparation of 2-(6-(2-(3-chloro-4-(4-(2-hydroxyethyl)piperazin-1-yl)phenylamino)pyrimidin-4-ylamino)-2,3-dimethylphenyl) acetonitrile (Compound 24)

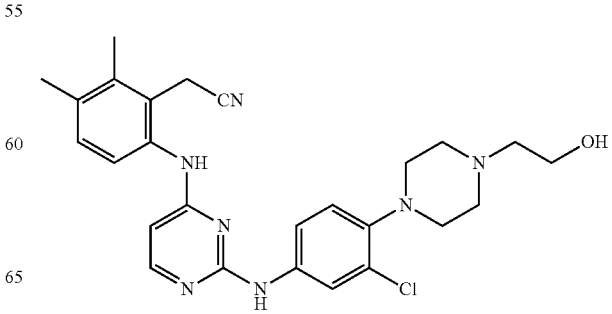

The title compound was synthesized following the procedure depicted in scheme 18. The preparation of 2-(6-amino-2,3-dimethylphenyl)acetonitrile (scheme 18 compound 1) is described below in scheme 19.

Scheme 18

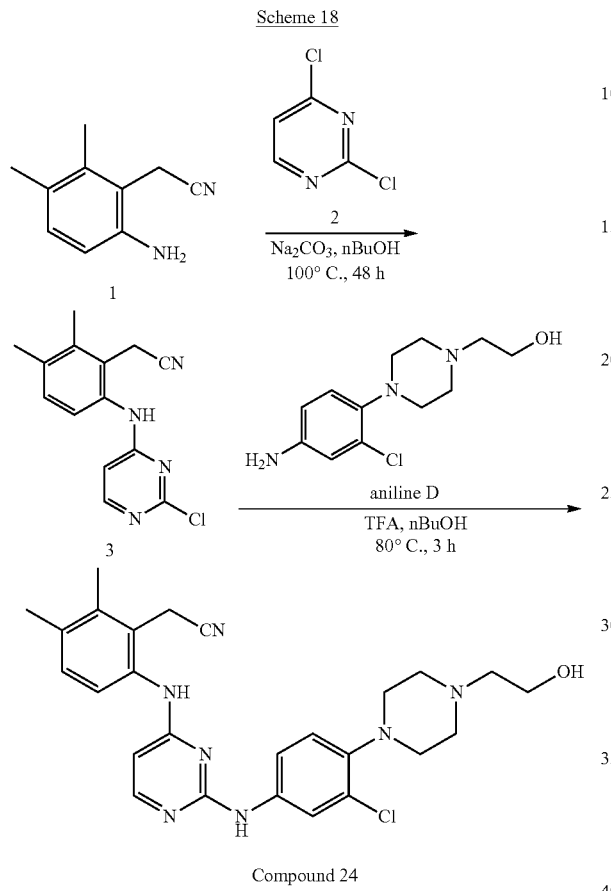

A mixture of scheme 18 compound 1 (500 mg, 3.12 mmol), scheme 18 compound 2 (925 mg, 6.25 mmol) and Na₂CO₃ (662 mg, 6.25 mmol) in nBuOH (10 mL) was heated to 100° C. for 16 h in a sealed tube. After TLC showed the starting material was consumed completely, the reaction mixture was diluted with water (20 mL) and extracted with EtOAc (2×20 mL). The organic layer was dried over Na₂SO₄, filtered and concentrated to give a residue which was purified by flash chromatography on neutral alumina (eluting with petroleum ether/EtOAc 100/0 gradually increasing to 50/50) to give scheme 18 compound 3 (200 mg, 24% yield) as an off-white solid. ¹H NMR (400 MHz, CDCl₃): δ 8.07 (d, J=5.9 Hz, 1H), 7.56 (s, 1H), 7.16 (s, 2H), 6.48 (d, J=5.9 Hz, 1H), 4.76 (s, 3H), 2.36 (s, 3H), 2.32 (s, 3H). MS [ESI, MH⁺]=273.01.

Scheme 18 compound 3 (150 mg, 0.55 mmol), aniline D (168 mg, 0.66 mmol) and TFA (1 mL) in nBuOH (5 mL) were heated to 80° C. for 3 h. After TLC showed the starting material was consumed completely, the reaction mixture was diluted with water (20 mL), neutralized with aqueous NaHCO₃ (pH 8) and extracted with EtOAc (2×20 mL). The organic layer was dried over Na₂SO₄, filtered and concentrated to give a residue which was purified by flash chromatography on neutral alumina (eluting with CH₂Cl₂/MeOH 100/0 gradually increasing to 90/10) to give Compound 24 (25 mg, 9% yield) as an off-white solid. ¹H NMR (400 MHz, CDCl₃): δ 7.99 (d, J=5.7 Hz, 1H), 7.68 (d, J=2.6 Hz, 1H), 7.26-7.24 (m, 1H), 7.18 (d, J=7.9 Hz, 1H), 7.09 (s, 1H), 6.96 (d, J=8.80 Hz, 1H), 6.76 (s, 1H), 6.05 (d, J=5.7 Hz, 1H), 4.76 (s, 2H), 3.66 (t, J=5.3 Hz, 2H), 3.03 (m, 4H), 2.71 (m, 4H), 2.64 (t, J=5.3 Hz, 2H), 2.35 (s, 3H), 2.32 (s, 3H). MS [ESI, MH⁺]=492.10.

2-(6-Amino-2,3-dimethylphenyl)acetonitrile (Scheme 18 Compound 1) was Synthesized as Shown in Scheme 19.

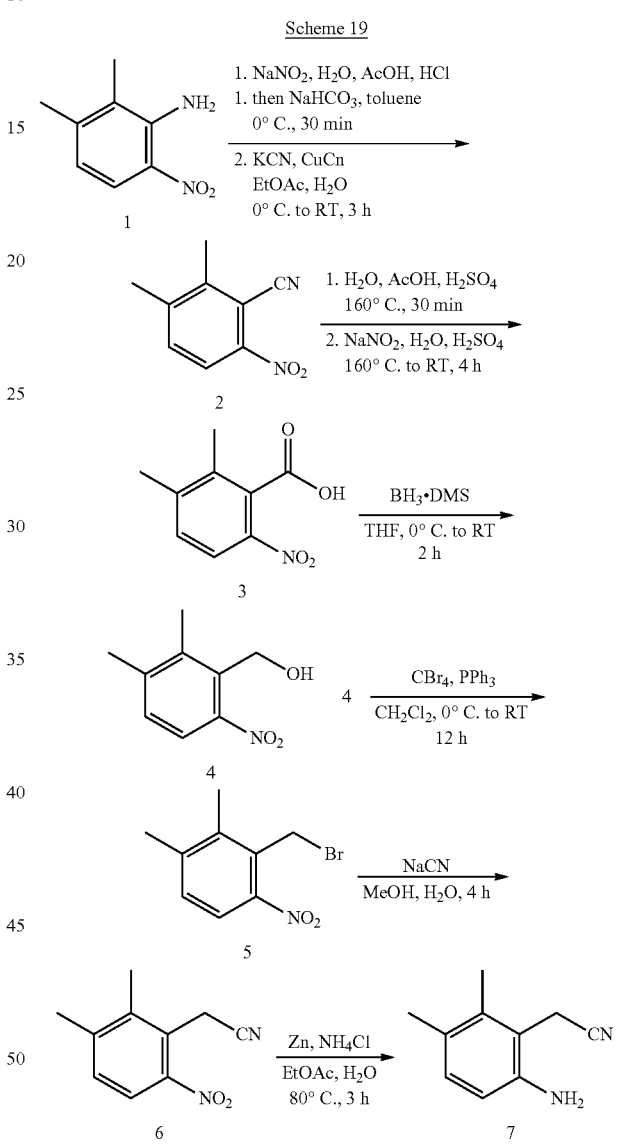

NaNO₂ (4.98 g, 72.28 mmol) in water (30 mL) was added dropwise to of a solution of scheme 19 compound 1 (10.00 g, 60.24 mmol) in AcOH (25 mL) and 6N HCl (30 mL) followed by NaHCO₃ (30.00 g, 35.71 mmol) and toluene (25 mL) and the resulting mixture was stirred at 0° C. for 30 min. This solution was then added to a stirred mixture of KCN (31.30 g, 481.90 mmol) and CuCN (11.79 g, 132.50 mmol) in EtOAc (50 mL) and water (70 mL) at 0° C. and the reaction mixture was slowly warmed to RT over the course of 3 h. After TLC showed the starting material was consumed completely, the reaction mixture was diluted with EtOAc (60 mL). The organic layer was separated and dried over Na$_2$SO$_4$ then filtered and concentrated to give a residue which was purified by flash chromatography on silica gel (eluting with petroleum ether/EtOAc 100/0 gradually increasing to 60/40) to give scheme 19 compound 2 (6.60 g, 62% yield) as a yellow solid. $^1$H NMR (400 MHz, DMSO-d$_6$): δ 8.15 (d, J=8.4 Hz, 1H), 7.76 (d, J=8.4 Hz, 1H), 2.54 (s, 3H), 2.43 (s, 3H). MS [ESI, MH$^+$]=177.06.

A solution of scheme 19 compound 2 (6.60 g, 37.5 mmol) in water (60 mL), AcOH (60 mL) and H$_2$SO$_4$ (60 mL) was stirred at 160° C. for 6 h. After TLC showed the starting material was consumed completely, the reaction mixture was diluted with ice water (30 mL) and extracted with EtOAc (2×100 mL). The organic layer was washed with brine (20 mL), dried over (Na$_2$SO$_4$) and concentrated to give a residue which was dissolved in 25% aqueous H$_2$SO$_4$ and heated to 160° C. NaNO$_2$ (3.98 g, 56.7 mmol) in water (30 mL) was added dropwise to this solution which was allowed to cool to RT over the course of 4 h. After TLC showed the starting material was consumed completely, the reaction mixture was diluted with ice water (30 mL) and extracted with EtOAc (2×100 mL). The organic layer was washed with brine (20 mL), dried over (Na$_2$SO$_4$) and concentrated to give a residue which was purified by flash chromatography on silica gel (eluting with CH$_2$Cl$_2$/MeOH 100/0 gradually increasing to 90/10) to give scheme 19 compound 3 (3.00 g, 55% yield) as an off-white solid. $^1$H NMR (400 MHz, DMSO-d$_6$): δ 13.67 (s, 1H), 7.92 (d, J=8.4 Hz, 1H), 7.47 (d, J=8.4 Hz, 1H), 2.36 (s, 3H), 2.24 (s, 3H). MS [ESI, (M-H)$^-$]=194.07.

To a cold (0° C.) stirred solution of scheme 19 compound 3 (3.0 g, 15.38 mmol) in dry THF (30 mL) was added BH$_3$.DMS (2M in THF, 30.7 mL, 61.53 mmol) dropwise and the reaction mixture was stirred at 80° C. for 2 h. After TLC showed the starting material was consumed completely, the reaction mixture was diluted with ice water (30 mL) and extracted with EtOAc (2×50 mL). The organic layer was washed with brine (20 mL) then dried over (Na$_2$SO$_4$) and concentrated to give a residue which was purified by flash chromatography on silica gel (eluting with petroleum ether/EtOAc 100/0 gradually increasing to 30/70) to give scheme 19 compound 4 (2.5 g, 89% yield) as an off-white solid. $^1$H NMR (400 MHz, DMSO-d$_6$): δ 7.52 (d, J=8.2 Hz, 1H), 7.30 (d, J=8.2 Hz, 1H), 5.18 (t, J=5.4 Hz, 1H), 4.61 (d, J=3.3 Hz, 2H), 2.33 (s, 3H), 2.31 (s, 3H). MS [ESI, MH$^+$]=182.05.

To a cold (0° C.) stirred solution of scheme 19 compound 4 (2.5 g, 13.81 mmol) in dry CH$_2$Cl$_2$ (25 mL) was added PPh$_3$ (7.2 g, 27.62 mmol) and CBr$_4$ (9.2 g, 27.62 mmol) and the reaction mixture was stirred at RT for 12 h. After TLC showed the starting material was consumed completely, the reaction mixture was concentrated under reduced pressure to give a residue which was purified by flash chromatography on silica gel (eluting with petroleum ether/EtOAc 100/0 gradually increasing to 60/40) to give scheme 19 compound 5 (2.3 g, 67% yield) as a brown liquid. $^1$H NMR (400 MHz, DMSO-d$_6$): δ 7.72 (d, J=8.3 Hz, 1H), 7.41 (d, J=8.3 Hz, 1H), 4.79 (s, 2H), 2.36 (s, 3H), 2.35 (s, 3H). MS [ESI, MH$^+$]=243.96.

To a solution of scheme 19 compound 5 (2.30 g, 9.23 mmol) in MeOH (20 mL) and water (6 mL) was added NaCN (0.59 g, 12.00 mmol) and the reaction mixture was stirred at RT for 4 h. After TLC showed the starting material was consumed completely, the reaction mixture was diluted with water (20 mL) and extracted with EtOAc (30 mL). The organic layer was dried over Na$_2$SO$_4$, filtered and concentrated to give a residue which was purified by flash chromatography on silica gel (eluting with petroleum ether/EtOAc 100/0 gradually increasing to 40/60) to give scheme 19 compound 6 (1.10 g, 64% yield) as an off-white solid. $^1$H NMR (400 MHz, CDCl$_3$): δ 7.79 (d, J=8.4 Hz, 1H), 7.32 (d, J=8.4 Hz, 1H), 3.96 (s, 2H), 2.43 (d, J=1.9 Hz, 6H). MS [ESI, MH$^+$]=191.08.

A mixture of scheme 19 compound 6 (1.10 g, 5.78 mmol), Zn dust (1.51 g, 23.15 mmol) and NH$_4$Cl (3.09 g, 57.8 mmol) in EtOAc/H$_2$O (20 mL, 1/1) was heated to 80° C. for 3 h. After TLC showed the starting material was consumed completely, the reaction mixture was passed through a pad of celite and the solids were washed with EtOAc. The filtrate was evaporated under reduced pressure to give a residue which was purified by flash chromatography on silica gel (eluting with petroleum ether/EtOAc 100/0 gradually increasing to 60/40) to give scheme 19 compound 7 (0.60 mg, 65% yield) as a yellow solid. $^1$H NMR (400 MHz, DMSO-d$_6$): δ 6.82 (d, J=8.1 Hz, 1H), 6.47 (d, J=8.0 Hz, 1H), 4.96 (s, 2H), 3.76 (s, 2H), 2.14 (s, 3H), 2.10 (s, 3H). MS [ESI, MH$^+$]=161.10.

Other compounds of structure (I) (or structure (II)) are prepared in a manner analogous to that described above.

Example 2

Testing of the Compounds

Biochemical assays to measure the inhibitory effects of the compounds were performed by the Drug Discovery and Development Services at Life Technologies (Madison, Wis.). JAK2 kinase assays were performed using Z'-LYTE® technology, while ALK2 inhibition was tested using a LanthaScreen® binding assay. Results are shown in Table 1 above.

Figure 2:
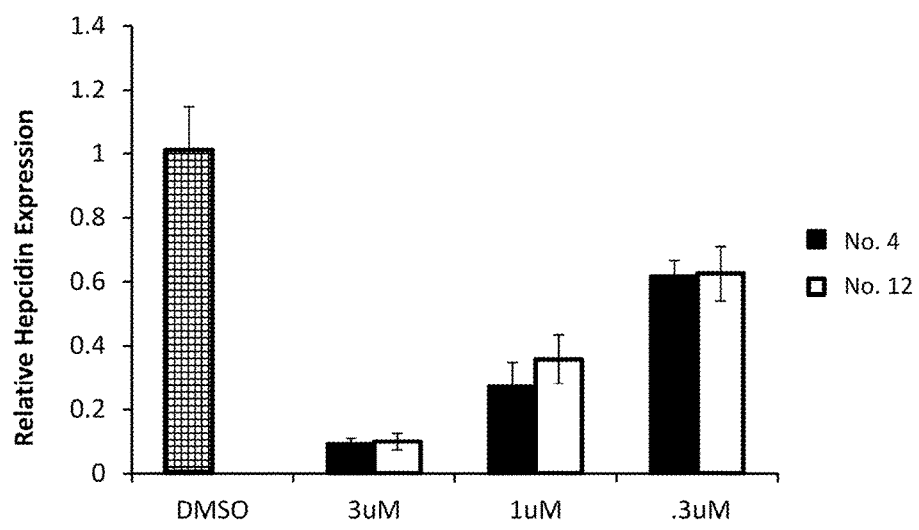
FIG. 2 is a bar graph of hepcidin expression as a function of concentration of Compound No. 4 (left bars) and Compound No. 12 (right bars).
Figure 3:
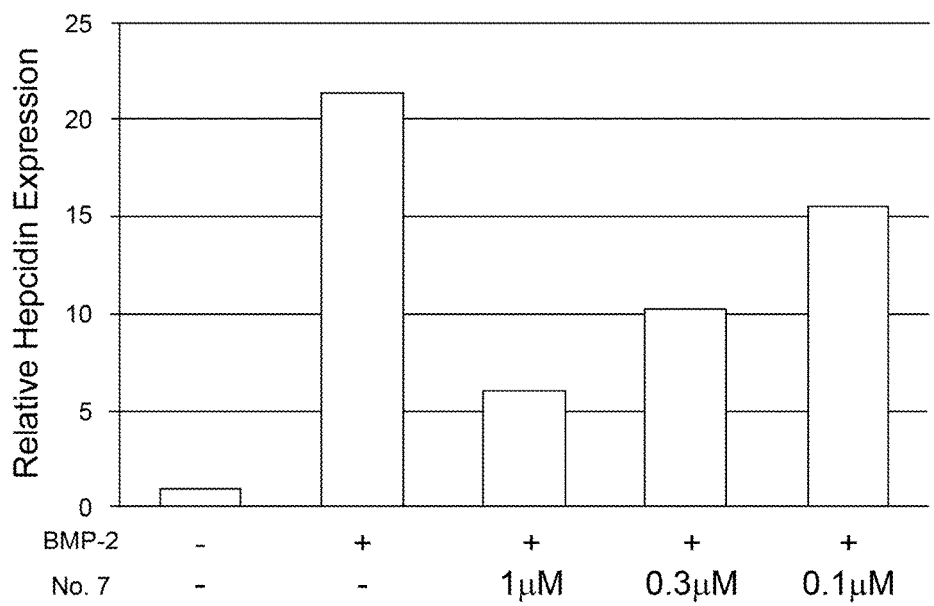
FIG. 3 shows hepcidin expression data in the presence and absence of BMP-2.

Hepcidin expression of HEPG2 cells treated with exemplary compounds of the invention was tested. Results are displayed in FIGS. 1-3. Reference: In PNAS vol 103no27 10289-10293 shows that in HepG2 cells, BMP2 induces hepcidin higher than IL-6, BMP4, and BMP9 at 100 ng/μL. BMP2 and BMP4 bind to ALK2, ALK3, and ALK6. To observe the ability of the compounds to effect baseline hepcidin expression, HEPG2 (hepatocellular carcinoma) cells were treated with compound for 6 hours and then assayed for hepcidin expression by real-time RT-PCR (normalized to levels of β-actin). Hepcidin expression was lowered in a dose dependent manner. Hepcidin expression was inhibited by 90% at a 3 μM concentration of Compound 12. A second approach evaluated the ability of the compounds to inhibit hepcidin expression induced by BMP2. BMP2 induces hepcidin expression by binding to and activating ALK2. HEPG2 cells were treated with compound then with BMP2 at 100 ng/μL. BMP2 addition caused hepcidin to increase by >20-fold. In contrast, Compound 7 treated cells produced a 50% decrease in the induction when treated at 0.3 μM. As shown in FIG. 3, the ability to block BMP2 signaling is dose dependent.

Figure 4:
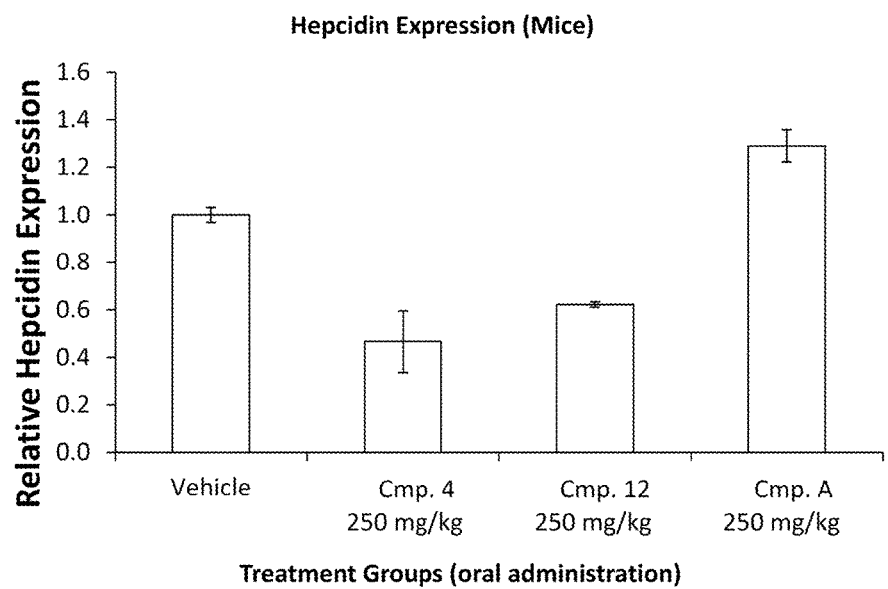
FIG. 4 is a bar graph showing hepcidin expression in mice for representative compounds and a comparative compound.

Hepcidin expression in the mice treated with compounds 4 and 12 was compared to hepcidin expression in mice treated with compound A. In this experiment, mice were treated orally with a single dose of test compound. After six hours, livers were removed from euthanized animals and RNA extracted. Hepcidin mRNA levels were determined by real-time RT-PCR as described above. As seen in FIG. 4, compounds 4 and 12 inhibit hepcidin expression to a greater extent than compound A at the tested dose (250 mg/kg).

Compound A

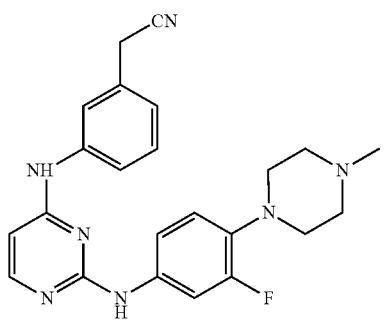

Figure 5:
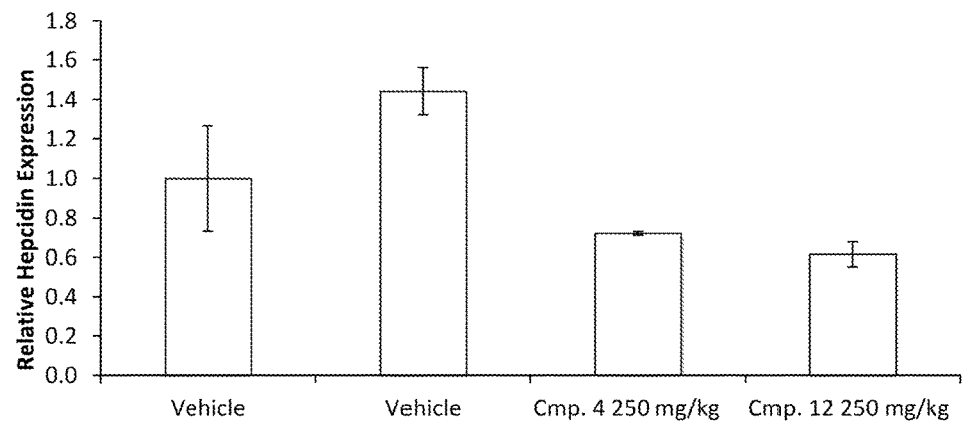
FIG. 5 shows in vivo hepcidin expression in the LPS-induced mouse model.

Similar to the above study, compounds 4 and 12 were evaluated in an LPS-induced mouse model. LPS is commonly used in animal studies to elicit a cytokine-driven immune response with associated anemia. In this experiment, compound 4 or 12 was administered orally as a single dose of 250 mg/kg followed by the intraperitoneal administration of 1 mg/kg of LPS. After six hours, hepcidin expression was analyzed by RT-PCR as described above. Results are presented in FIG. 5.

Figure 6:
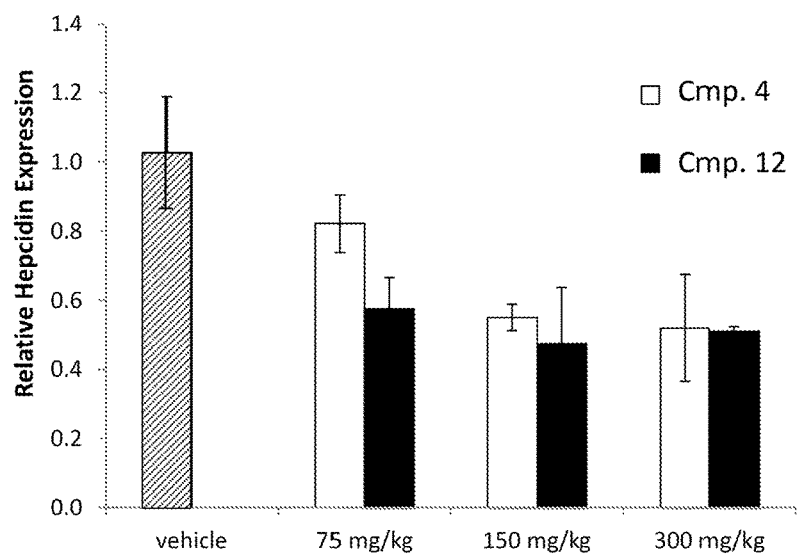
FIG. 6 presents dose response data for representative compounds.

To determine the in vivo activity of compounds 4 and 12 at dose levels below 250 mg/kg, mice were treated with a single dose of test compound at 75, 150 or 300 mg/kg. Again liver hepcidin levels were measured as described above. FIG. 6 shows results of dose response studies in a mouse model for compounds 4 and 12.

Figure 7A:
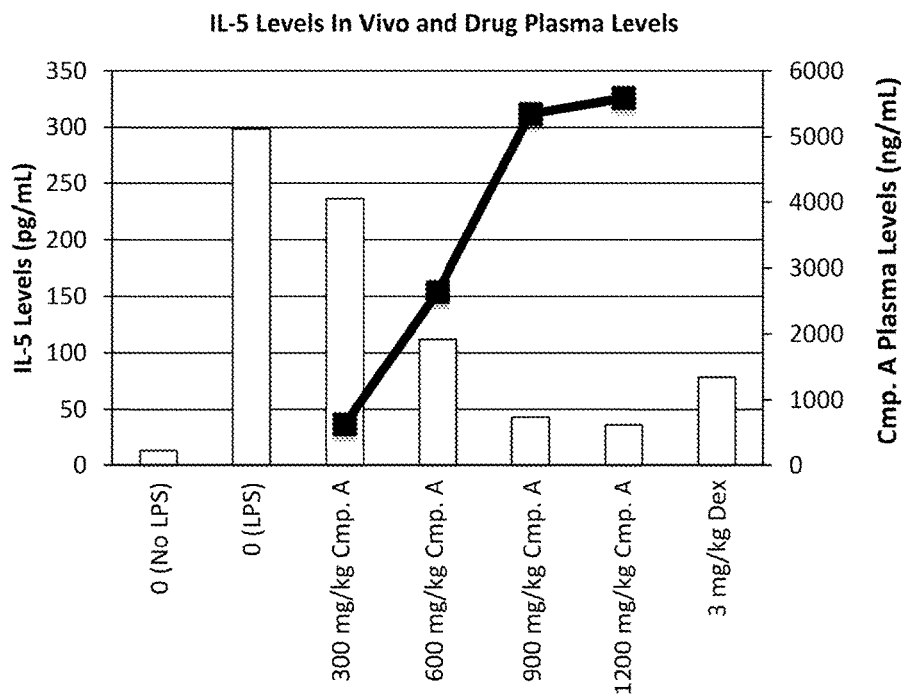
FIGS. 7A and 7B show IL-5 levels in vivo at different doses of comparative compound and representative compounds, respectively.
Figure 7B:
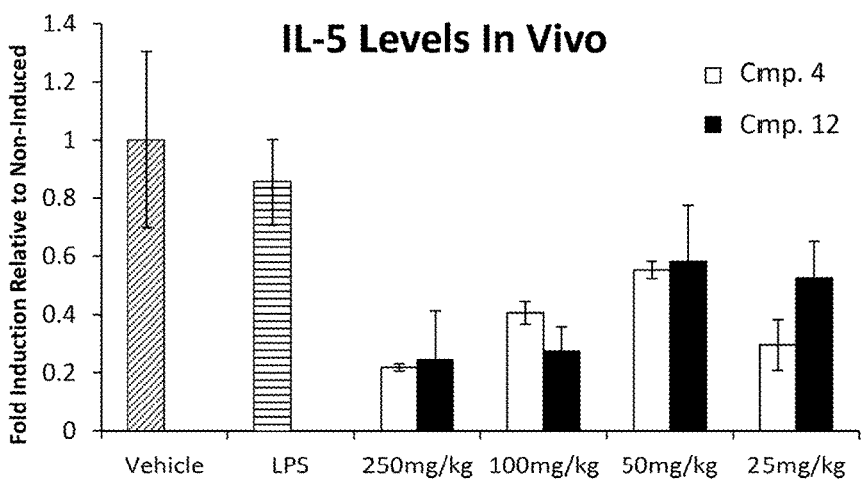
Figure 8:
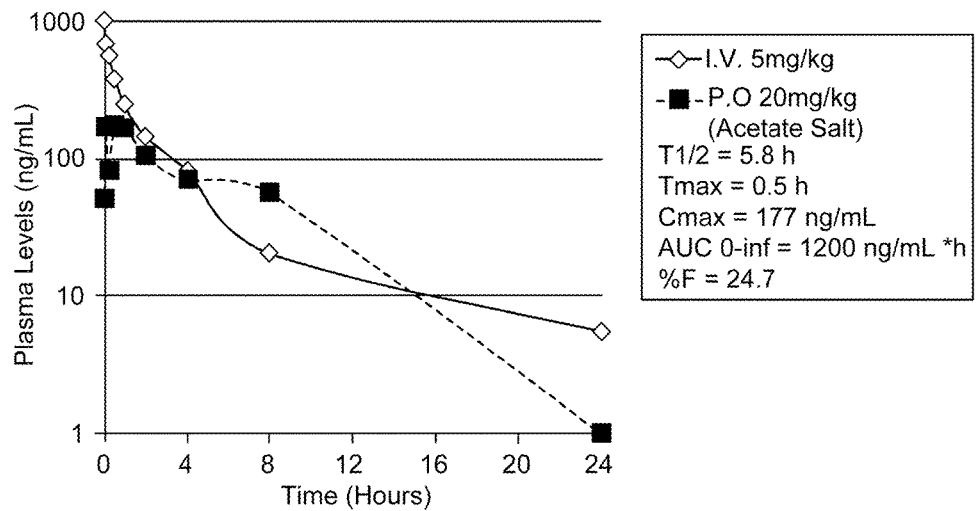
FIG. 8 presents pharmacokinetic data.

In addition to lowering hepcidin levels, these compounds have also demonstrated promising activity at modulating cytokine levels in vivo. LPS was again used to induce a cytokine response and the test compounds were evaluated to determine if induced cytokine responses could be reversed or prevented by treatment with compound 4 or 12. Several cytokines were included in this study and FIG. 7 compares modulation of IL-5 cytokine (as an example) by compounds 4 and 12 and compound A. A pharmacokinetic profile was also performed for compound no. 4, using both IV and PO administration. Results are tabulated in Table 2. The data demonstrate that bioavailability can be increased by using salt forms of compound no. 4. Compound 4 pharmacokinetic properties were determined in female rats. FIG. 8 shows the plasma levels at given time points for both the I.V. and the orally dosed rats (graph shows average of 3) and the pharmacokinetic parameters of the compound dosed orally. The data show that plasma concentration levels of Compound 4 remain high even after 24 hours.

TABLE 2

Pharmacokinetic Profile of Compound No. 4

| | Parameter | | | | |
| --- | --- | --- | --- | --- | --- |
| | t½ | Tmax | Cmax | AUC 0-inf | F |
| | Unit | | | | |
| | (h) | (h) | (ng/mL) | (ng/mL * h) | (% IV) |
| IV | 9.2 | 0.0 | 996.2 | 1377.2 | 100.0 |
| Free base | 6.5 | 2.0 | 118.4 | 852.5 | 15.4 |
| HCl | 7.7 | 1.0 | 66.7 | 422.8 | 10.0 |
| H2SO4 | 9.2 | 1.0 | 53.8 | 538.3 | 17.8 |
| Tartaric | 10.4 | 0.3 | 18.5 | 370.9 | 26.1 |
| Mesylate | 9.7 | <0.1 | 64.0 | 481.8 | 13.8 |
| Acetate | 5.8 | 0.5 | 176.8 | 1200.1 | 24.7 |
| Maleate | 8.5 | 8.0 | 34.2 | 484.8 | 12.1 |
| Oxalate | 7.3 | 0.5 | 81.9 | 721.2 | 17.3 |
| Citrate | 6.8 | 0.5 | 93.4 | 801.5 | 22.4 |

Figure 9:
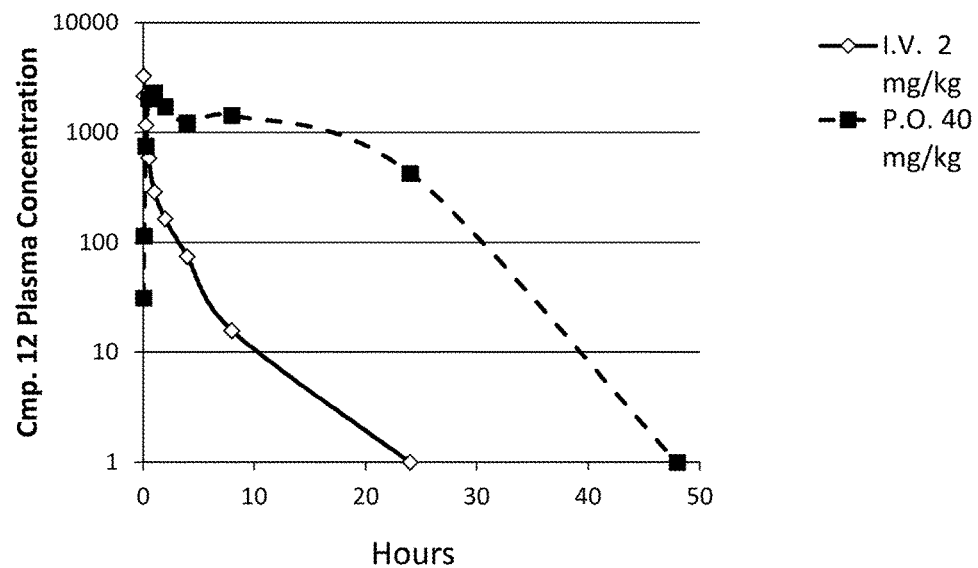
FIG. 9 is a graph showing plasma concentration levels of an exemplary compound as a function of time.

Compound 12 pharmacokinetic properties were quantified in female rats. FIG. 9 shows the plasma levels at given time points for both the IV and the orally dosed rats (graph shows average of 3) and the pharmacokinetic parameters of the compound dosed orally. Compound levels of Compound 12 remained high in the plasma even at 24 hrs in the oral dose. The oral bioavailability of Compound 12 is exceptionally good at 95%.

The various embodiments described above can be combined to provide further embodiments. All U.S. patents, U.S. patent application publications, U.S. patent applications, non-U.S. patents, non-U.S. patent applications, and non-patent publications referred to in this specification and/or listed in the Application Data Sheet are incorporated herein by reference, in their entirety. Aspects of the embodiments can be modified, if necessary, to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A compound having the following structure:

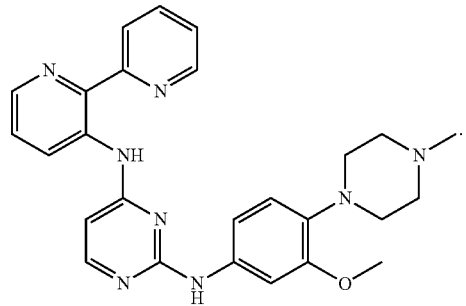 [SMILES: COc1cc(Nc2nccc(Nc3cccnc3-c3ccccn3)n2)ccc1N1CCN(C)CC1]

2. A pharmaceutically acceptable salt of a compound having the following structure:

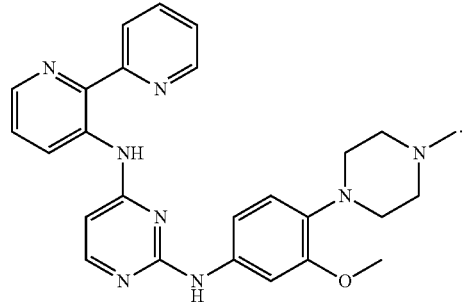 [SMILES: COc1cc(Nc2nccc(Nc3cccnc3-c3ccccn3)n2)ccc1N1CCN(C)CC1]

3. The pharmaceutically acceptable salt of claim 2, wherein the pharmaceutically acceptable salt is an acid addition salt.

4. The pharmaceutically acceptable salt of claim 3, wherein the acid addition salt is a hydrochloric acid salt.

5. The pharmaceutically acceptable salt of claim 3, wherein the acid addition salt is a fumaric acid salt.

6. A pharmaceutical composition comprising a compound having the following structure:

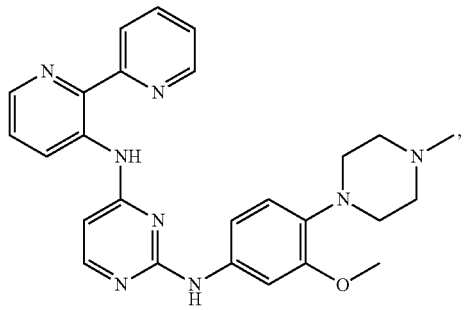 [SMILES: COc1cc(Nc2nccc(Nc3cccnc3-c3ccccn3)n2)ccc1N1CCN(C)CC1]

and a pharmaceutically acceptable carrier, diluent or excipient.

7. A pharmaceutical composition comprising a pharmaceutically acceptable salt of a compound having the following structure:

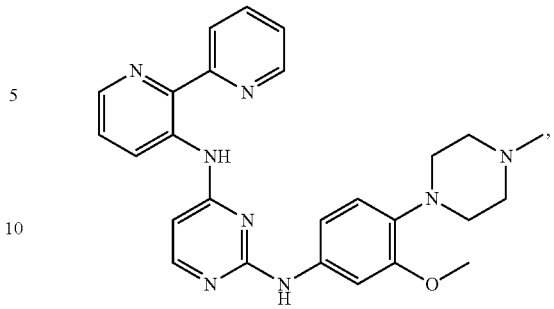

and a pharmaceutically acceptable carrier, diluent or excipient.

8. The pharmaceutical composition of claim 7, wherein the pharmaceutically acceptable salt is an acid addition salt.

9. The pharmaceutical composition of claim 8, wherein the acid addition salt is a hydrochloric acid salt.

10. The pharmaceutical composition of claim 8, wherein the acid addition salt is a fumaric acid salt.

* * * * *

UNITED STATES PATENT AND TRADEMARK OFFICE
CERTIFICATE OF CORRECTION

Page 1 of 1

PATENT NO. : 10,202,356 B2
APPLICATION NO. : 14/776392
DATED : February 12, 2019
INVENTOR(S) : Alexis Mollard et al.

It is certified that error appears in the above-identified patent and that said Letters Patent is hereby corrected as shown below:

On the Title Page

Page 2, Column 1, Line 9:
Item (56), References Cited, Foreign Patent Documents:
"WO   2007/05452   A1   5/2007" should read,
--WO   2007/053452   A1   5/2007--.

Page 2, Column 2, Line 29:
Item (56), References Cited, Other Publications:
"Hafizi et al., "Signalling and functional diversity within the Axl subfamily of receptor tyrosinekinases," *Cytokine & Growth Factor Reviews* 17:295-304, 2006." should read,
--Hafizi et al., "Signalling and functional diversity within the Axl subfamily of receptor tyrosine kinases," *Cytokine & Growth Factor Reviews* 17:295-304, 2006.--.

Signed and Sealed this
Fourteenth Day of July, 2020

Andrei Iancu
*Director of the United States Patent and Trademark Office*